United States Patent
Ritchey et al.

(10) Patent No.: US 9,585,722 B2
(45) Date of Patent: Mar. 7, 2017

(54) TARGETING AN ORTHOPAEDIC IMPLANT LANDMARK

(71) Applicant: Smith & Nephew, Inc., Memphis, TN (US)

(72) Inventors: Nicholas S. Ritchey, Collierville, TN (US); Sied W. Janna, Memphis, TN (US); Hoa La Wilhelm, Arlington, TN (US); Charles C. Heotis, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/708,678

(22) Filed: May 11, 2015

(65) Prior Publication Data
US 2015/0238277 A1    Aug. 27, 2015

Related U.S. Application Data

(63) Continuation of application No. 12/758,747, filed on Apr. 12, 2010, now Pat. No. 9,031,637, which is a
(Continued)

(51) Int. Cl.
*A61F 2/46* (2006.01)
*A61B 19/00* (2006.01)
(Continued)

(52) U.S. Cl.
CPC ............ *A61B 19/5244* (2013.01); *A61B 5/05* (2013.01); *A61B 5/06* (2013.01); *A61B 5/1127* (2013.01);
(Continued)

(58) Field of Classification Search
CPC ................ A61B 17/88; A61B 19/5244; A61B 2019/5272
See application file for complete search history.

(56) References Cited

U.S. PATENT DOCUMENTS 3,219,969 A    11/1965   Snavely
4,353,110 A    10/1982   Ellis
(Continued)

FOREIGN PATENT DOCUMENTS

CA    2571508       1/2006
CN    2698283 Y    5/2005
(Continued)

OTHER PUBLICATIONS

Notice of Preliminary Rejection for Korean Application No. 10-2011-7027567 mailed May 30, 2016.
(Continued)

*Primary Examiner* — Ellen C Hammond
*Assistant Examiner* — Stuart S Bray
(74) *Attorney, Agent, or Firm* — Fish & Richardson P.C.

(57) ABSTRACT

A system for targeting landmarks on devices such as surgical implants is disclosed. The system can include a field generator for generating one or more magnetic fields, an orthopedic implant located within the magnetic fields, the implant having at least one landmark, a removable probe with a first magnetic sensor, a landmark identifier and a processor. The landmark identifier can contain a second sensor, or, alternatively, the field generator. The processor can utilize sensor data and, if desirable, field generator and other information, to generate and display the position and orientation of the sensor(s) in preferably six degrees of freedom, and thereby, to generate and display the position and orientation of the landmark(s). The system allows for blind targeting of one or more landmarks. The landmark identifier, field generator and/or drill motor may be disposed in an autoclavable housing.

20 Claims, 42 Drawing Sheets

Related U.S. Application Data continuation-in-part of application No. 12/547,716, filed on Aug. 26, 2009, now Pat. No. 8,784,425.

(60) Provisional application No. 61/173,069, filed on Apr. 27, 2009.

(51) Int. Cl.
  *A61B 5/05* (2006.01)
  *A61B 5/06* (2006.01)
  *A61B 5/11* (2006.01)
  *A61B 17/17* (2006.01)

(52) U.S. Cl.
  CPC ...... *A61B 17/1707* (2013.01); *A61B 17/1725* (2013.01); *A61B 34/20* (2016.02); *A61B 2034/2051* (2016.02); *A61B 2034/2072* (2016.02); *A61B 2090/0813* (2016.02)

(56) References Cited

U.S. PATENT DOCUMENTS

| | | | |
|---|---|---|---|
| 4,532,599 A | 7/1985 | Smith | |
| 4,621,628 A | 11/1986 | Brudermann | |
| D297,047 S | 8/1988 | Hon et al. | |
| 4,794,930 A | 1/1989 | Machida et al. | |
| 4,803,976 A | 2/1989 | Frigg et al. | |
| 5,049,151 A | 9/1991 | Durham et al. | |
| 5,127,913 A | 7/1992 | Thomas | |
| 5,217,009 A * | 6/1993 | Kronberg ........... A61N 1/36014 607/51 | |
| 5,251,127 A | 10/1993 | Raab | |
| 5,281,224 A | 1/1994 | Faccioli et al. | |
| 5,361,766 A | 11/1994 | Nichols et al. | |
| 5,383,917 A | 1/1995 | Desai et al. | |
| 5,411,503 A | 5/1995 | Hollstien et al. | |
| 5,412,185 A * | 5/1995 | Sturman, Jr. ............ B01J 3/04 219/602 | |
| 5,417,688 A | 5/1995 | Elstrom et al. | |
| 5,433,720 A | 7/1995 | Faccioli et al. | |
| 5,514,145 A | 5/1996 | Durham et al. | |
| 5,580,156 A | 12/1996 | Suzuki et al. | |
| 5,584,838 A | 12/1996 | Rona et al. | |
| 5,585,783 A | 12/1996 | Hall | |
| 5,957,836 A | 9/1999 | Johnson | |
| 5,957,934 A | 9/1999 | Rapoport | |
| 6,009,878 A | 1/2000 | Weijand et al. | |
| 6,036,696 A | 3/2000 | Lambrecht et al. | |
| 6,039,742 A | 3/2000 | Krettek et al. | |
| 6,074,394 A | 6/2000 | Krause | |
| 6,081,741 A | 6/2000 | Hollis | |
| 6,106,528 A | 8/2000 | Durham et al. | |
| 6,157,853 A | 12/2000 | Blume et al. | |
| 6,162,228 A | 12/2000 | Durham | |
| 6,168,595 B1 | 1/2001 | Durham et al. | |
| 6,174,335 B1 | 1/2001 | Varieur et al. | |
| 6,212,419 B1 | 4/2001 | Blume et al. | |
| 6,233,490 B1 | 5/2001 | Kasevich | |
| 6,266,551 B1 | 7/2001 | Osadchy et al. | |
| 6,267,770 B1 | 7/2001 | Truwit | |
| 6,304,091 B1 | 10/2001 | Shahoian et al. | |
| 6,311,082 B1 | 10/2001 | Creighton et al. | |
| 6,474,341 B1 | 11/2002 | Hunter et al. | |
| 6,503,249 B1 | 1/2003 | Krause | |
| 6,575,973 B1 | 6/2003 | Shekalim | |
| 6,636,757 B1 | 10/2003 | Jascob et al. | |
| 6,675,491 B2 | 1/2004 | Sasaki et al. | |
| 6,694,168 B2 | 2/2004 | Traxel et al. | |
| 6,718,194 B2 | 4/2004 | Kienzle | |
| 6,747,253 B1 * | 6/2004 | Firth ............... H05B 6/105 219/634 | |
| 6,807,446 B2 | 10/2004 | Fenn et al. | |
| 6,890,332 B2 | 5/2005 | Truckai et al. | |
| 6,991,655 B2 | 1/2006 | Iverson | |
| 7,001,346 B2 | 2/2006 | White | |
| 7,029,478 B2 | 4/2006 | Hollstien et al. | |
| 7,060,075 B2 * | 6/2006 | Govari ............... A61B 17/1707 606/98 | |
| D528,211 S | 9/2006 | Solar et al. | |
| 7,130,676 B2 | 10/2006 | Barrick | |
| 7,152,608 B2 | 12/2006 | Hunter et al. | |
| 7,217,276 B2 | 5/2007 | Henderson et al. | |
| 7,253,611 B2 | 8/2007 | Ma | |
| 7,294,133 B2 | 11/2007 | Zink et al. | |
| 7,295,184 B2 * | 11/2007 | Suprun ............... G01P 15/0888 156/157 | |
| 7,358,481 B2 | 4/2008 | Yeoh et al. | |
| 7,477,926 B2 | 1/2009 | McCombs | |
| 7,532,997 B2 | 5/2009 | Li et al. | |
| 7,542,791 B2 | 6/2009 | Mire et al. | |
| 7,549,960 B2 | 6/2009 | Govari | |
| 7,559,931 B2 | 7/2009 | Stone | |
| 7,575,550 B1 | 8/2009 | Govari | |
| 7,634,306 B2 | 12/2009 | Sarin et al. | |
| 7,686,818 B2 | 3/2010 | Simon et al. | |
| 7,702,379 B2 | 4/2010 | Avinash et al. | |
| 7,727,240 B1 | 6/2010 | Benton | |
| 7,729,742 B2 | 6/2010 | Govari | |
| 7,780,681 B2 | 8/2010 | Sarin et al. | |
| 7,785,330 B2 | 8/2010 | Sherman et al. | |
| 7,835,785 B2 | 11/2010 | Scully et al. | |
| 7,840,254 B2 | 11/2010 | Glossop | |
| 7,846,162 B2 | 12/2010 | Nelson et al. | |
| 7,918,853 B2 | 4/2011 | Watanabe | |
| 7,925,068 B2 | 4/2011 | Hoctor et al. | |
| 7,927,338 B2 | 4/2011 | Laffargue et al. | |
| 7,949,386 B2 | 5/2011 | Buly et al. | |
| 7,955,280 B2 | 6/2011 | Radinsky et al. | |
| 8,007,448 B2 | 8/2011 | Moctezuma | |
| 8,066,706 B2 | 11/2011 | Schlienger et al. | |
| 8,167,823 B2 | 5/2012 | Nycz et al. | |
| 8,176,922 B2 | 5/2012 | Sherman et al. | |
| 8,197,494 B2 | 6/2012 | Jaggi | |
| 8,211,108 B2 | 7/2012 | Matityahu | |
| 8,241,296 B2 | 8/2012 | Wasielewski | |
| 8,251,994 B2 | 8/2012 | McKenna et al. | |
| 8,301,262 B2 * | 10/2012 | Mi ........................ A61B 5/0031 607/30 | |
| 8,337,426 B2 | 12/2012 | Nycz | |
| 8,623,023 B2 | 1/2014 | Ritchey et al. | |
| 8,890,511 B2 | 11/2014 | Belew | |
| 8,997,362 B2 | 4/2015 | Briggs et al. | |
| 2002/0032445 A1 | 3/2002 | Fujiwara | |
| 2002/0052604 A1 | 5/2002 | Simon et al. | |
| 2002/0077540 A1 | 6/2002 | Kienzle | |
| 2002/0173792 A1 | 11/2002 | Severns et al. | |
| 2003/0105470 A1 | 6/2003 | White | |
| 2003/0120150 A1 | 6/2003 | Govari | |
| 2003/0135211 A1 | 7/2003 | Cho | |
| 2003/0153829 A1 | 8/2003 | Sarin et al. | |
| 2003/0164172 A1 | 9/2003 | Chumas et al. | |
| 2003/0208122 A1 | 11/2003 | Melkent et al. | |
| 2004/0011365 A1 | 1/2004 | Govari et al. | |
| 2004/0034355 A1 * | 2/2004 | Govari ............... A61B 17/1707 606/98 | |
| 2004/0097952 A1 | 5/2004 | Sarin et al. | |
| 2004/0147926 A1 | 7/2004 | Iversen | |
| 2004/0230199 A1 | 11/2004 | Jansen et al. | |
| 2004/0243148 A1 | 12/2004 | Wasielewski | |
| 2004/0254584 A1 | 12/2004 | Sarin et al. | |
| 2005/0027301 A1 | 2/2005 | Stihl | |
| 2005/0027304 A1 | 2/2005 | Leloup et al. | |
| 2005/0035115 A1 * | 2/2005 | Anderson ............... B29C 33/04 219/759 | |
| 2005/0035116 A1 * | 2/2005 | Brown ................... B29C 70/46 219/759 | |
| 2005/0043726 A1 | 2/2005 | McHale et al. | |
| 2005/0059885 A1 | 3/2005 | Melkent et al. | |
| 2005/0070916 A1 | 3/2005 | Hollstien et al. | |
| 2005/0075562 A1 | 4/2005 | Szakelyhidi et al. | |
| 2005/0075632 A1 | 4/2005 | Russell et al. | |
| 2005/0080335 A1 * | 4/2005 | Simon ................. A61B 17/1707 600/424 | |
| 2005/0080427 A1 | 4/2005 | Govari et al. | |

(56) References Cited

U.S. PATENT DOCUMENTS

| | | |
|---|---|---|
| 2005/0085714 A1 | 4/2005 | Foley et al. |
| 2005/0085715 A1 | 4/2005 | Dukesherer et al. |
| 2005/0099290 A1 | 5/2005 | Govari |
| 2005/0124988 A1 | 6/2005 | Terrill et al. |
| 2005/0143726 A1 | 6/2005 | Bortkiewicz |
| 2005/0148855 A1 | 7/2005 | Kienzle |
| 2005/0149050 A1 | 7/2005 | Stifter et al. |
| 2005/0197569 A1 | 9/2005 | McCombs |
| 2005/0228270 A1 | 10/2005 | Lloyd et al. |
| 2005/0242087 A1* | 11/2005 | Anderson ............... B29C 33/04 219/633 |
| 2005/0245821 A1 | 11/2005 | Govari et al. |
| 2005/0261700 A1 | 11/2005 | Tuma et al. |
| 2006/0015031 A1 | 1/2006 | Kienzle |
| 2006/0029186 A1 | 2/2006 | De Villiers et al. |
| 2006/0052782 A1 | 3/2006 | Morgan et al. |
| 2006/0074405 A1 | 4/2006 | Malackowski et al. |
| 2006/0084867 A1 | 4/2006 | Tremblay |
| 2006/0095047 A1 | 5/2006 | de la Barrera |
| 2006/0106400 A1 | 5/2006 | Fernandez et al. |
| 2006/0122541 A1 | 6/2006 | Tuma |
| 2006/0142656 A1 | 6/2006 | Malackowski et al. |
| 2006/0190011 A1 | 8/2006 | Ries |
| 2006/0264731 A1 | 11/2006 | Murphy |
| 2006/0282168 A1 | 12/2006 | Sherman et al. |
| 2006/0287613 A1 | 12/2006 | Amiot et al. |
| 2006/0293593 A1 | 12/2006 | Govari et al. |
| 2006/0293614 A1 | 12/2006 | Radinsky et al. |
| 2007/0093709 A1 | 4/2007 | Abernathie |
| 2007/0129629 A1 | 6/2007 | Beauregard et al. |
| 2007/0162018 A1 | 7/2007 | Jensen et al. |
| 2007/0167744 A1 | 7/2007 | Beauregard et al. |
| 2007/0191827 A1 | 8/2007 | Lischinsky et al. |
| 2007/0208251 A1* | 9/2007 | Anderson ............. A61M 25/01 600/424 |
| 2007/0219409 A1* | 9/2007 | Shimizu ............. A61B 1/00039 600/112 |
| 2007/0225595 A1 | 9/2007 | Malackowski et al. |
| 2007/0249967 A1 | 10/2007 | Buly et al. |
| 2007/0255132 A1 | 11/2007 | Shalgi et al. |
| 2007/0276370 A1 | 11/2007 | Altarac et al. |
| 2007/0282440 A1 | 12/2007 | Visentin |
| 2008/0015551 A1 | 1/2008 | Feine et al. |
| 2008/0021309 A1 | 1/2008 | Amiot et al. |
| 2008/0039857 A1 | 2/2008 | Giersch et al. |
| 2008/0051910 A1 | 2/2008 | Kammerzell et al. |
| 2008/0071142 A1 | 3/2008 | Gattani et al. |
| 2008/0086145 A1 | 4/2008 | Sherman et al. |
| 2008/0146969 A1 | 6/2008 | Kurtz |
| 2008/0154266 A1 | 6/2008 | Protopsaltis et al. |
| 2008/0221628 A1* | 9/2008 | Milbocker ....... A61B 17/00491 606/86 R |
| 2008/0228195 A1 | 9/2008 | von Jacko et al. |
| 2008/0255560 A1 | 10/2008 | Myers et al. |
| 2008/0269596 A1 | 10/2008 | Revie et al. |
| 2008/0281326 A1 | 11/2008 | Watanabe et al. |
| 2008/0281334 A1 | 11/2008 | Zheng et al. |
| 2009/0024023 A1* | 1/2009 | Welches ............... A61B 18/201 600/424 |
| 2009/0054910 A1 | 2/2009 | Zheng et al. |
| 2009/0088756 A1 | 4/2009 | Anderson |
| 2009/0099404 A1 | 4/2009 | Kraus et al. |
| 2009/0138019 A1 | 5/2009 | Wasielewski |
| 2009/0165573 A1* | 7/2009 | Ledoux ............... G01D 5/2033 73/862.626 |
| 2009/0177080 A1 | 7/2009 | Kristan et al. |
| 2009/0227862 A1 | 9/2009 | Smith et al. |
| 2009/0306665 A1 | 12/2009 | Lerner et al. |
| 2009/0306666 A1 | 12/2009 | Czartoski et al. |
| 2009/0326537 A1 | 12/2009 | Anderson |
| 2010/0041985 A1 | 2/2010 | Simon et al. |
| 2010/0063508 A1 | 3/2010 | Borja et al. |
| 2010/0064216 A1 | 3/2010 | Borja et al. |
| 2010/0069911 A1* | 3/2010 | Borja ................... A61B 17/157 606/88 |
| 2010/0076505 A1 | 3/2010 | Borja |
| 2010/0100011 A1 | 4/2010 | Roche |
| 2010/0137869 A1* | 6/2010 | Borja ................... A61B 17/157 606/88 |
| 2010/0137871 A1 | 6/2010 | Borja |
| 2010/0145337 A1 | 6/2010 | Janna et al. |
| 2010/0152566 A1 | 6/2010 | Rains et al. |
| 2010/0152573 A1* | 6/2010 | Ritchey .................... A61B 5/05 600/424 |
| 2010/0211177 A1 | 8/2010 | Abdou |
| 2010/0249657 A1* | 9/2010 | Nycz ..................... A61F 2/4609 600/587 |
| 2010/0261998 A1 | 10/2010 | Stiehl |
| 2010/0274121 A1* | 10/2010 | Ritchey .................... A61B 5/05 600/424 |
| 2010/0274253 A1 | 10/2010 | Ure |
| 2010/0274256 A1* | 10/2010 | Ritchey .................... A61B 5/05 606/96 |
| 2010/0274306 A1* | 10/2010 | Pastore ............. A61K 48/0083 607/3 |
| 2010/0289491 A1* | 11/2010 | Budker .................. G01R 33/26 324/304 |
| 2010/0312245 A1 | 12/2010 | Tipirneni et al. |
| 2011/0082366 A1 | 4/2011 | Scully |
| 2011/0109311 A1* | 5/2011 | Walsh .................... G01R 33/36 324/309 |
| 2011/0130765 A1 | 6/2011 | Fernandez et al. |
| 2011/0208037 A1 | 8/2011 | Rains et al. |
| 2011/0230886 A1* | 9/2011 | Gustilo ................ A61B 17/164 606/80 |
| 2011/0257518 A1 | 10/2011 | Buly et al. |
| 2011/0270080 A1 | 11/2011 | Crane |
| 2011/0288600 A1 | 11/2011 | Ritchey et al. |
| 2011/0295108 A1 | 12/2011 | Cox |
| 2011/0295253 A1 | 12/2011 | Bonutti et al. |
| 2012/0010500 A1* | 1/2012 | Couture ............... A61B 17/155 600/424 |
| 2012/0022406 A1 | 1/2012 | Hladio et al. |
| 2012/0029578 A1 | 2/2012 | Suh |
| 2012/0035468 A1 | 2/2012 | Ritchey et al. |
| 2012/0053585 A1 | 3/2012 | Nycz et al. |
| 2012/0091122 A1* | 4/2012 | Ahmad ..................... C21D 1/09 219/632 |
| 2012/0101361 A1* | 4/2012 | Rains .................... A61B 5/064 600/409 |
| 2012/0136402 A1 | 5/2012 | Burroughs |
| 2012/0143047 A1 | 6/2012 | Kimura |
| 2012/0184844 A1 | 7/2012 | Gielen |
| 2012/0209117 A1 | 8/2012 | Mozes et al. |
| 2012/0220107 A1* | 8/2012 | Fukuda ............. H01L 21/67757 438/478 |
| 2012/0226094 A1* | 9/2012 | Ritchey ............... A61B 17/1707 600/12 |
| 2012/0227542 A1* | 9/2012 | Koch ...................... B22D 41/01 75/10.12 |
| 2012/0232561 A1 | 9/2012 | Fernandez |
| 2012/0253354 A1* | 10/2012 | Arlettaz .............. A61B 17/1725 606/98 |
| 2012/0283599 A1* | 11/2012 | Borja ................... A61F 2/4657 600/587 |
| 2012/0330191 A1 | 12/2012 | Hulliger et al. |
| 2013/0018381 A1 | 1/2013 | Baumgartner |
| 2013/0079829 A1 | 3/2013 | Globerman et al. |
| 2013/0131679 A1* | 5/2013 | Janna ................. A61B 17/1707 606/62 |
| 2013/0218007 A1* | 8/2013 | Petteys .............. A61B 17/1728 600/424 |
| 2013/0238036 A1 | 9/2013 | Sinha |
| 2013/0289573 A1 | 10/2013 | Heilala et al. |
| 2014/0081121 A1 | 3/2014 | Wilhelm et al. |

(56) References Cited

U.S. PATENT DOCUMENTS

| | | | |
|---|---|---|---|
| 2015/0080893 | A1 | 3/2015 | Graca et al. |
| 2015/0245786 | A1 | 9/2015 | Lee et al. |

FOREIGN PATENT DOCUMENTS

| | | |
|---|---|---|
| CN | 201029876 | 3/2008 |
| DE | 102008023760 | 12/2009 |
| EP | 523905 | 5/1993 |
| EP | 628287 | 4/1995 |
| EP | 1391181 | 2/2004 |
| EP | 1570782 | 9/2005 |
| EP | 1382308 | 11/2005 |
| EP | 1803394 | 7/2007 |
| EP | 1570781 | 9/2009 |
| EP | 2130511 | 12/2009 |
| EP | 1563810 | 3/2010 |
| EP | 1743590 | 10/2010 |
| GR | 1005791 | 1/2008 |
| JP | 2004130094 A | 4/2004 |
| WO | WO9500085 | 1/1995 |
| WO | WO9713467 | 4/1997 |
| WO | WO9832387 | 7/1998 |
| WO | WO9947052 | 9/1999 |
| WO | WO0134016 | 10/2001 |
| WO | WO02062250 | 8/2002 |
| WO | WO03044556 | 5/2003 |
| WO | WO03073951 | 9/2003 |
| WO | WO03041611 | 12/2003 |
| WO | WO03105659 | 12/2003 |
| WO | WO2004030556 | 4/2004 |
| WO | WO2004001569 | 7/2004 |
| WO | WO2004069063 | 8/2004 |
| WO | WO2004091419 | 11/2004 |
| WO | WO2004112610 | 12/2004 |
| WO | WO2005023110 | 3/2005 |
| WO | WO2005084572 | 9/2005 |
| WO | WO2005087125 | 9/2005 |
| WO | WO2005120203 | 12/2005 |
| WO | WO2006060632 | 6/2006 |
| WO | WO2007009088 | 1/2007 |
| WO | WO2007025191 | 3/2007 |
| WO | WO2007061890 | 5/2007 |
| WO | WO2006094119 | 11/2007 |
| WO | WO2007133168 | 11/2007 |
| WO | WO2008105874 | 9/2008 |
| WO | WO2008106593 | 9/2008 |
| WO | WO2009046547 | 4/2009 |
| WO | WO2009108214 | 9/2009 |
| WO | WO2009131999 | 10/2009 |
| WO | WO2010011978 | 1/2010 |
| WO | WO2010028046 | 3/2010 |
| WO | WO2010099247 | 9/2010 |
| WO | WO2010111272 | 9/2010 |
| WO | WO2010124164 A1 | 10/2010 |
| WO | WO2010129141 | 11/2010 |
| WO | WO2010129308 | 11/2010 |
| WO | WO2011060536 | 5/2011 |
| WO | WO2011124661 | 10/2011 |
| WO | WO2012080840 | 6/2012 |
| WO | WO2013049534 | 4/2013 |

OTHER PUBLICATIONS

Patent Examination Report No. 1 for Australian Application No. 2015202388, mailed Mar. 2, 2016.
Office Action for Canadian Application No. 2,759,694, mailed Feb. 17, 2016.
Office Action for U.S. Appl. No. 12/547,716, mailed Sep. 18, 2012.
International Search Report and Written Opinion for International Application PCT/US2012/022481, mailed Jul. 31, 2012.
Office Action for U.S. Appl. No. 12/528,253, mailed Aug. 16, 2012.
Office Action for U.S. Appl. No. 13/123,792, mailed Sep. 14, 2012.
EKLIPTIK, Guiding Star, Lidis: The Best Solution for Distal Interlocking, 2008, 2 pages.
EKLIPTIK, "Guiding Star", reprinted from http://ekliptik.si/content/view/37/42, on Jul. 1, 2010, 2 pages.
"Innomed Hip Instruments—hohmann retractors," reprinted from http://www.innomed.net/hip_rets_hohmanns.htm on Jan. 6, 2011, 8 pages.
Office Action for European Application 08872996.7-1269, Jul. 21, 2011, 5 pages.
Office Action for U.S. Appl. No. 12/527,997, mailed Oct. 29, 2012.
Second Office Action for Chinese Application No. 200880006490.9 mailed Apr. 26, 2012.
Office Action for Australian Patent Application No. 2008221332, dated Jun. 15, 2012.
Notice of Reasons for Rejection for Japanese Application No. 2010-548660 mailed Jan. 15, 2013.
Office Action for U.S. Appl. No. 12/919,255, mailed Jan. 8, 2013.
Ex Parte Quayle Action in U.S. Appl. No. 29/376,026, mailed Apr. 30, 2012, 10 pages.
Office Action for U.S. Appl. No. 13/030,801, mailed Mar. 13, 2013.
Office Action for U.S. Appl. No. 13/323,010, mailed Aug. 14, 2012.
Office Action for U.S. Appl. No. 12/768,689, mailed Nov. 14, 2012.
Office Action for U.S. Appl. No. 12/768,689, mailed Jun. 5, 2012.
Notice of Reasons for Rejection for Japanese Application No. 2012-508518 mailed Dec. 10, 2013.
Office Action in Russian Application No. 2011146914, mailed Dec. 16, 2013.
Notice of Reasons for Rejection for Japanese Application No. 2012-508611, mailed Jan. 28, 2014.
International Search Report and Written Opinion for International Application No. PCT/US2010/032634, mailed Jan. 26, 2011, 10 pages.
Rains, et al., U.S. Appl. No. 12/919,255, filed Aug. 25, 2010.
International Search Report for International Application No. PCT/US2008/055300, mailed Sep. 17, 2008, 3 pages.
International Preliminary Report on Patentability and Written Opinion for International Application No. PCT/US2007/063001, mailed Sep. 1, 2009, 5 pages.
International Search Report for International Application No. PCT/US2007/063001, mailed Nov. 30, 2007, 3 pages.
European Search Report for European Application No. 07830964.7, mailed Jun. 18, 2010, 4 pages.
International Preliminary Report on Patentability and Written Opinion for International Application No. PCT/US2008/055300, mailed Sep. 1, 2009, 6 pages.
Ritchey, et al., U.S. Appl. No. 29/376,026, filed Sep. 30, 2010.
International Search Report and Written Opinion for PCT/US2010/030784, mailed Oct. 29, 2010, 11 pages.
International Search Report for International Application No. PCT/US2008/074520, mailed Jan. 23, 2009, 2 pages.
Office Action for Chinese Application No. 200880006490.9, mailed Mar. 31, 2011, 13 pages.
Office Action for Russian Application No. 2011146669/14 mailed Apr. 3, 2014.
Office Action for U.S. Appl. No. 13/358,065, mailed Jun. 3, 2014.
Office Action for U.S. Appl. No. 13/323,010, mailed Jun. 4, 2013.
Office Action for U.S. Appl. No. 12/527,997, mailed May 21, 2013.
International Search Report and Written Opinion for International Application No. PCT/US2012/041613, mailed Feb. 15, 2013.
International Search Report and Written Opinion for International Application No. PCT/US2010/051678, mailed Apr. 14, 2011, 8 pages.
First Office Action for Chinese Application No. 201080028779.8 mailed May 23, 2014.
Office Action for U.S. Appl. No. 12/768,689, mailed Jul. 9, 2014.
International Search Report and Written Opinion for International Application No. PCT/US2013/027042, mailed Jun. 12, 2013.
Communication Pursuant to Article 94(3) EPC for European Application No. 07757660.1, mailed Jun. 5, 2013.
Decision of Rejection for Japanese Application No. 2009-551851, mailed Jun. 11, 2013.
Communication Pursuant to Article 94(3) EPC for European Application No. 08730964.7, mailed Jun. 6, 2013.

(56) References Cited

OTHER PUBLICATIONS

Office Action for U.S. Appl. No. 13/123,792, mailed Jul. 2, 2013.
Office Action for U.S. Appl. No. 12/528,253, mailed Mar. 21, 2012, 9 pages.
Office Action for U.S. Appl. No. 12/547,716, mailed Apr. 2, 2012, 11 pages.
First Office Action for Chinese Application No. 200880128908.3 mailed Apr. 24, 2012.
Association of Surgical Technologists, "AST Recommended Standards of Practice for Surgical Drapes," effective Apr. 13, 2008.
Ashar, Tom, "Ultrasound Guidance for Placement of Central Venous Catheters," Israeli Journal of Emergency Medicine, vol. 7, No. 2, Jun. 2007.
Buckner, C., et al., "Real-Time Sonography wth Electromagnetic Tracking Navigation for Biopsy of a Hepatic Neoplasm Seen on on Arterial Phase Computed Tomography," J Ultrasound Med 2011, 30:253-256.
"GE Heathcare: Ultrasound Imaging Accessories, vol. 6," CIVco Medical Solutions, Multi-Modality Imaging, 2011.
"Guiding Star with the LIDIS module," Ekliptik, 2007.
Ekliptik, LIDIS module, brochure, 2010.
Brochure for GE Healthcare Drapes and Sterile Covers, accessed on Jun. 21, 2012, at http://www.gehealthcare.com/usen/xr/surgery/docs/SurgeryDrapes&Film.pdf.
Ekliptik, "User Manual: Guiding Star/LIDIS," Jun. 16, 2010, reprinted from http://www.ekliptik.si/html/downloads/documents/manuals/LIDIS_user_manual.pdf.
Medtronic, "Orthopaedic Navigation Soluations," 2005, reprinted from http://behzadisportsdoc.com/wordpress/wp-content/uploads/2011/05/medtronic_orthonavsolutions.pdf.
GE Healthcare, "Interventional X-ray, OEC C-arm," 2012.
Office Action for U.S. Appl. No. 12/919,255, mailed May 25, 2012.
Extended European Search Report for European Application No. 128003282, mailed May 27, 2015.
Canadian Office Action for Application No. 2,678,369, mailed Sep. 4, 2015.
Notice of Reasons for Rejection in Japanese Application 2014-249827, mailed Oct. 5, 2015.
Office Action for U.S. Appl. No. 14/114,940, mailed Mar. 30, 2016.
Office Action for U.S. Appl. No. 13/323,010, mailed Jan. 19, 2016.
Office Action in Canadian Application No. 2,759,694, mailed Feb. 17, 2016.
Second Office Action for Chinese Application No. 201080028779.8 mailed Apr. 10, 2015.
Office Action for Canadian Application No. 2,777,468, mailed Jan. 19, 2016.
Office Action for Canadian Application No. 2,777,468, mailed Nov. 25, 2016.

* cited by examiner

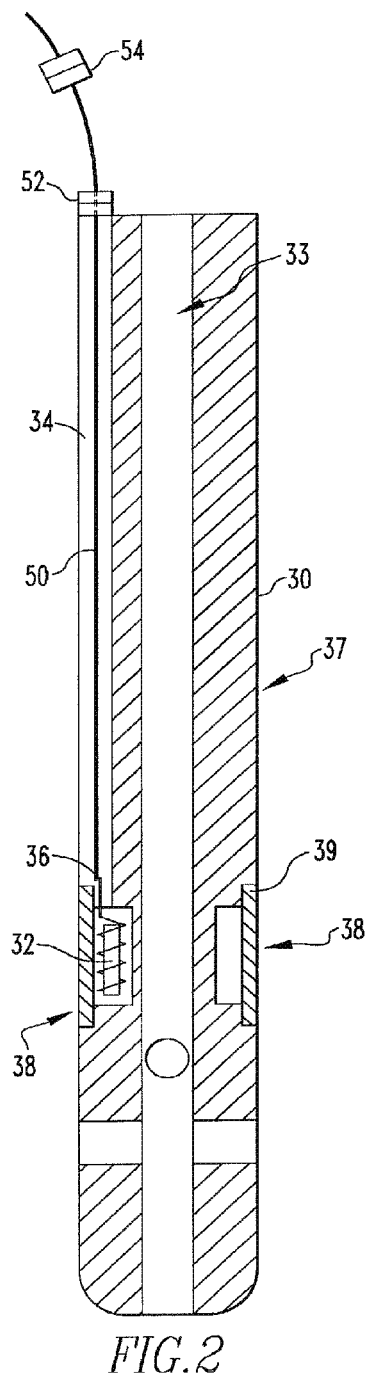
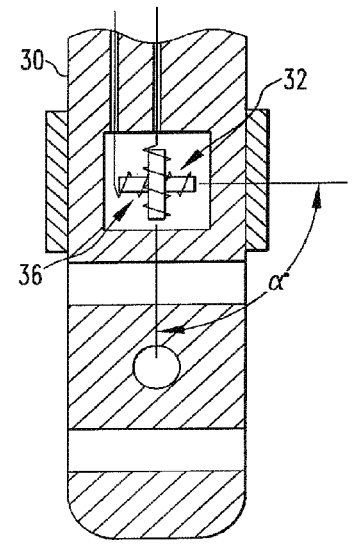
FIG.3
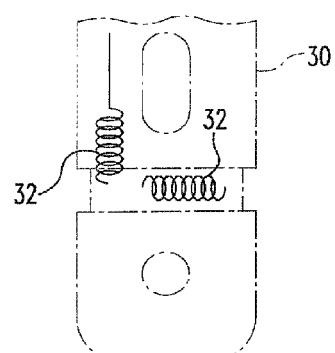
FIG.4
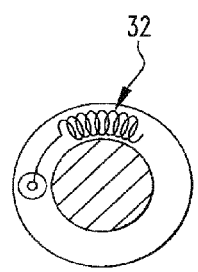
FIG.5
FIG.2

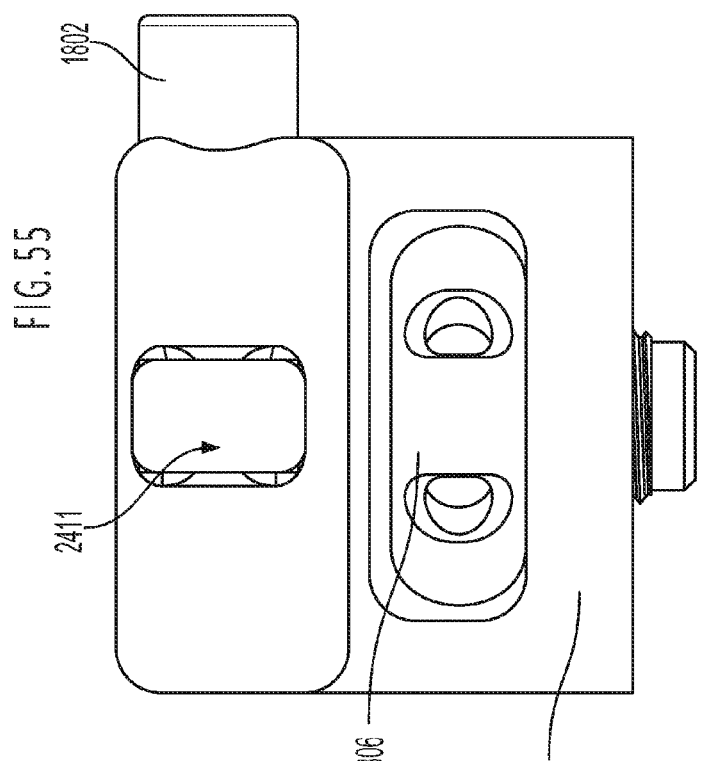
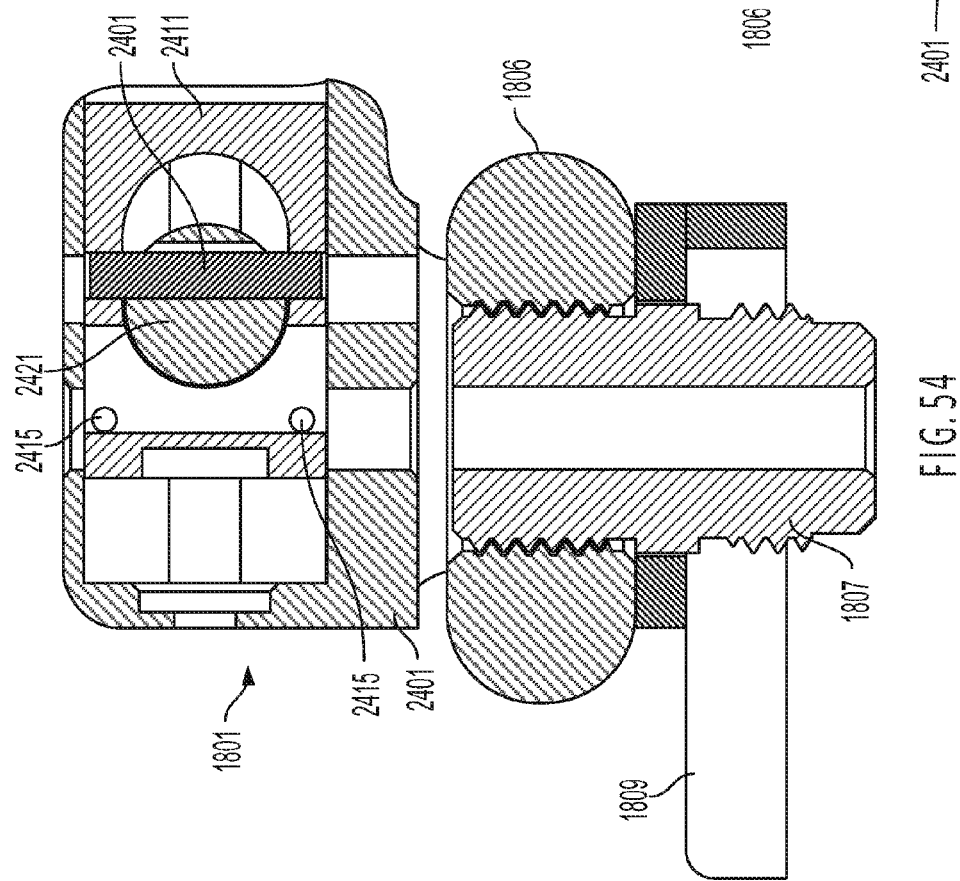

TARGETING AN ORTHOPAEDIC IMPLANT LANDMARK

CROSS REFERENCE TO RELATED APPLICATIONS

This application is a continuation of U.S. patent application Ser. No. 12/758,747, filed Apr. 12, 2010, now allowed, which is a continuation-in-part of U.S. application Ser. No. 12/547,716, filed Aug. 26, 2009, now U.S. Pat. No. 8,784, 425, issued Jul. 22, 2014, and claims priority to U.S. Provisional Application No. 61/173,069, filed on Apr. 27, 2009. The entire contents of prior application Ser. No. 12/758,747 and U.S. Provisional Application No. 61/173, 069 are incorporated herein by reference.

BACKGROUND

Technical Field

This disclosure relates to identification of blind landmarks on orthopaedic implants.

Description of the Related Art

The interlocking nail has significantly widened the scope for intramedullary (IM) fixation of long bone fractures. Anchoring an IM nail to a bone makes the construct more stable longitudinally and stops rotation of the nail within the bone. A typical IM nail fixation surgery involves a combination of jigs, x-ray imaging, and manual "eye-balling" to locate and drill the distal screw holes and to install the screws in the screw holes.

In IM nail fixation surgery, an IM nail is inserted into the canal of a fractured long bone in order to fixate the fractured ends together. Typically, the proximal locking is performed first and is usually carried out with a jig. Nail deformation during intramedullary insertion, however, may make a jig inaccurate for the distal screws. In fact, the positioning of the distal locking screws and alignment of the drill for the drilling of the distal screw holes is the most time consuming and challenging step of the implantation procedure. The two main reasons for failure in distal locking are (1) incorrect entry point on the bone and (2) wrong orientation of the drill. If either of these problems occurs, then the drill will not go through the nail hole. An inaccurate entry point also compounds the problem as the rounded end of the drill bit often slips, damaging healthy bone rendering it difficult to place another drill hole next to the inaccurate hole. Inaccurate distal locking may lead to premature failure with breakage of the nail through the nail hole, breakage of the screw, or the breaking of the drill bit within the bone.

Manual techniques are the most common and accepted techniques for sighting the distal screw holes. The majority of manual distal targeting techniques employ a guide bushing or cylindrical sleeve that guides the drill. The mechanisms of aligning the guide bushing and keeping it in place differ. There are cases where the surgeons use a guide bushing cut in half longitudinally or a full guide bushing to help steady the drill bit. In either situation, the surgeon will incise the patient and insert the drill through the incision. Manual techniques are based primarily on the surgeon's manual skill and make use of radiographic x-ray imaging and mechanical jigs.

Another method for achieving this on long nails is by using a technique called "perfect circles" with the aid of a C-shaped arm. This is where the patient and the C-arm are oriented such that when viewing the implant fluoroscopically the hole through which the screw is to pass appears to be in the shape of a circle. If the C-arm is not perpendicular to the hole then the hole appears oblong or even absent.

A need exists for an improved system and method for accurately and dependably targeting landmarks of a medical implant. Further, a need exists for accurately positioning the distal locking screws and aligning the drill for the drilling of the distal screw holes. Still further, a need exists for an improved system for targeting landmarks whereby the components may be easily sterilized or autoclaved and reused again.

SUMMARY

In a general aspect, a system for identifying a landmark includes a field generator for generating an electromagnetic field and a landmark identifier. The field generator and the landmark identifier are disposed in a common housing, and the field generator, the landmark identifier, and the common housing are autoclavable. The system also includes an orthopaedic implant located within the electromagnetic field, and the orthopaedic implant includes at least one landmark. A first magnetic sensor is spaced apart from the at least one landmark by a set distance, and a processor compares sensor data from the first sensor and landmark identifier and uses the set distance to calculate the position of the landmark identifier relative to the at least one landmark.

Implementations may include one or more of the following features. For example, the landmark is selected from the group consisting of a structure, a hole, a void, a boss, a channel, a detent, a flange, a groove, a member, a partition, a step, an aperture, a bore, a cavity, a dimple, a duct, a gap, a notch, an orifice, a passage, a slit and a slot. The orthopaedic implant may be an intramedullary nail. The orthopaedic implant has an outer surface and an inner surface forming a cannulation, and the first sensor is mounted to a distal portion of a probe that extends into the cannulation. The common housing in some implementations also accommodates a drill motor, the drill motor being coupleable to a drill bit. The housing may include a drill sleeve. The housing may be disk-shaped. The drill extends normally outward from the disk-shaped housing. The system can also include an insertion handle removably coupled to the orthopaedic implant. An adjustable stop can be coupled to the implant and includes a slot through which the probe extends. The adjustable stop includes a clamp mechanism to hold the probe in a fixed position. The probe may include a plurality of spaced apart markings, and the adjustable stop includes a clamp mechanism to hold the probe in a fixed position on a marking or between two markings.

In another general aspect, identifying a landmark includes providing an orthopaedic implant assembly having an orthopaedic implant having at least one landmark, implanting the orthopaedic implant assembly in a patient, and placing a probe in the implant. The probe includes an electromagnetic sensor. Identifying the landmark further includes generating an electromagnetic field that encompasses the sensor and landmark, identifying the at least one landmark using a landmark identifier, installing a transfixion element in the at least one landmark, and removing the probe. The landmark identifier is disposed in an autoclavable housing.

Implementations may include one or more of the following features. For example, the landmark is selected from the group consisting of a structure, a hole, a void, a boss, a channel, a detent, a flange, a groove, a member, a partition, a step, an aperture, a bore, a cavity, a dimple, a duct, a gap, a notch, an orifice, a passage, a slit and a slot. The orthopaedic implant may be an intramedullary nail. The orthopaedic implant has an outer surface and an inner surface forming a cannulation, and identifying a landmark further includes mounting the first sensor to a distal portion of a probe that extends into the cannulation. The field generator and landmark identifier are disposed in a common autoclavable housing and identifying the landmark also includes autoclaving the housing. The field generator and landmark identifier are disposed in a common autoclavable housing that may also accommodates a drill motor, the drill motor being coupled to a drill bit, and identifying a landmark further comprises autoclaving the housing and drill. The housing may include a drill sleeve. The housing may be disk-shaped. Identifying a landmark also includes removably coupling an insertion handle to the orthopaedic implant and/or clamping the probe in a fixed position. The probe comprises a plurality of spaced apart markings and the probe is clamped in a fixed position on a marking or between two markings.

In another general aspect, a system for identifying a landmark includes an autoclavable housing accommodating a field generator for generating an electromagnetic field, a landmark identifier, and a drill motor. An orthopaedic implant is located within the electromagnetic field and the orthopaedic implant has at least one landmark. A probe includes a first electromagnetic sensor and is placed within the orthopaedic implant and spaced apart from the at least one landmark by a set distance. A processor is also included for comparing sensor data from the first sensor and landmark identifier and for using the set distance to calculate the position of the landmark identifier relative to the at least one landmark. The first electromagnetic sensor is coupled to the processor via the probe.

In another general aspect, a kit for identifying landmarks on medical implants includes an autoclavable housing accommodating a field generator for generating an electromagnetic field, and a landmark identifier. A plurality of orthopaedic implants are also included, one of which is located within the electromagnetic field. Each orthopaedic implant includes at least one landmark. A plurality of probes, each including an electromagnetic sensor, is included. One of the probes selected based on a size of the implant disposed in the electromagnetic field. The selected probe is placed within the implant in the electromagnetic field and spaced apart from the at least one landmark by a set distance. A processor is included for comparing sensor data from the first sensor and landmark identifier and for using the set distance to calculate the position of the landmark identifier relative to the at least one landmark, wherein the first electromagnetic sensor is coupled to the processor via the probe.

In another general aspect, a system for targeting a landmark of an orthopaedic implant includes an autoclavable housing, a field generator disposed within the housing for generating an electromagnetic field, a first electromagnetic sensor for disposition at a set distance from the landmark that generates sensor data in response to the generated electromagnetic field, and an element removably coupled to the housing, the element defining a longitudinal axis that represents one axis of the generated magnetic field. The system is configured to use the one axis of the generated electromagnetic field to determine the position of the element relative to the landmark.

Implementations may include one or more of the following features. For example, the system can include a first probe having a proximal portion and a distal portion, the first electromagnetic sensor disposed on the distal portion of the probe, a retractable probe including the first electromagnetic sensor, or a retractable probe including the first electromagnetic sensor and a housing containing at least a portion of the retractable probe. A second electromagnetic sensor disposed on the proximal portion of the first probe can also be included. The system can include a second probe having a proximal and a distal portion and a third electromagnetic sensor disposed on the distal end of the second probe, where the second probe is longer than the first probe. The system can also include a processor for comparing the sensor data from the first electromagnetic sensor and the element and using the set distance to calculate the position of the element relative to the landmark. The system can include an adjustable stop that is connectable to the orthopedic implant. The adjustable stop can include a slot through which the first or the second probe extends and includes a clamping mechanism to hold the first or second probe in a fixed position. The first or the second probe can include a plurality of spaced apart indicators such that the clamping mechanism can be selectively set to hold the first or second probe in a fixed position at an indicator or between indicators. A handle can be removably coupled to the orthopedic implant. The autoclavable housing can be disk-shaped. The element can include one of a drill guide, a drill sleeve, a drill, a drill nose, a drill barrel, a drill chuck, and a fixation element. The orthopedic implant can include one of an intramedullary nail, a bone plate, a hip prosthetic, a knee prosthetic, a spinal prosthetic, and a shoulder prosthetic. The first or the second probe can be coiled or bent prior to placement into the orthopedic implant. The first electromagnetic sensor includes a proximal end and a distal end. The distal end of the first electromagnetic sensor is connected to a proximal end of the orthopedic implant such that the first electromagnetic sensor is spaced apart a set distance from at least one landmark disposed in a proximal region of the orthopedic implant. At least the housing and the element are reusable. The housing is made from one of ceramic, silicone, polypropylene (PP), polycarbonate (PC), polymethylpentene (PMP), PTFE resin, or polymethyl methacrylate (PMMA or acrylic).

In another general aspect, an apparatus for targeting a landmark of an orthopaedic implant includes an insertion handle removably attachable to the orthopaedic implant, an adjustable stop comprising an actuator, and a probe comprising a sensor and a plurality of markings to assist in placing the probe and sensor at a desired location with respect to the orthopaedic implant.

Implementations may include one or more of the following features. For example, the adjustable stop includes a mating portion such that when the stop is connected to the insertion handle, the stop is located or fixed within three degrees of freedom. The insertion handle is attached to the orthopaedic implant through use of a cannulated bolt.

In another general aspect, a kit for targeting a landmark of an orthopaedic implant includes a proximal targeting probe comprising a tape body and a sensor included within or on the tape body at a predetermined distance from a reference point of the tape body. The proximal targeting probe includes a first indicator that indicates that the proximal targeting probe is to be used for targeting proximal landmarks of an orthopaedic implant. The kit also includes a distal targeting probe that includes a tape body that is longer than the tape body of the proximal targeting probe and a sensor included within or on the tape body of the distal targeting probe at a second predetermined distance from a second reference point of the target body of the distal targeting probe. The distal targeting probe includes a second indicator that indicates that the distal targeting probe is to be used for targeting distal landmarks of the orthopaedic implant.

Implementations may include one or more of the following features. For example, the first indicator includes a color-coded grip and the second indicator includes a color-coded grip that is a different color than the first indicator. The first indicator includes a color-coded grip and the second indicator includes a color-coded grip that is a different color than the first indicator. The proximal targeting probe includes a cable for carrying a signal from the sensor included within or on the tape body of the proximal targeting probe to a control unit, and the distal targeting probe includes a second cable for carrying a second signal from the sensor included within or on the tape body of the distal targeting probe to the control unit. The sensors included within or on the tape bodies of the proximal and distal targeting probes are connected to one or more Programmable Read-Only Memory microchip that identifies whether the proximal and distal targeting probes are used for proximal or distal targeting. The tape bodies of the proximal and distal targeting probes include one or more bends to bias at least a portion of the tape bodies against a wall of the orthopaedic implant.

In another general aspect, a probe for use in targeting a landmark of an orthopaedic implant includes a housing, a retractable or extensible body disposed within the housing. The body is configured to form a generally straight shape when extended from the housing. A sensor is disposed within the body and is positionable at a first location for targeting a proximal landmark of the orthopaedic implant. The sensor is positionable at a second location for targeting a distal landmark of the orthopaedic implant. The body comprises one of layered, flexible stainless steel spring bands, resilient plastics, or rubber tubing or sheeting. The body includes a plurality of nested segments of tubing that can extend and retract by sliding within adjacent tubing segments.

In another general aspect, an apparatus for targeting a landmark located in a proximal end of an orthopaedic implant includes an insertion handle and a sensor disposed within or on the insertion handle at a predetermined distance from a proximal locking aperture formed in the orthopaedic implant when the insertion handle is attached to the orthopaedic implant. The sensor is passive or electrically powered. The sensor is mounted in a housing that is unitary or integral with the insertion handle.

The disclosed methods and apparatuses include several advancements. First, the disclosed methods and apparatuses can operate independently of fluoroscopy and eliminate the necessity of X-ray devices for targeting of transfixion elements, thereby reducing the exposure of users and patients to radiation. Second, disclosed methods and apparatuses allow a user to lock the driving-end of the implant before locking the non-driving end of the implant. In other words, the disclosed methods and apparatuses do not require use of an implant cannulation that requires proximal locking prior to distal locking.

Other advantages and features will be apparent from the following detailed description when read in conjunction with the attached drawings.

BRIEF DESCRIPTION OF THE DRAWINGS

FIG. 2 is a sectional view of an orthopaedic implant of FIG. 1.
FIG. 3 is a partial sectional of the implant of FIGS. 1 and 2 illustrating the sensor mounting.
FIG. 4 is a partial sectional view of another sensor mounting in an implant.
FIG. 5 is a sectional view of the sensor and implant illustrated in FIG. 4.

FIGS. 53-62 are illustrations of adjustable stops.

It should be understood that the drawings are not necessarily to scale and that the disclosed implementations are sometimes illustrated diagrammatically and in partial views. In certain instances, details which are not necessary for an understanding of the disclosure or which render other details difficult to perceive may have been omitted. It should be understood, of course, that this disclosure is not limited to the particular implementations illustrated herein.

DETAILED DESCRIPTION

Figure 1:
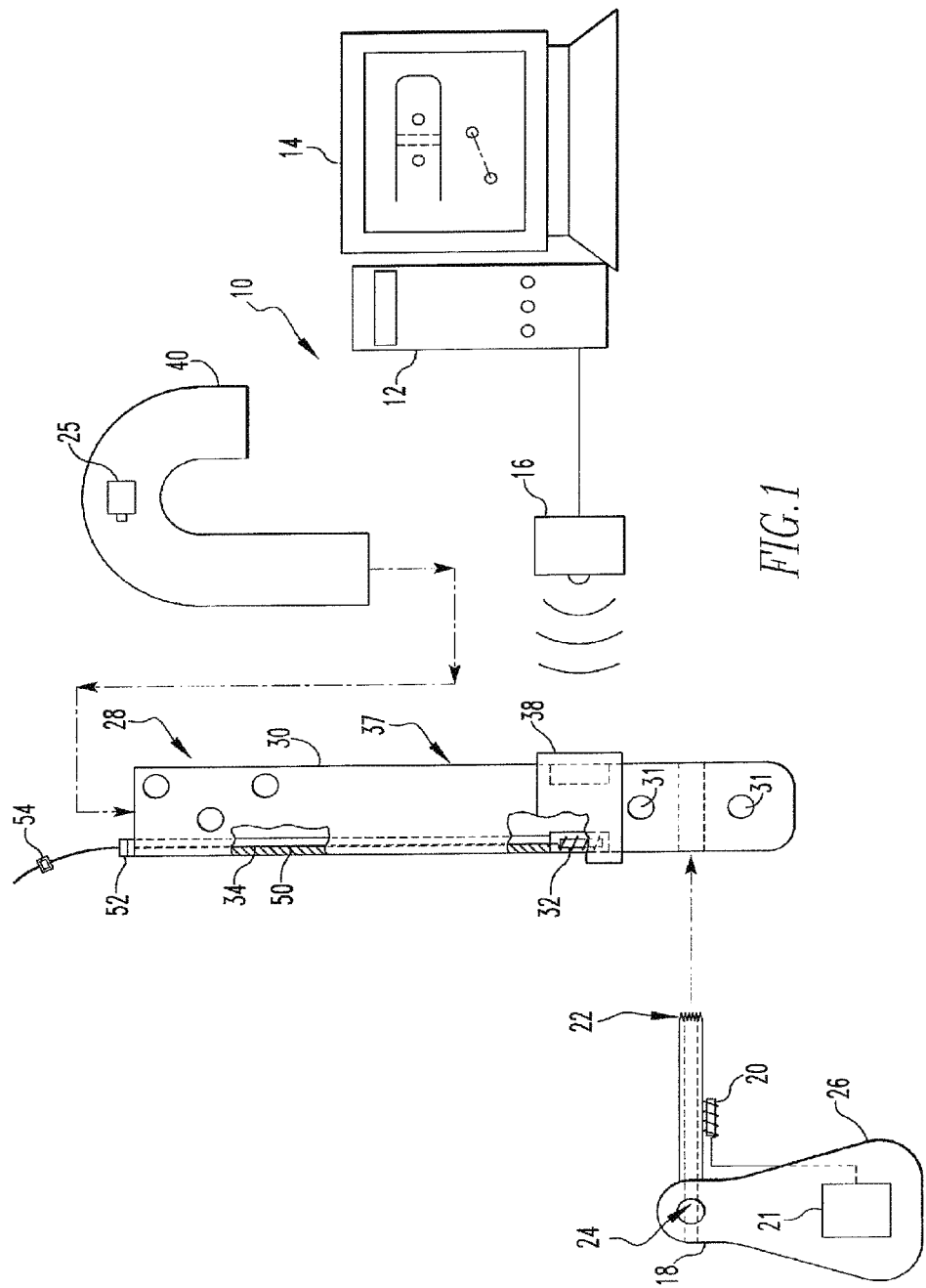
FIG. 1 illustrates a system for identifying a landmark.

Referring to the accompanying drawings in which like reference numbers indicate like elements, FIG. 1 illustrates one disclosed system 10 for identifying a landmark. The system 10 may include a processor 12, a magnetic field generator 16, a landmark identifier 18, and an orthopaedic implant assembly 28. The system 10 may also include a monitor 14 electrically connected to the processor 12 and an insertion handle 40 removably attached to the orthopaedic implant assembly 28. The processor 12 is depicted as a desktop computer in FIG. 1 but other types of computing devices may be used. As examples, the processor 12 may be a desktop computer, a laptop computer, a personal data assistant (PDA), a mobile handheld device, or a dedicated device. The magnetic field generator 16 is a device available from Ascension Technology Corporation of 107 Catamount Drive, Milton Vt., U.S.A.; Northern Digital Inc. of 103 Randall Drive, Waterloo, Ontario, Canada; or Polhemus of 40 Hercules Drive, Colchester Vt., U.S.A. Of course, other generators may be used. As examples, the field generator 16 may provide a pulsed direct current electromagnetic field or an alternating current electromagnetic field. The system 10 may also include a control unit (not shown) connected to the magnetic field generator 16. The control unit controls the field generator 16, receives signals from small mobile inductive sensors, and communicates with the processor 12, either by wire or wirelessly. The control unit may be incorporated into the processor 12 either through hardware or software.

The system 10 is a magnetic position tracking system. For illustrative purposes, the system 10 may include a magnetic field generator 16 comprised of suitably arranged electromagnetic inductive coils that serve as the spatial magnetic reference frame (i.e., X, Y, Z). The system 10 may also include small mobile inductive sensors, which are attached to the object being tracked. It should be understood that other variants could be easily accommodated. The position and angular orientation of the small mobile inductive sensors are determined from its magnetic coupling to the source field produced by magnetic field generator 16.

It is noted that the magnetic field generator 16 generates a sequence, or set, of here six, different spatial magnetic field shapes, or distributions, each of which is sensed by the small mobile inductive sensors. Each sequence enables a sequence of signals to be produced by the small mobile inductive sensors. Processing of the sequence of signals enables determination of position and/or orientation of the small mobile inductive sensors, and hence the position of the object to which the small mobile inductive sensor is mounted relative the magnetic coordinate reference frame which is in fixed relationship to the magnetic field generator 16. The processor 12 or the control unit may use the reference coordinate system and the sensed data to create a transformation matrix comprising position and orientation information.

The landmark identifier 18 is used to target a landmark, such as a landmark on the orthopaedic implant assembly 28. The landmark identifier 18 may include one or more small mobile inductive sensors or may include the field generator. The landmark identifier 18 has a second sensor 20. The landmark identifier 18 may be any number of devices. As examples, the landmark identifier may be a device that includes a structure that provides a user with an understanding of the location and orientation of a hidden landmark. For example, the landmark identifier can include a drill guide, a drill sleeve, a drill, a drill nose, a drill barrel, a drill chuck, or a fixation element. In some implementations, the structure can be a housing having an opening, or other structure that indicates the location and orientation of a landmark. In FIG. 1, the landmark identifier 18 is a drill sleeve and includes a sensor 20, whereas in FIG. 39, the landmark identifier 2016 includes a housing 2020 having a central aperture and includes a magnetic field generator (not shown) in the housing 2020. The landmark identifier 18 may include one or more of a serrated tip 22, a tube 24, and a handle 26. The tube 24 also may be referred to as a bushing, cylinder, guide, or drilling/screw placement guide. The second sensor 20 is oriented relative to an axis of the tube 24. The tube 24 may receive a drill. This offset of the sensor 20 from the tube 24 allows the position and orientation of the tube to be located in space in six dimensions (three translational and three angular) relative to the magnetic field generator 16 and/or another sensor in the system. The processor 12 may need to be calibrated to adjust for the offset distance of the second sensor 20. The landmark identifier 18 and the field generator 16 may be combined into a single component. For example, the field generator 16 may be incorporated within the handle 26.

The orthopaedic implant assembly 28 may include an implant 30 and one or more small mobile inductive sensors. The orthopaedic implant assembly 28 includes a first sensor 32. In FIG. 1, the implant 30 is in the form of intramedullary nail but other types of implants may be used. As examples, the implant may be an intramedullary nail, a bone plate, a shoulder prosthetic, a hip prosthetic, or a knee prosthetic. The first sensor 32 is oriented and in a predetermined position relative to one or more landmarks on the implant 30. As examples, the landmark may be a structure, a void, a boss, a channel, a detent, a flange, a groove, a member, a partition, a step, an aperture, a bore, a cavity, a dimple, a duct, a gap, a notch, an orifice, a passage, a slit, a hole, or a slot. In FIG. 1, the landmarks are transfixion holes 31. The offset of the first sensor 32 from the landmark allows the position of the landmark to be located in space in six dimensions (three translational and three angular) relative to the magnetic field generator 16 or another sensor in the system, such as the second sensor 32. The processor may need to be calibrated to adjust for the offset distance of the first sensor 32.

The first sensor 32 and the second sensor 20 are coupled to the processor 12. This may be accomplished by wire or wirelessly. The first sensor 32 and the second sensor 20 may be a six degree of freedom sensor configured to describe the location of each sensor in three translational axes, generally called X, Y and Z and three angular orientations, generally called pitch, yaw and roll. By locating the sensor in these reference frames, and knowing the location and orientation of each sensor, the landmark identifier 18 may be located relative to the landmark on the implant 30. In one particular implementation, the information from the sensors allows for a surgeon to plan the surgical path for fixation and properly align a drill with a blind fixation hole 31. The sensors 32, 20 are six degrees of freedom sensor from Ascension Technology Corporation of 107 Catamount Drive, Milton Vt., U.S.A.; Northern Digital Inc. of 103 Randall Drive, Waterloo, Ontario, Canada; or Polhemus of 40 Hercules Drive, Colchester Vt., U.S.A. Of course, other sensors may be used.

The first sensor 32 may be attached to the implant 30. For example, the first sensor 32 may be attached to an outer surface 37. In FIG. 1, the implant 30 may also include a groove 34 and a pocket 36 (best seen in FIG. 2). The groove 34 and pocket 36 are located in a wall of the implant 30. The first sensor 32 is intended to be attached to the implant 30 and installed in a patient for the service life of the implant 30. Further, the orthopaedic implant assembly 28 may include a cover 38 to cover the pocket 36 and/or the groove 34. The cover 38 may be substantially flush with the external surface 37 of the implant 30. Accordingly, the implant 30 may include a second opening 39 (see FIG. 2) to receive the cover 38.

The first sensor 32 may be tethered to leads for communication and power. The leads, and the sensor, may be fixed to the implant 30. A lead 50 may be used to connect the first sensor 32 to the processor 12 or the control unit. The lead 50 may be made from biocompatible wire. As an example, the lead 50 may be made of DFT wire available from Fort Wayne Metals Research Products Corp., 9609 Indianapolis Road, Fort Wayne, Ind. 46809. DFT is a registered trademark of Fort Wayne Metals Research Products Corp. A first connector 52 may be used to place the lead 50 relative to the implant 30. A second connector 54 may be used to connect the lead 50 to another device, such as the processor 12, the control unit, or the insertion handle 40.

The first sensor 32 may be fixed in the pocket 36 using a range of high stiffness adhesives or polymers including epoxy resins, polyurethanes, polymethyl methacrylate, polyetheretherketone, UV curable adhesives, silicone, and medical grade cyanoacrylates. As an example, EPO-TEK 301 available from Epoxy Technology, 14 Fortune Drive, Billerica, Mass. 01821 may be used. The lead 50 may be fixed in the groove in a similar manner. These types of fixation methods do not adversely affect the performance of the electrical components. Thereafter, the cover 38 may be placed on the implant 30 and welded in-place. For example, the covers may be laser welded to the implant.

The monitor 14 may be configured to display the position and orientation of the first sensor 32 and the second sensor 20 so that the display may show a surgeon both sensor positions and orientations relative to one another. The processor 12 may send positional data, either by wire or wirelessly, to a user interface, which may graphically display the relative positions of the landmark identifier and the implant on the monitor. The view displayed on the monitor 14 may be oriented relative to the landmark identifier so that the surgeon may visualize the user interface as an extension of the landmark identifier. The user interface also may be oriented so that the surgeon may view the monitor simultaneously with the surgical field.

The insertion handle 40 may be used for installation of the orthopaedic implant assembly 28 and also may be used to route the leads from the first sensor 32. For example, the insertion handle 40 may route both communication and power leads between the implant 30 and the processor 12.

In FIG. 1, the landmark identifier 18 and the insertion handle 40 each include a communications module 21, 25 for wirelessly transmitting data from the sensor 20, 32 to the processor 12, but those skilled in the art would understand that other methods, such as by wire, may be used. The second connector 54 plugs into the communications module 25. Alternatively, and as is explained in greater detail below, the implant 30 and the insertion handle 40 may have mating electrical contacts that form a connection when the components are assembled such that the first sensor 32 is connected to the communications module 25.

The implant 30 may include a communications circuit and an antenna for wireless communication. Power for the first sensor 32 and/or the communications circuit may be positioned within the insertion handle 40. For example, a battery may be placed within the insertion handle 40 for transferring power to the first sensor 32 and/or other electronics. Alternatively, the communications circuit, the antenna, and the battery may be located within the insertion handle 40 and each of these may be tethered to the first sensor 32. In yet another implementation, the implant 30 may include a coil to inductively power the communications circuit and communicate data from the first sensor 32. The power source may be a single source mode or may be a dual mode AC/DC.

In use, the orthopaedic implant assembly 28 is installed in a patient. For example, in the case of internal fixation, the intramedullary nail is placed within an intramedullary canal. Optionally, the user may use transfixion elements, such as screws, to first lock the proximal end of the intramedullary nail. An operator uses the targeting device 18 and the first sensor 32 to identify the landmarks. For example, in the case of intramedullary nail fixation, a surgeon uses the targeting device 18 to identify the blind transfixion holes 31 and drill through the holes 31 for placement of a transfixion element.

FIG. 2 further illustrates the implant 30 as illustrated in FIG. 1. The implant 30 may include the first sensor 32, the longitudinal groove 34, the pocket 36, the cover 38, and the second opening 39. As examples, the cover 38 may be comprised of gold or titanium foil. The implant 30 may include an inner surface 35 that forms a cannulation 33. The outer surface of the implant 30 is shown at 37.

FIG. 3 illustrates an implementation of the first sensor 32. The first sensor 32 may include two coils cross-layered to one another and having an angle α.

FIGS. 4 and 5 illustrate another implementation of the first sensor 32. The first sensor may include two coils generally orthogonal to one another in order to establish the orientation and position in the six degrees of freedom. A first coil may be oriented along the length of the implant 30. The second coil may be oriented either wrapped around the circumference of the implant, for example in a groove, or along the radius of the implant 30. In addition, while the coils may be perpendicular to one another, other orientations may be used, although the mathematics may be more complex. Further, the coils may be oriented spirally around the implant 30. Such an orientation may allow two coils to be placed perpendicular to each other with both coils placed along both the length of the implant and along the circumference of the implant 30.

Figure 6:
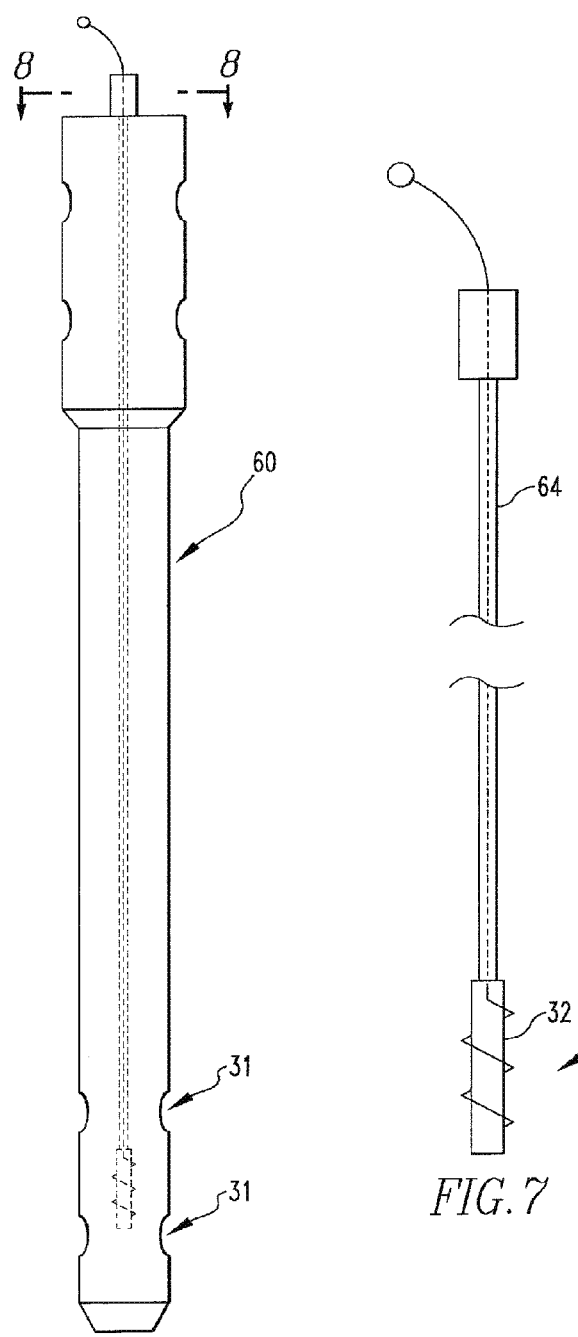
FIG. 6 illustrates another orthopaedic implant assembly.
Figure 7:
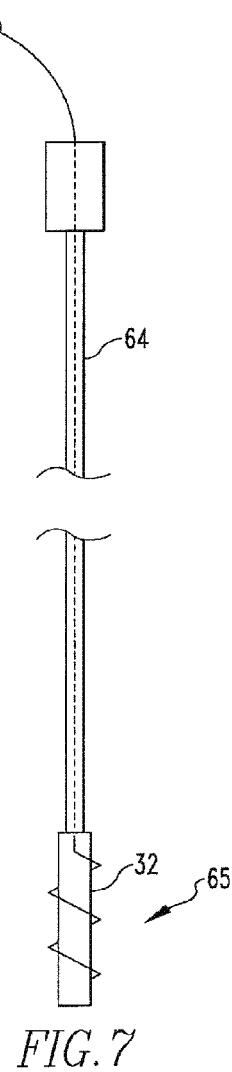
FIG. 7 is a partial plan view of a removable lead.
Figure 8:
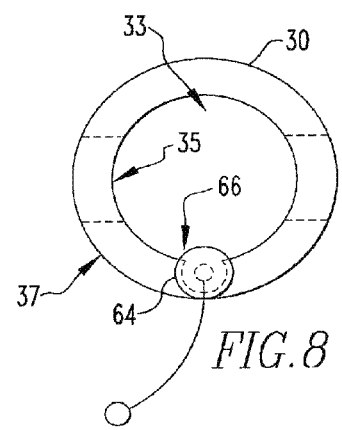
FIG. 8 is a top view of the orthopaedic implant assembly illustrated in FIG. 6.

FIGS. 6-8 illustrate a second implementation of the orthopaedic implant assembly 60. The orthopaedic implant assembly 60 may include the implant 30. In FIG. 6, the implant 30 includes landmarks in the form of transfixion holes 31. The implant 30 may include a longitudinal internal groove 66 and a removable lead 64. In FIG. 8, a diameter of the longitudinal groove 66 is shown as intersecting with the cannulation 33; however, in other implementations, the diameter of the longitudinal internal groove is contained between the outer surface 37 and the inner surface 35. The removable lead 64 may include the first sensor 32 at its distal end portion 65. The first sensor 32 is located a known offset from the landmarks 31. The implant in FIGS. 6-8 is comprised of biocompatible material, and may be a metal alloy or a polymer. The longitudinal groove 66 may be machined or molded in place.

In use, the implant 30 with the removable lead is installed in a patient. For example, in the case of internal fixation, the intramedullary nail is placed within an intramedullary canal. Optionally, the user may use transfixion elements, such as screws, to first lock the proximal end of the intramedullary nail. Because of the location of the longitudinal groove 66, the removable lead 64 does not interfere with locking the proximal end of the intramedullary nail. An operator uses the targeting device 18 and the first sensor 32 to identify the landmarks 31. For example, in the case of intramedullary nail fixation, a surgeon uses the targeting device 18 to identify the blind transfixion holes 31 and drill through the holes 31 for placement of a transfixion element. After the implant 30 is secured, the operator removes the removable lead 64 and it may be discarded.

A method for identifying a landmark is disclosed. The method may include providing an orthopaedic implant assembly having an orthopaedic implant with a longitudinal groove and a removable lead or probe having an electromagnetic sensor attached thereto situated within the longitudinal groove. The orthopaedic implant includes a proximal end portion, a distal end portion, and at least one landmark on the distal end portion. The method includes implanting the orthopaedic implant assembly in a patient. Then, transfixion elements in the proximal end portion are installed. At least one distal landmark is identified using a landmark identifier. A transfixion element is installed in the at least one distal landmark. The removable lead or probe may then be removed. The situation of the removable lead or probe within the longitudinal groove allows for proximal locking of the implant prior to distal locking.

Figure 9:
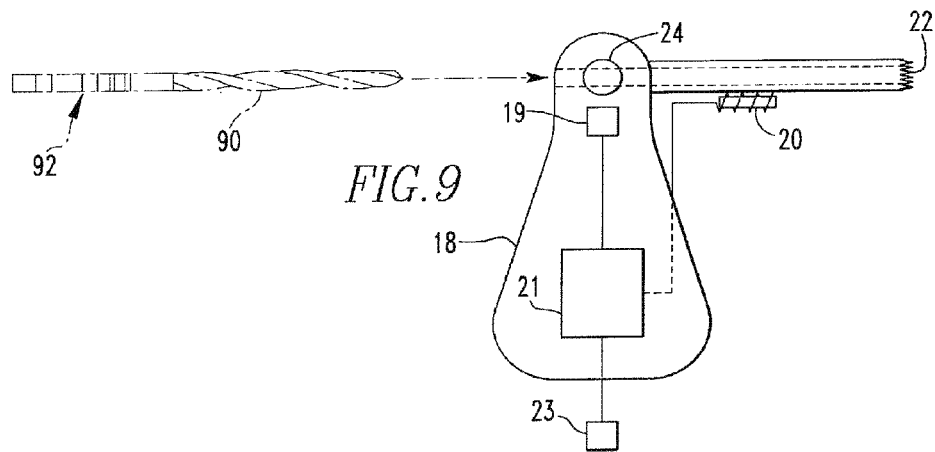
FIG. 9 illustrates a landmark identifier that includes a drill sleeve.

FIG. 9 illustrates the landmark identifier 18 of FIG. 1. The landmark identifier 18 may include the sensor 20, the serrated tip 22, the tube 24, and the handle 26. A drill 90 has markings 92 that interact with a marking sensor 19 adjacent the tube 24. The interaction is similar to a pair of digital measuring calipers in that the position between the markings 92 and the sensor 19 equate to a distance. This distance can be used to determine the depth of the drill into the bone and ultimately the length of the bone screw that will be inserted into the drilled hole. Distance, or drill depth, readings are only obtainable when the markings 92 and the sensor 19 are in close proximity to each other, i.e. the drill 90 is inside the tube 24. Exemplary measurement devices are illustrated in U.S. Pat. No. 6,675,491 and U.S. Pat. No. 7,253,611. The marking sensor 19 is connected to the communications module 21. Alternatively, the marking sensor 19 may be connected by wire to the processor 12. In FIG. 9, the communications module 21 may include a third connector 23 for electrical connection to the processor 12.

Figure 10:
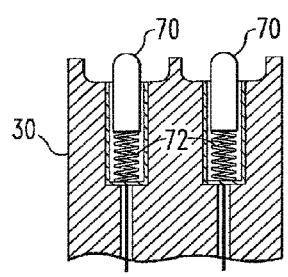
FIG. 10 is a partial and sectional view illustrating two point contacts of an implant.
Figure 11:
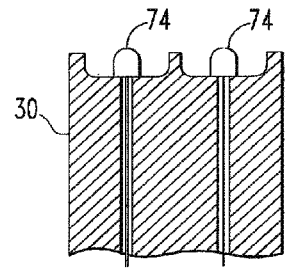
FIG. 11 is another partial sectional view illustrating point contacts in another implant.
Figure 12A:
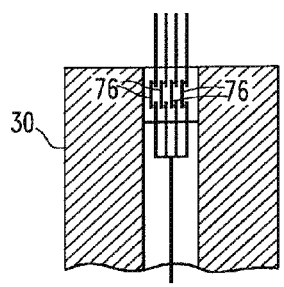
FIG. 12A is a partial and sectional view of an implant illustrating a crimp electrical connection.
Figure 12B:
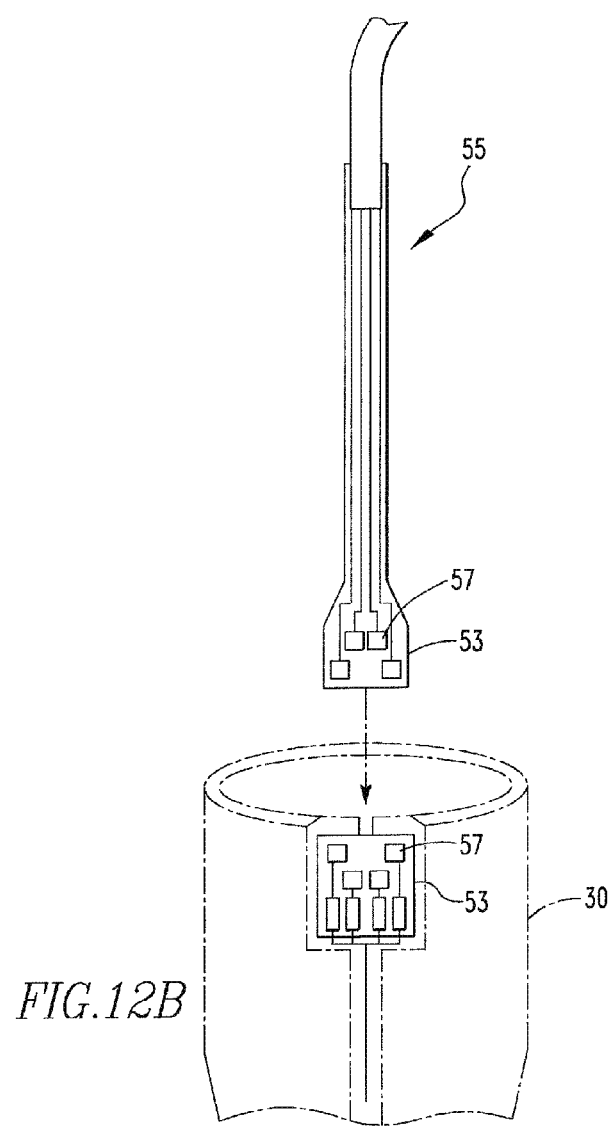
FIG. 12B is a partial exploded view illustrating the electrical connection in a disclosed implant.
Figures 12C, 12D:
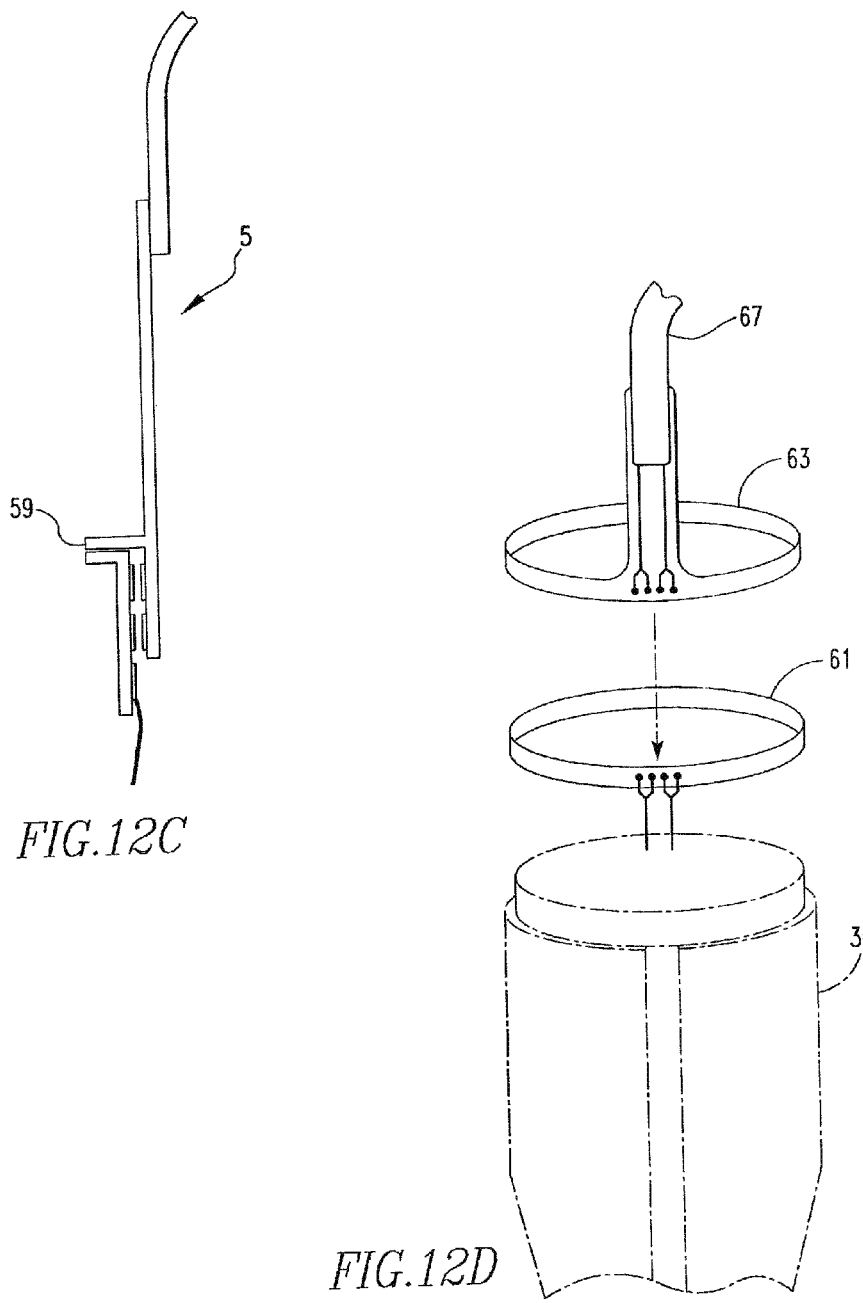
FIG. 12C is a side view of the electrical connection illustrated in FIG. 12B.
FIG. 12D is a partial exploded illustrating the electrical connection in another disclosed implant.

FIGS. 10-12 illustrate exemplary methods of electrically connecting the implant 30 to the insertion handle 40, which has corresponding electrical contacts. In FIG. 10, biasing elements 72 bias contacts 70 toward the insertion handle 40. In FIG. 11, the implant 30 has elastomeric electrical contacts 74. In FIG. 12A, wires extending between the lead 50 and another component are crimped together at junction 76. In one method, the wires are torn free and separated at the junction 76 after installation of the orthopaedic implant assembly 28. In yet another method, the wires are cut above the junction 76 after installation of the orthopaedic implant assembly 28. In FIGS. 12 B and C, two flex boards 53 are soldered together one or more pads 57 to connect a wiring harness 55 to the sensor. The wire harness 55 may be mounted to the insertion handle 40 or within a cannulation of the insertion handle 40. In the depicted implementation, four pads 57 are soldered together. Locking tabs 59 are sandwiched between the implant 30 and the insertion handle 40 to withstand abrasion and tension associated with the implant insertion. Once the insertion handle 40 is removed, the wire harness 55 can be pulled such that all non-biocompatible materials are pulled with it. In FIG. 12D, rings 61, 63 are connected during manufacturing. After implantation, both rings 61, 63 are removed by pulling on a jacketed wire 67.

Figure 13A:
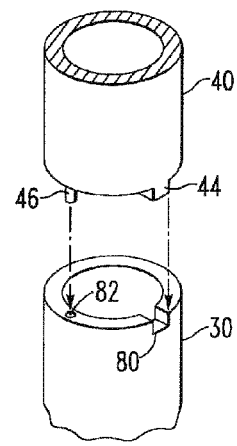
FIG. 13A is a partial perspective and exploded view illustrating alternative mechanisms for aligning a disclosed orthopaedic implant and a disclosed insertion handle.
Figure 13B:
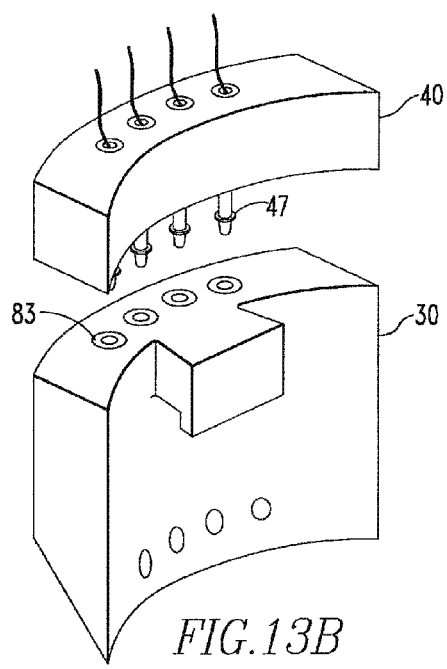
FIG. 13B is a partial perspective and exploded view illustrating alternative mechanisms for aligning a disclosed orthopaedic implant and an electrical connection.

Referring now to FIGS. 13A and 13B, the implant 30 and/or the insertion handle 40 may include one or more alignment features 44 and mating notch 80 or alignment pin 46 and mating hole 82. The insertion handle may be configured to align with an upper surface of the implant. In one implementation, the insertion handle may have a key configured to mate to a slot on the implant. Other alignment guides may be used. In addition, the guide may have an electrical connector configured to mate to an electrical connector on the implant. The connection between the guide and the implant may be spring loaded to ensure electrical contact between the electrical connectors. In order to avoid shorting the connection between the guide and the implant, the electrical connector may be insulated. As another example of electrically connecting the insertion handle to the implant, the electrical connectors may include a post and slip rings. The rings may be located on the implant, and the posts located on the insertion handle. The posts are biased to contact the rings. In such an implementation, the angular location of the insertion handle 40 relative to the axis of the implant is not fixed. This would allow the insertion handle 40 to be positioned to the implant irrespective of angular position.

In another implementation shown in FIG. 13B, the implant 30 and/or the insertion handle 40 may include one or more alignment pin 47 and mating hole 83. The alignment pins 47 may be spear tip pins designed to engage a single time and when removed, the pins grip portion of the implant to remove all non-biocompatible materials with them.

Any of the electrical connectors above may include a memory storage device (not shown) for storing offset values for sensor calibration.

Figure 14:
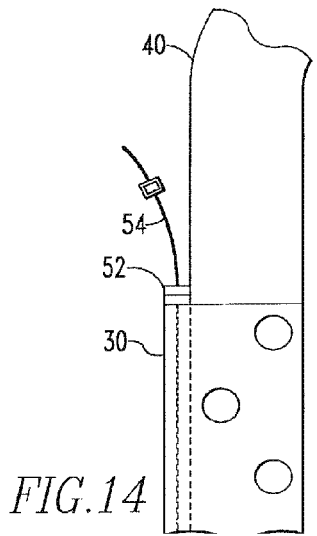
FIG. 14 is a partial side view illustrating a connection of the insertion handle to the orthopaedic implant.

Referring now to FIG. 14, the implant 30 and the insertion handle 40 may be sized such that space remains available for the first connector 52 even when the components are assembled or mated. As an example, the system for identifying a landmark may be used to target blind screw holes of an implanted intramedullary nail. The intramedullary nail is implanted in the patient. The electromagnetic field generator is activated. The processor receives signals from the sensor mounted to the intramedullary nail and from the sensor mounted to the landmark identifier, such as a drill sleeve. A computer program running on the processor uses the information of the at least two sensors and graphically display them in relative position on the monitor. A surgeon moves the landmark identifiers into position using feedback provided by the processor. When the landmark identifier is in the proper location, the surgeon drill through bone and the intramedullary nail to create a screw hole. The processor may provide feedback as to the depth of the drilled hole. The surgeon may then place a screw through the drilled hole to affix the blind hole of the intramedullary nail.

Provided feedback information may be selected from the group consisting of audible, visual, and tactile. The audible feedback may be output through a speaker, headphones, ear buds, or an ear piece. The audible feedback signal may be transmitted over wire or wirelessly using radio frequency or terrestrial data transmission. The visual feedback may be output through a cathode ray tube, a liquid crystal display, or a plasma display. Visual feedback devices may include, as examples, a television monitor, a personal digital assistant, or a personal media player. The visual feedback signal may be transmitted over wire or wirelessly using radio frequency or terrestrial data transmission. The tactile feedback may be output through gloves, instruments, or a floor mat. The tactile feedback signal may be transmitted over wire or wirelessly using radio frequency or terrestrial data transmission.

Figure 15:
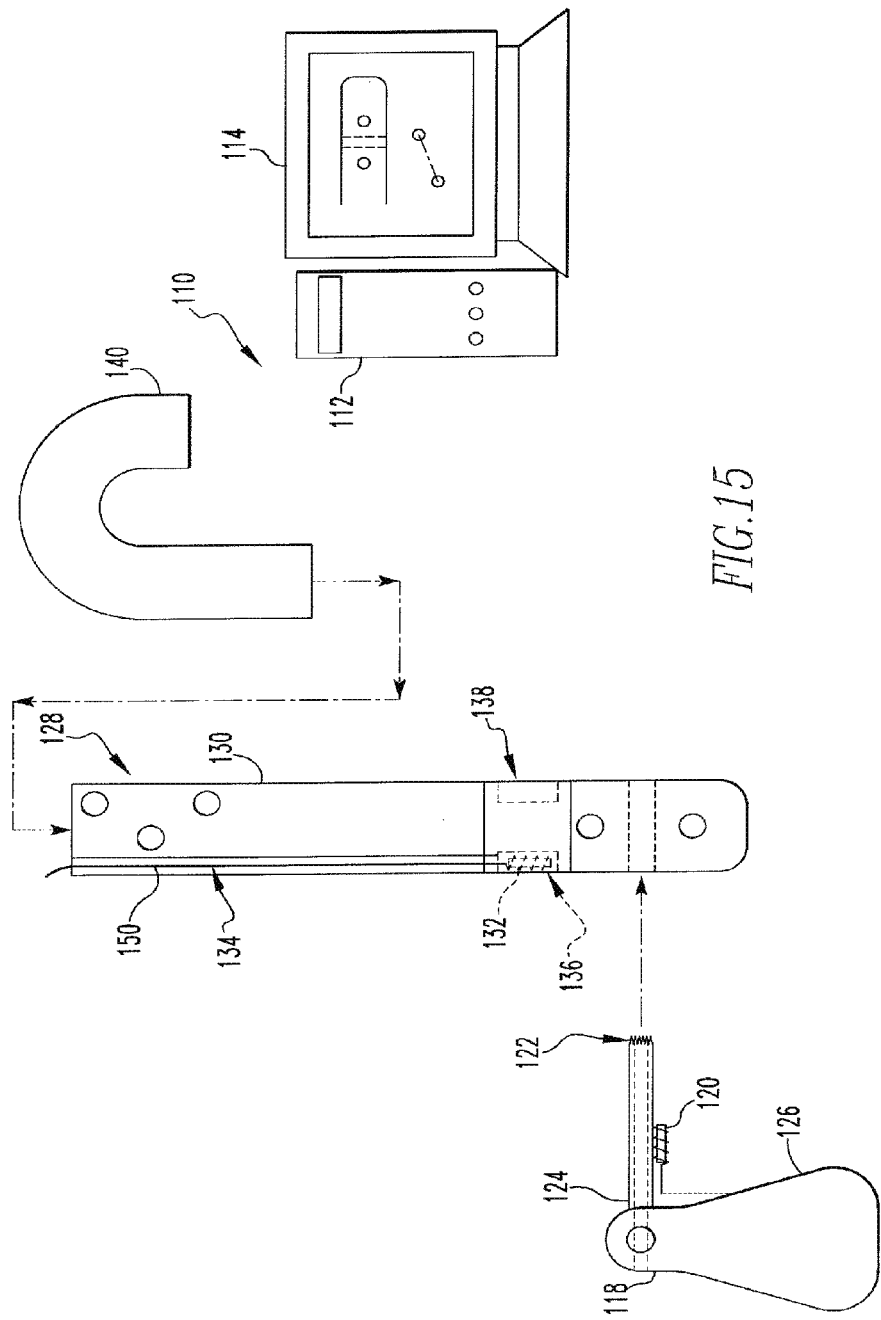
FIG. 15 illustrates another system for identifying a landmark.

FIG. 15 illustrates a system 110 for identifying a landmark in another implementation. The system 110 may include a processor 112, a landmark identifier 118, and an orthopaedic implant assembly 128. The system 110 may also include a monitor 114 and an insertion handle 140.

The landmark identifier 118 is used to target a landmark. The landmark identifier 118 may include a second sensor 120. In FIG. 15, the landmark identifier 118 is a drill sleeve with a serrated tip 122, a tube 124, and a handle 126. The second sensor 120 is oriented relative to an axis of the tube, which may receive a drill. This offset of the sensor from the tube allows the position of the tube to be located in space in six dimensions (three translational and three angular) relative to the transmitter or another sensor in the system. The processor may need to be calibrated to adjust for the offset distance of the second sensor 120.

The orthopaedic implant assembly 128 may include an implant 130 and a magnet 132. The magnet may be a permanent magnet or an electromagnet. The magnet 132 is oriented in a predetermined position relative to a landmark on the orthopaedic implant 130. This offset of the magnet from the landmark allows the position of the landmark to be located in space in six dimensions (three translational and three angular) relative to the transmitter or another sensor in the system, such as the second sensor. The processor may need to be calibrated to adjust for the offset distance of the magnet 132. As with the implant 30 of FIG. 1, the implant 130 may also include a pocket 136 and a cover 138. In the case of an electromagnet, a lead 150 connects to the magnet 132 and is contained within a groove 134.

As an example, the system for identifying a landmark may be used to target blind screw holes of an implanted intramedullary nail. The intramedullary nail is implanted in the patient. The processor receives signals from the sensor mounted to the landmark identifier, such as a drill sleeve. A computer program running on the processor uses the information of the sensor and graphically displays the sensor in relative position to the magnet on the monitor. A surgeon moves the landmark identifiers into position using feedback provided by the processor. When the landmark identifier is in the proper location, the surgeon drill through bone and the intramedullary nail to create a screw hole. The processor may provide feedback as to the depth of the drilled hole. The surgeon may then place a screw through the drilled hole to affix the blind hole of the intramedullary nail.

Figure 16:
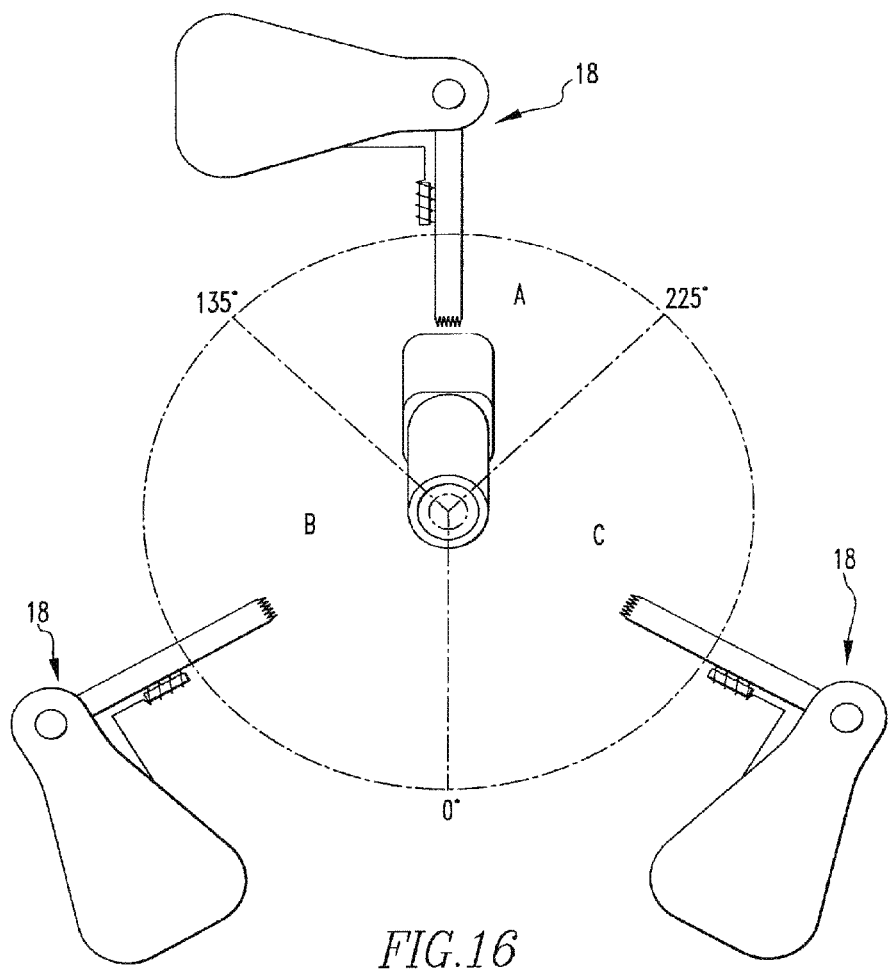
FIG. 16 is a schematic illustration of view selection criteria.

FIG. 16 illustrates a method for selecting views corresponding to landmark identifier position. The view displayed on the monitor is dependent upon the location of the landmark identifier relative to the implant. The diameter of the implant is broken into sectors or fields. In FIG. 16, the diameter is broken down into three fields: (A) 135° to 225°; (B) 0° to 135°; and (C) 225° to 360°. The initial view is based upon landmark identifier orientation relative to the implant. As the user moves landmark identifier toward or away from the implant, the monitor display zooms in or out on the selected field.

Figure 17:
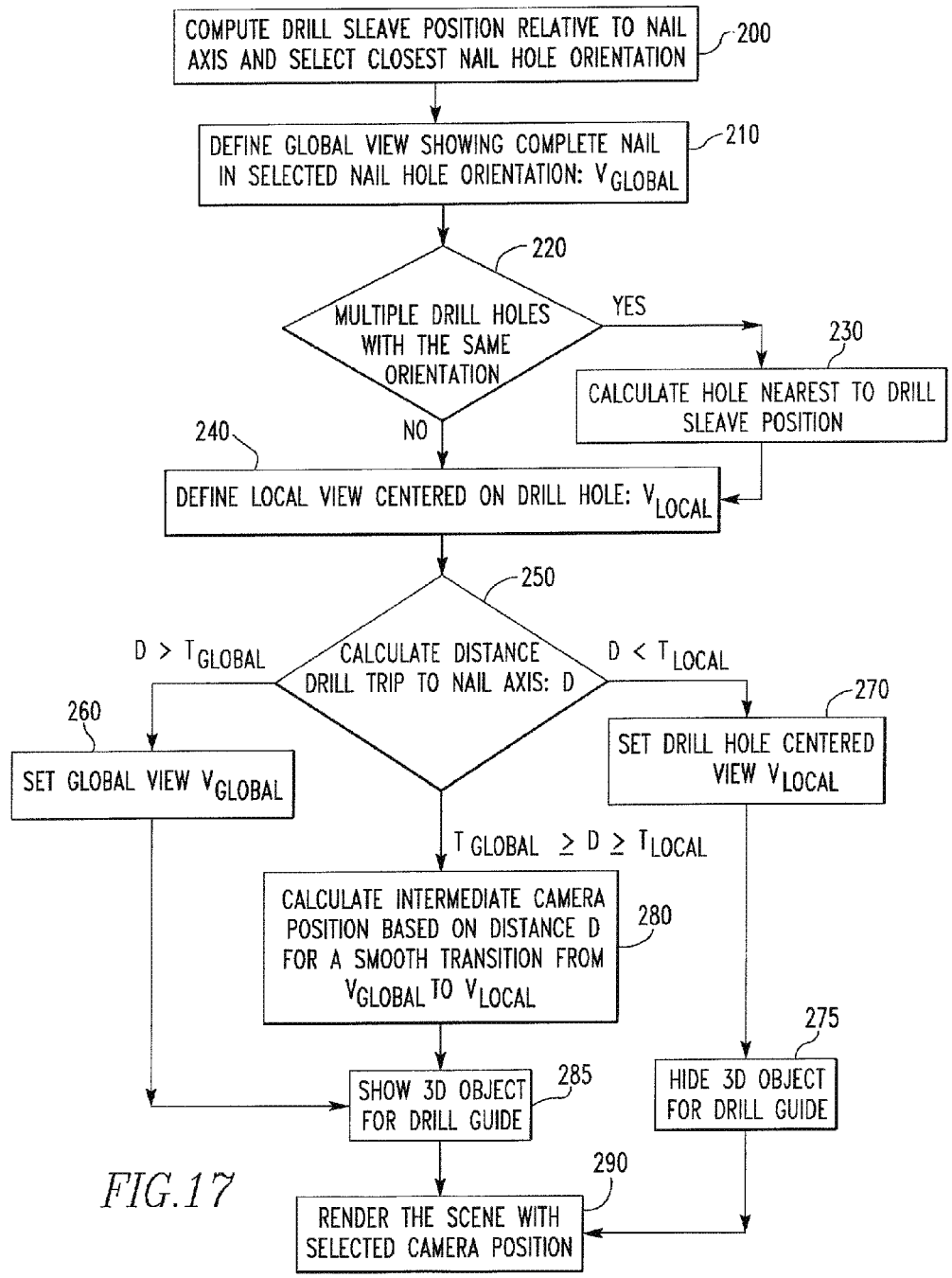
FIG. 17 is a flowchart illustrating view selection during a fixation surgery.

FIG. 17 is a flowchart for view selection and display of one landmark. The process may be repeated for multiple landmarks. The processor 12 uses the transformation matrix in the following process steps. In step 200, landmark identifier position is computed relative to the implant based upon the positions of the relevant sensors, and the landmark closest the landmark identifier is selected for display. In step 210, a global view is defined showing the whole implant with the selected landmark oriented for proper viewing. A global view is analogous to viewing the implant at a distance. In step 220, there is a decision whether there are multiple landmarks having the same orientation. If yes, then in step 230, the processor calculates which landmark is nearest to the landmark identifier position and selects it for viewing. If no, in step 240, a local view is defined and centered upon the selected landmarks. A local view is analogous to viewing the implant in close proximity. In some implementations, it may be desirable to hide the landmark identifier when the local view is defined. In steps 250, 260, and 270, the processor 12 identifies the distance from landmark identifier to the landmark and depending upon the decision made, either hides or renders the landmark identifier. In step 250, the distance from landmark identifier to the landmark and a comparison is made between the calculated distance D and set variables $T_{Global}$ and $T_{Local}$. If $D>T_{Global}$, then the global view is selected in step 260 and the processor proceeds to step 285. If $D<T_{Local}$, then the local view is selected and centered upon the landmark in step 270. Thereafter, the processor proceeds to step 275. In optional step 275, the landmark identifier is hidden. Otherwise, an intermediate camera position is calculated based upon the distance D to enable a smooth transition from global view to a local view in step 280. In step 285, the landmark identifier is shown. In step 290, the scene with selected camera position is rendered.

Figure 18:
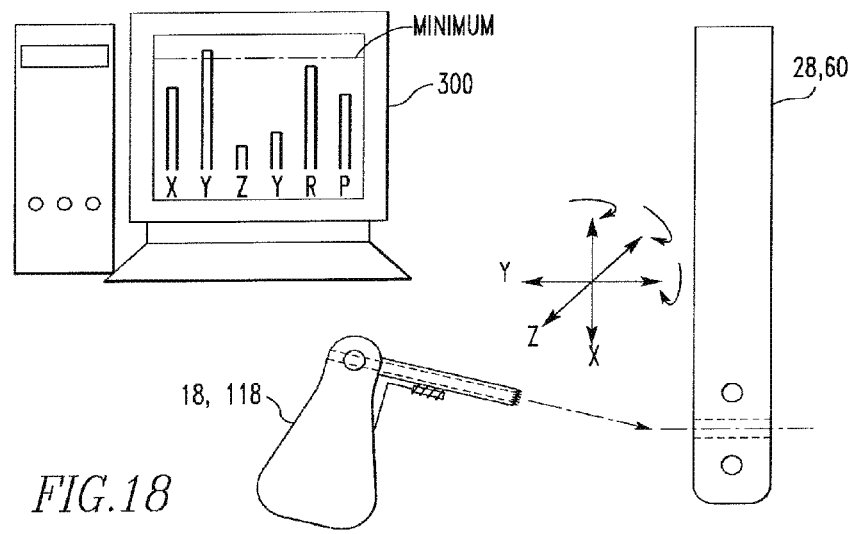
FIG. 18 is a schematic illustration of another method of aligning a landmark identifier.

FIG. 18 is a schematic illustrating a first alternative method of aligning the landmark identifier. A computer program running on the processor may be used to take the information of the at least two sensors and graphically display them in relative position (the second sensor relative to the first sensor) on the monitor. This allows the user to utilize the system to guide the placement of the landmark identifier. In the case of drilling a blind intramedullary nail hole, the system guides the user in placement of the drill sleeve and subsequently drilling accurately thru the hole in the intramedullary nail. The graphical user interface may include an alignment guide for each of the degrees of freedom. A minimum alignment level may be set such that the surgeon continues to orient the landmark identifier until each of the degrees of freedom meets the minimum alignment level for an effective placement of the landmark identifier. The example of FIG. 18 shows an instance where the placement in the Y-direction meets the minimum required tracking placement. However, none of the other translational or rotational meets the minimum requirements. While the magnitudes of tracking are illustrated as bar graphs, other graphical representations, such as color coding, may be used.

Figure 19:
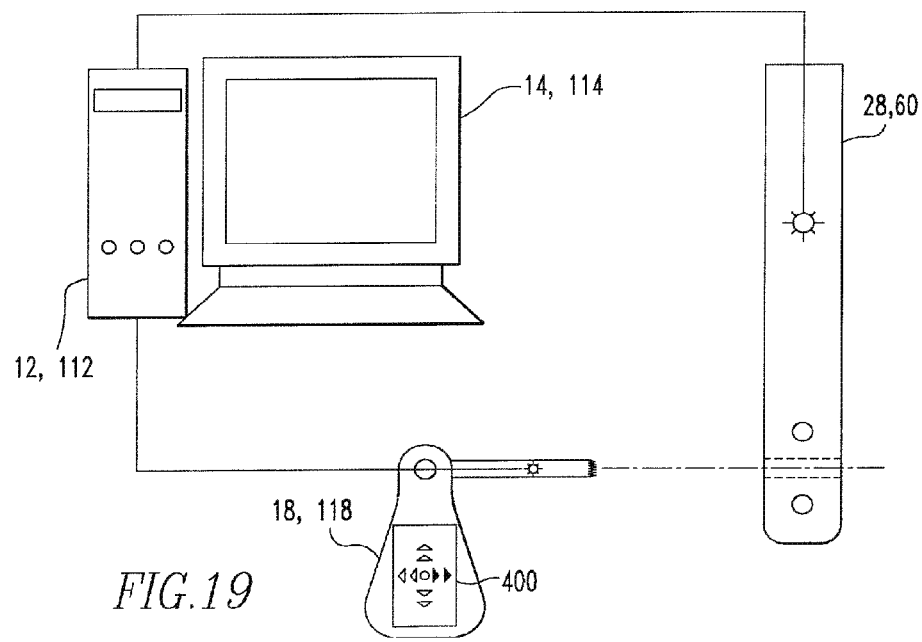
FIG. 19 is a schematic illustration of another disclosed method of aligning a landmark identifier.

FIG. 19 is a schematic illustrating a second alternative method of aligning the landmark identifier. In this implementation, a graphical interface using a plurality of LEDs to position the drill may be placed upon the landmark identifier, such as a drill sleeve. By using the LEDs to trajectory track the drill, the surgeon may align the drill with the blind fixation hole. The trajectory may additionally use secondary displays to add more information to the system. For example, for affecting the magnitude of adjustment, the trajectory may include flashing LEDs so that high frequency flashing requires larger adjustments while low frequency flashing may require smaller adjustments. Similarly, colors may add information regarding adjustments to alignment.

Figure 20:
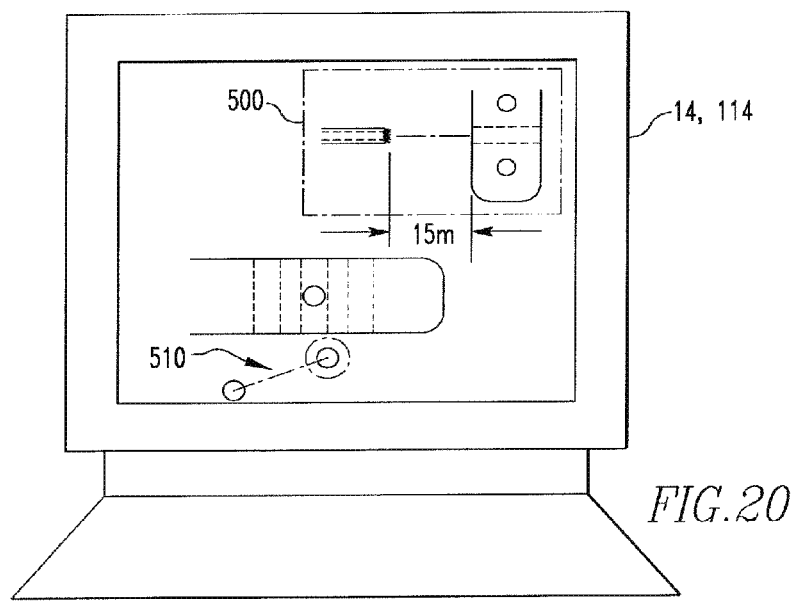
FIG. 20 illustrates a disclosed monitor with exemplary views.

FIG. 20 illustrates a monitor with exemplary views. A first portion 500 indicates the distance the drill is on each side of the implant. This may provide the user with a better understanding of drill depth and alert the user when to stop when appropriate drill depth has been achieved. The second portion 510 provides the user with alignment information. As an example, drill depth data may be obtained using the implementation illustrated in FIG. 9.

Figure 21:
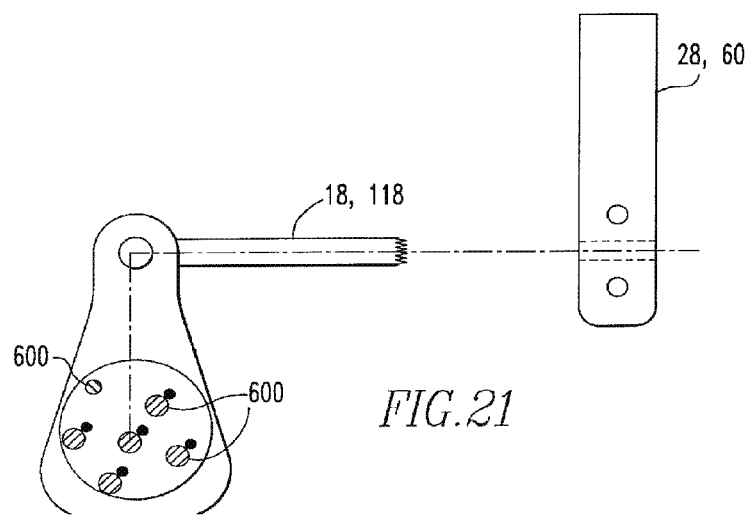
FIG. 21 illustrates another disclosed landmark identifier.

FIG. 21 illustrates an alternative implementation of the landmark identifier. The landmark identifier is configured to display, with LEDs, the position and trajectory information for proper alignment. The size of the LEDs may display additional information regarding the magnitude of required adjustment. The trajectory light may display a simple on/off toggle between an aligned trajectory and a mal-aligned trajectory. As another example, the trajectory LED may be color coded to suggest the magnitude of necessary adjustment for proper alignment.

Figure 22:
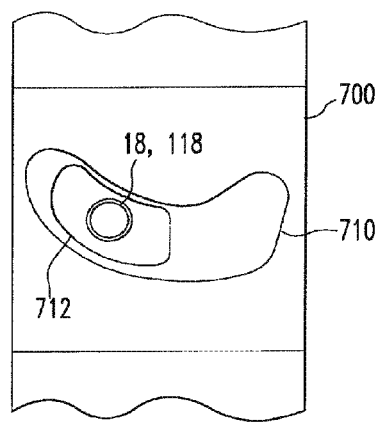
FIG. 22 is a partial view another disclosed insertion handle.

FIG. 22 illustrates a first alternative implementation of the insertion handle 700. The insertion handle 700 may include an arcuate slot 710. The arcuate slot limits the movement of the landmark identifier 18, 118 within the operating space. In the case of identifying a blind screw hole, the arcuate slot limits the movement of the drill sleeve for fine adjustment of its position. The insertion handle 700 may include a carriage 712 that receives the landmark identifier and rides in the slot 710.

Figure 23:
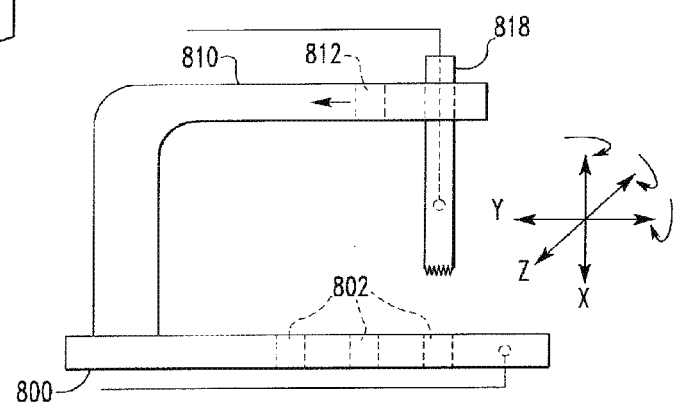
FIG. 23 illustrates another disclosed system for identifying a landmark.

FIG. 23 illustrates the system for identifying a landmark in a third implementation. In this implementation, the orthopaedic implant 800 is a bone plate and the insertion handle 810 is a little guide affixed to the bone plate. The inductive sensor is placed on the surface of the orthopaedic implant 800 relative to one or more landmarks. The guide 810 may allow a landmark identifier 818 to translate and/or rotate relative to the guide to properly align the landmark identifier with a landmark 802, such as a fastener hole. In addition, where multiple fixation holes are on the implant, then additional guide holes 812 on the guide 810 may help approximate the position of the additional fixation holes.

Figure 24:
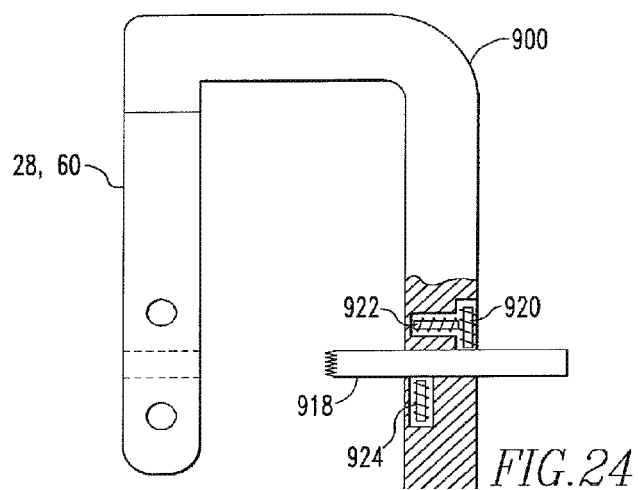
FIG. 24 is a partial view of yet another disclosed insertion handle.

FIG. 24 illustrates a second alternative implementation of the insertion handle. The insertion handle 900 may include fine adjustment in landmark identifier 918 positions through the use of small servomotors 920, 922, 924. The servomotors 920, 922, 924 may adjust the orientation and position of the landmark identifier 918. Control of the servos may be automatic or may be controlled by a surgeon.

Figure 25:
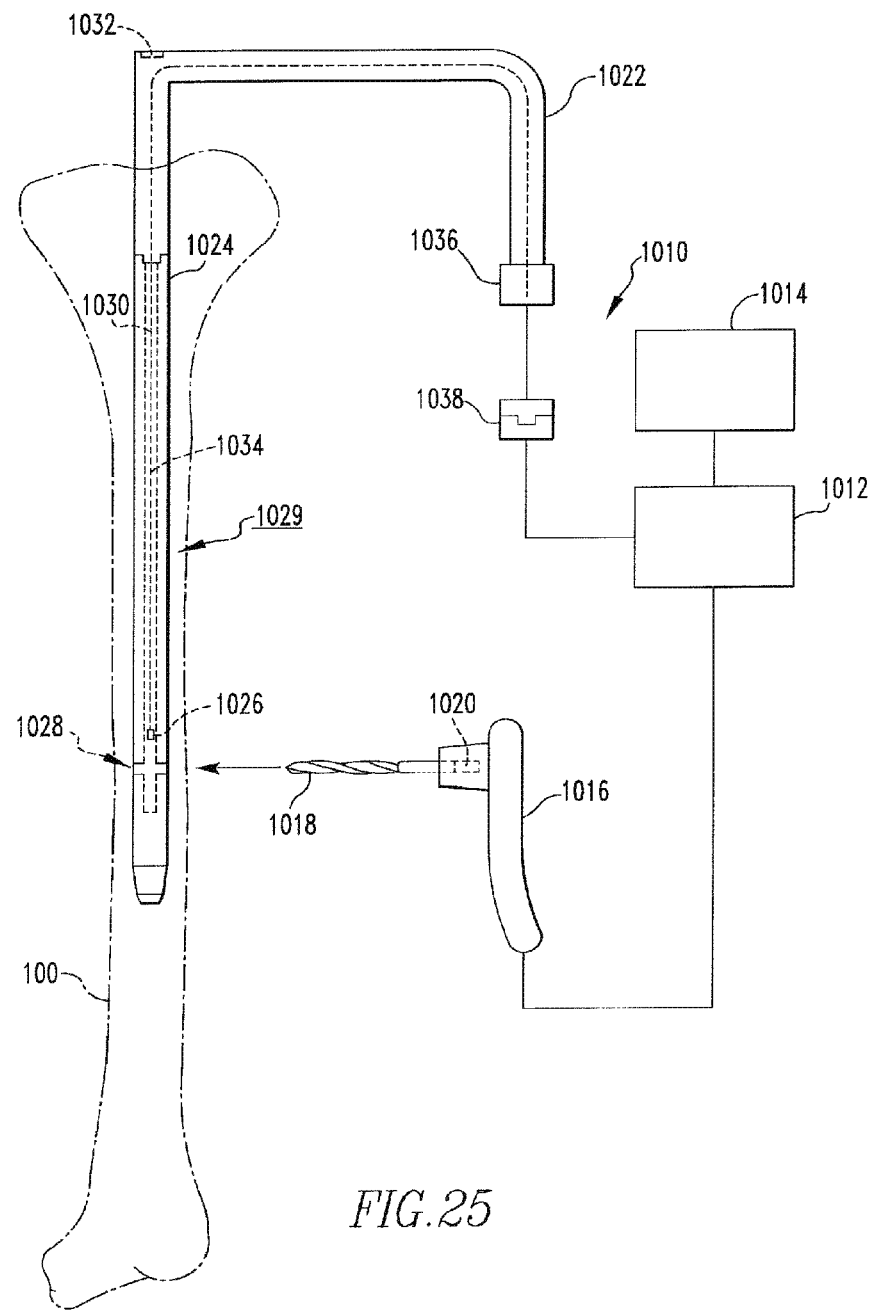
FIG. 25 illustrates another disclosed system for identifying a landmark.

FIG. 25 illustrates a bone 100 and another system 1010 for identifying a landmark. The system 1010 may include a control unit 1012, a field generator 1014, a landmark identifier 1016, an intramedullary nail 1024, and a probe 1029. The landmark identifier 1016 also may be referred to as a targeter. The control unit 1012 may be included as part of the processor described above or may be a separate unit. The intramedullary nail 1024 is inserted into the bone 100, and the intramedullary nail 1024 has a hole or landmark 1028. The field generator 1014 is electrically connected to the control unit 1012. An insertion handle 1022 is removably attached to the intramedullary nail 1024. The insertion handle 1022 and/or the intramedullary nail 1024 may be formed with a cannulation. The insertion handle 1022 may include a third sensor 1032.

The landmark identifier 1016 may include a second sensor 1020. The landmark identifier 1016 may guide a drill bit 1018, and the drill bit 1018 may be connected to a drill (not shown). The second sensor 1020 may be connected to the control unit 1012, either by wire or wirelessly. The field generator 1014 may be included in or on the landmark identifier 1016, in which case, the second sensor 1020 may be omitted.

The probe 1029 may include a wire 1030, a tape 1034, and a stop 1036. The tape 1034 may be about 0.125 inch wide by about 0.060 inch thick 300 series stainless steel fish tape available from Ideal Industries, Inc. of Sycamore, Ill. However, those of ordinary skill in the art would understand that other materials and other sizes may be used. For example, any narrow band of polymer, composite material, or metal may be used as the tape 1034, but it may be preferred to use a non-ferrous metal. The tape 1034 may be coiled before placement into the intramedullary nail 1024. Coiling of the tape 1034 may cause it to have a natural curvature. The tape 1034 may have, in some implementations, a rectangular geometry that assists in orienting the tape as it is placed into a cannulation of the intramedullary nail 1024. An oval, square, or circular geometry also may be used. The wire 1030 may be operatively connected to the tape 1034. For example, this may be accomplished through the use of an adhesive or fastener. The tape 1034 may include graduations or detents to indicate a depth of the tape as it is inserted into the implant.

A first sensor 1026 is connected to the control unit 1012, either by wire or wirelessly. The first sensor 1026 is connected through the use of the wire 1030 and a connector 1038. The connector 1038 may be omitted. The first sensor 1026 may be connected to a distal end of the tape 1034, and the stop 1036 may be connected to a proximal end of the tape 1034.

The probe 1029 may include a sensor housing (not shown) to house the first sensor 1026. The sensor housing may be attached to the tape 1034. The sensor housing may be made of a non-ferrous material, such as a polymer, a composite, or a metal. The sensor housing may include an appropriate strain relief to shield the wire 1030 from stresses. The sensor housing may be constructed and arranged to be large enough to hold the first sensor 1026 but small enough to fit through the cannulation of the insertion handle or the implant. Further, the sensor housing may be constructed and arranged to be long enough to allow passage through intramedullary nail bends, intramedullary nail bow, and/or bends in relevant instrumentation. Geometry of the leading and trailing faces of the sensor housing may be designed such that the sensor housing does not catch or snag on the cannulation of the instrumentation or implant.

The stop 1036 may be used to control the placement of the sensor 1026 and probe 1029. If the tape 1034 is a fixed length and the distance is known from the end of the insertion handle to the hole 1028, repeatable placement of the first sensor 1026 may be achieved. The tape 1034 may be of sufficient length such that the sensor 1026 is aligned with the hole 1028, adjacent the hole 1028, or offset from the hole 1028. As discussed below, the probe 1029 may be used to position the sensor with the hole 1028 or other landmark.

The insertion handle 1022 may be omitted. In such a case, a different tape length may be selected such that the stop 1036 engages a portion or end of the nail 1024.

Figure 26:
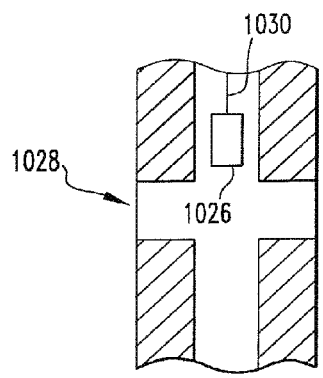
FIG. 26 is a partial cross-sectional view of an intramedullary nail.

FIG. 26 is a partial detailed view of the intramedullary nail 1024, the sensor 1026, and the hole 1028. The sensor 1026 may be aligned with the hole 1028, adjacent the hole 1028, or offset from the hole 1028. The sensor 1026 is generally adjacent to the hole 1028.

In use, the intramedullary nail 1024 is placed into the bone 100. The insertion handle 1022 may be attached to the intramedullary nail 1024. The probe 1029 is fed through the cannulation of the insertion handle 1022 and into the cannulation of the intramedullary nail 1024 until the stop 1036 engages the insertion handle 1022. In one particular implementation, the wire 1030 is connected to the control unit 1012, and the sensors 1026, 1020, and 1032 are calibrated using the control unit 1012. The probe 1029 may be removed after calibration. If so, the third sensor 1032 and a transformation matrix may be used to identify the relative position of the second sensor 1020 and hence landmark identifier 1016. Optionally, the user may use transfixion elements, such as screws, to first lock the proximal end of the intramedullary nail. An operator uses the landmark identifier 1016 and the first sensor 1026 to identify the landmarks 1028. For example, in the case of intramedullary nail fixation, a surgeon uses the landmark identifier 1016 to identify the blind transfixion holes and drill through the holes for placement of a transfixion element.

Figure 27:
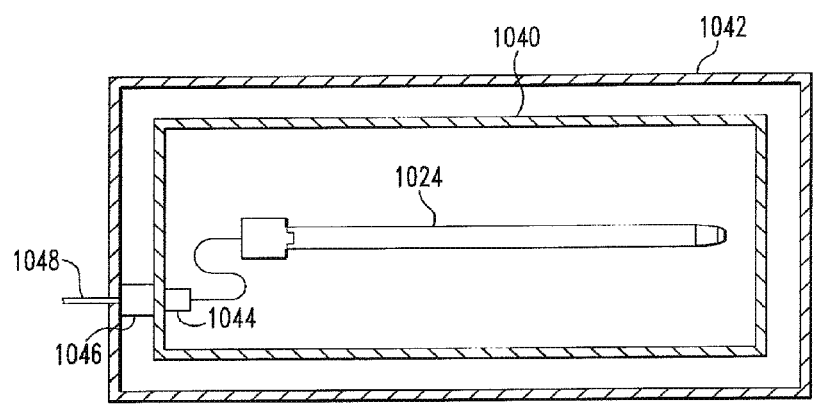
FIG. 27 illustrates a packaging for a disclosed implant.

FIG. 27 illustrates a packaging implementation. In general, intramedullary nails must be sterilized before implantation. If the sensor is installed in the intramedullary nail prior to serialization, the sensor may lose its calibration during the serialization process, particularly if the sterilization process involves radiation. For example, gamma radiation may be used to sterilize hermetically sealed components, such as the sensor. The implementation depicted in FIG. 27 illustrates a way to maintain the sterilization of the intramedullary nail while allowing for recalibration of the sensor. The package FIG. 27 may include a first package 1040, a second package 1042, a first connector 1044, a second connector 1046, and a cable 1048. In the depicted implementation, a sensor (not shown) and intramedullary nail 1024 are located within the first package 1040. Alternatively, the probe 1029 and the sensor are located within the first package 1040. In yet another example, only the sensor is located within the first package 1040. A memory device (not shown) may be connected to the sensor. The memory device may be used to store a calibration transformation matrix (x1, y1, z1, x2, y2, z2) as well as other data, such as length and size of the intramedullary nail or the probe. The memory device may be mounted to or placed on the intramedullary nail 1024 or the probe 1029. The first connector 1044 is electrically connected, but removably attached, to the second connector 1046. The first connector 1044 is also electrically connected to the sensor or the memory device. The first package 1040 maintains the sterilization of the device held within. The cable 1048 is electrically connected to the second connector 1046 and a storage device (not shown). The calibration for the sensor is downloaded from the storage device and transmitted through the connectors 1044, 1046 to the sensor or the memory device. The calibration step may be performed during manufacturing of the system or immediately prior to implantation of the implant.

Figure 28:
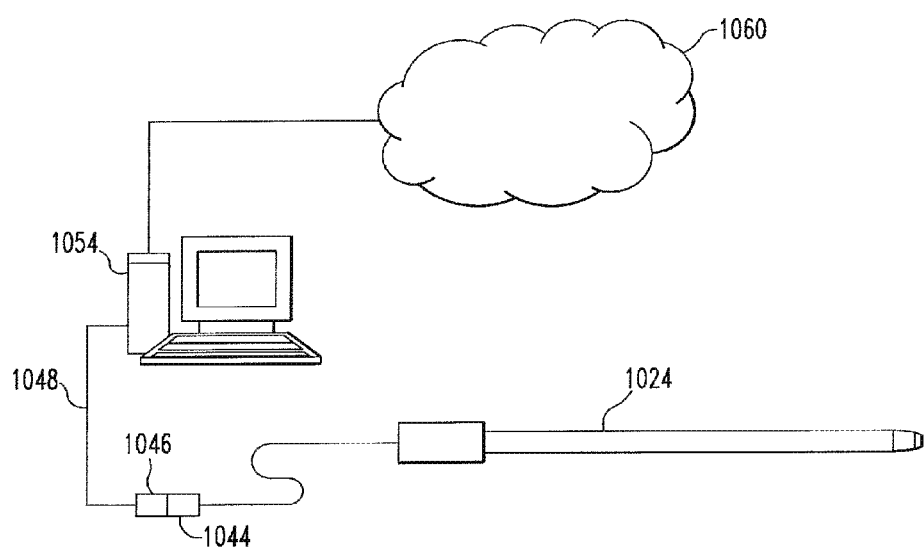
FIG. 28 illustrates a method of connecting a landmark identifier system to a network.

FIG. 28 illustrates a method of connecting the system 1010 to a network. FIG. 28 illustrates a network 1060, a computing device 1050, the cable 1048, the second connector 1046, the first connector 1044, and the intramedullary nail 1024. In the depicted implementation, a sensor (not shown) is located within the intramedullary nail 1024. Alternatively, the sensor may be attached to the probe 1029 or freestanding. The intramedullary nail 1024 may be wrapped in packaging, such as the first package 1040 and/or second package 1042 but this is not always the case. A memory device (not shown) may be connected to the sensor. The memory device may be used to store a calibration transformation matrix (x1, y1, z1, x2, y2, z2) as well as other data, such as length and size of the intramedullary nail or the probe. The memory device may be mounted to or placed on the intramedullary nail 1024 or the probe 1029. The network 1060 may be a local area network or a wide area network. The computing device 1054 is connected to the network 1060. The network communication may be encrypted. The cable 1048 connects the computing device 1054 to the sensor or the memory device through the use the connectors 1044, 1046. In this way, the sensor calibration may be downloaded from the computing device 1054 and/or the network 1060. While the depicted implementation illustrates the sensor within the intramedullary nail, this is not always the case. The sensor may be attached to the probe or freestanding. The memory device may be located within the control unit, and the control unit is connected to the network to download the calibration data.

Figure 29:
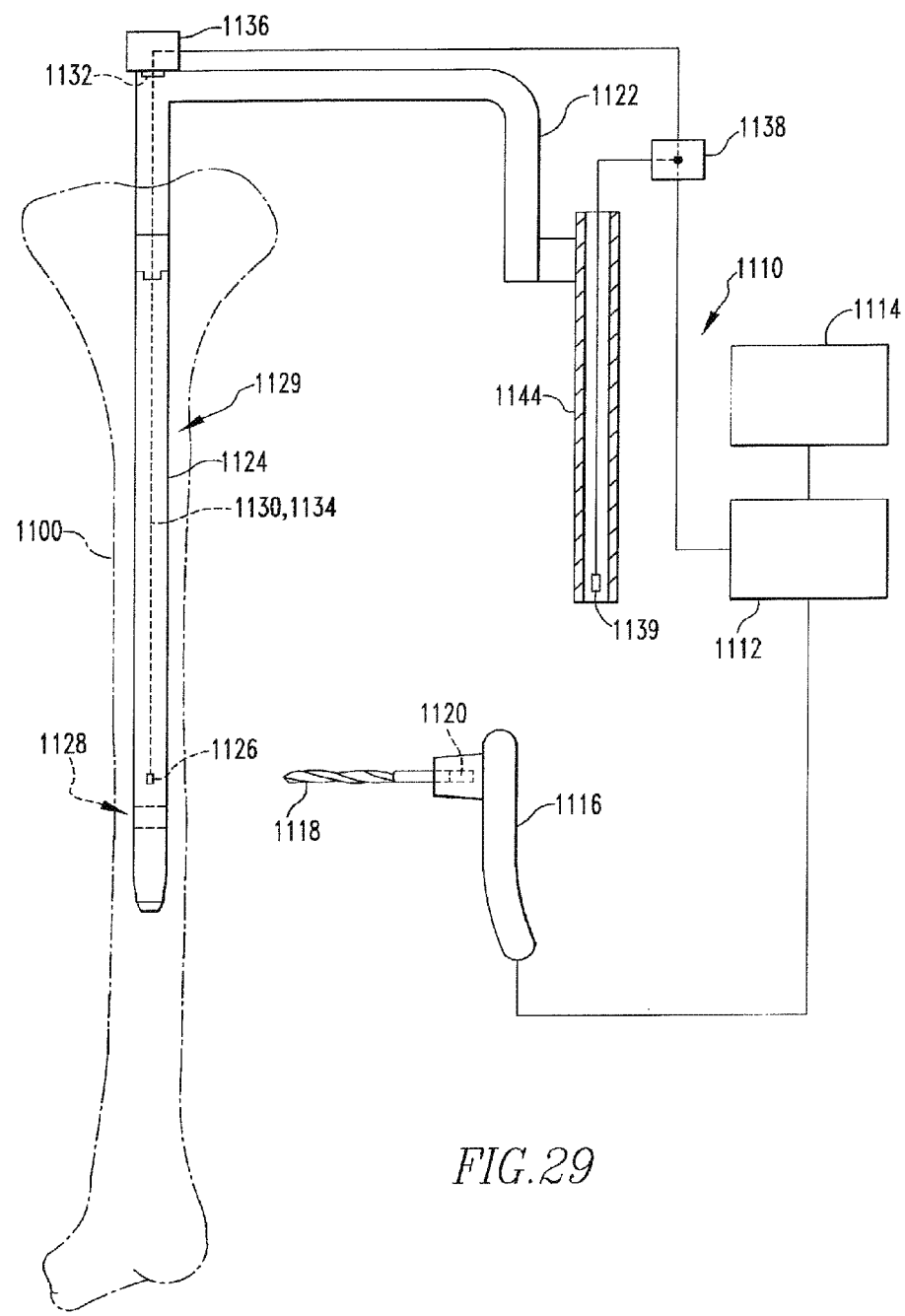
FIG. 29 illustrates yet another disclosed system for identifying a landmark.

FIG. 29 illustrates a system 1110 for identifying a landmark in a fourth implementation. The system 1110 may include a control unit 1112, a field generator 1114, a landmark identifier 1116, an intramedullary nail 1124, a drop 1136, and a probe 1129. The control unit 1112 may be included as part of the processor described above or may be a separate unit. The intramedullary nail 1124 is inserted into the bone 100, and the intramedullary nail 1124 has a hole or landmark 1128. The field generator 1114 is connected to the control unit 1112, either by wire or wirelessly. In the depicted implementation, an insertion handle 1122 is removably attached to the intramedullary nail 1124. The insertion handle 1122 and/or the intramedullary nail 1124 may be formed with a cannulation. The insertion handle 1122 may include a third sensor 1144. The drop 1136 may include a fourth sensor 1139.

The landmark identifier 1116 may include a second sensor 1120. The landmark identifier 1116 may guide a drill bit 1018, and the drill bit 1018 may be connected to a drill (not shown). The second sensor 1120 may be connected to the control unit 1112, either by wire or wirelessly. The field generator 1114 may be included in or on the landmark identifier 1116, in which case, the second sensor 1120 may be omitted.

The probe 1129 may include a wire 1130, a tape 1134, and a stop 1136. As shown below, the probe may be more unitary in structure as well. The tape 1134 may have, in some implementations, a rectangular geometry that assists in orienting the tape as it is placed into a cannulation of the intramedullary nail 1124. The wire 1130 may be operatively connected to the tape 1134. For example, this may be accomplished through the use of an adhesive or fastener. A first sensor 1126 is connected to the control unit 1112, either by wire or wirelessly. The first sensor 1126 is connected through the use of the wire 1130. In some implementations, a detachable connector may be used. The first sensor 1126 may be connected to a distal end of the tape 1134, and the stop 1136 may be connected to a proximal end of the tape 1134. The stop 1136 may be used to control the placement of the sensor 1126. If the tape 1134 is a fixed length and the distance is known from the end of the insertion handle to the landmark 1128, repeatable placement of the first sensor 1126 may be achieved. The tape 1134 may be of sufficient length such that the sensor 1126 is aligned with the landmark 1128, adjacent the landmark 1128, or offset from the landmark 1128.

In use, the intramedullary nail 1124 is placed into the bone 100. The insertion handle 1122 may be attached to the intramedullary nail 1124. The probe 1129 is fed through the insertion handle 1122 and into the intramedullary nail 1124 until the stop 1136 engages the insertion handle 1122. In one particular implementation, the wire 1130 is connected to the control unit 1112, and the sensors 1126, 1120, and 1132 are calibrated using the control unit 1112. The probe 1129 may be removed after calibration. If so, the third sensor 1132 and/or the fourth sensor 1139 and a transformation matrix may be used to identify the relative position of the second sensor 1120 and hence targeter 1116. Optionally, the user may use transfixion elements, such as screws, to first lock the proximal end of the intramedullary nail. An operator uses the landmark identifier 1116 and the first sensor 1126 to identify the landmarks 1128. For example, in the case of intramedullary nail fixation, a surgeon uses the landmark identifier 1116 to identify the blind transfixion holes and drill through the holes for placement of a transfixion element.

Figure 30:
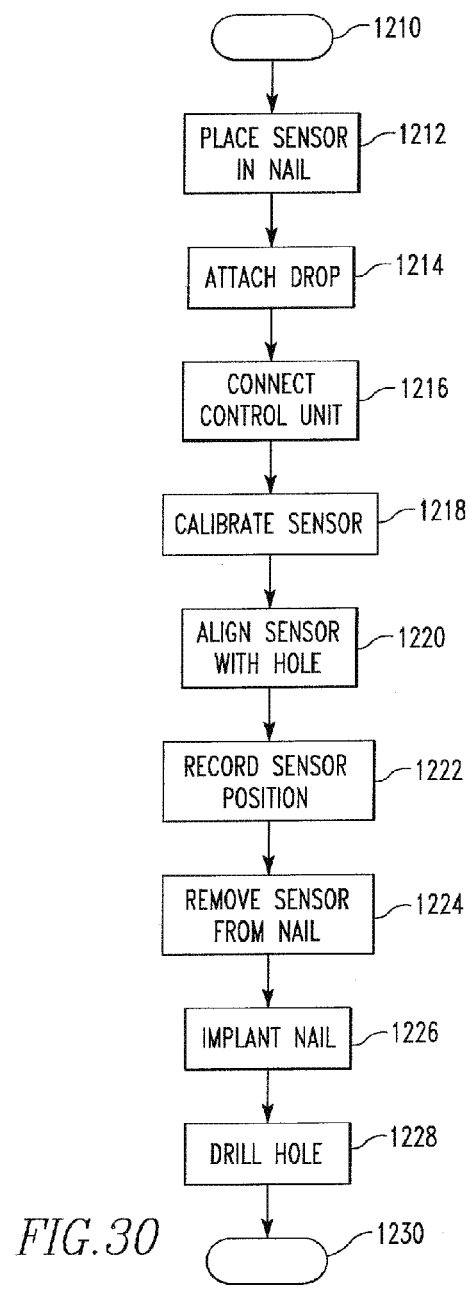
FIG. 30 is a flow chart for using a disclosed landmark identifying system.

FIG. 30 illustrates a first method for using the system to identify a landmark. The method begins at step 1210. In step 1212, the sensor is placed in the nail. In step 1214, the insertion handle is connected to the nail, and the drop is attached to the insertion handle. In step 1216, the control unit is connected to the sensor. In step 1218, the sensor is calibrated. In step 1220, the sensor is aligned with the hole. In step 1222 the sensor position is recorded through the use of the control unit. In step 1224, the sensor is removed from the nail. In step 1226, the nail is implanted into the bone. In step 1228, the hole is drilled using the targeter. The method stops in step 1230.

Figure 31:
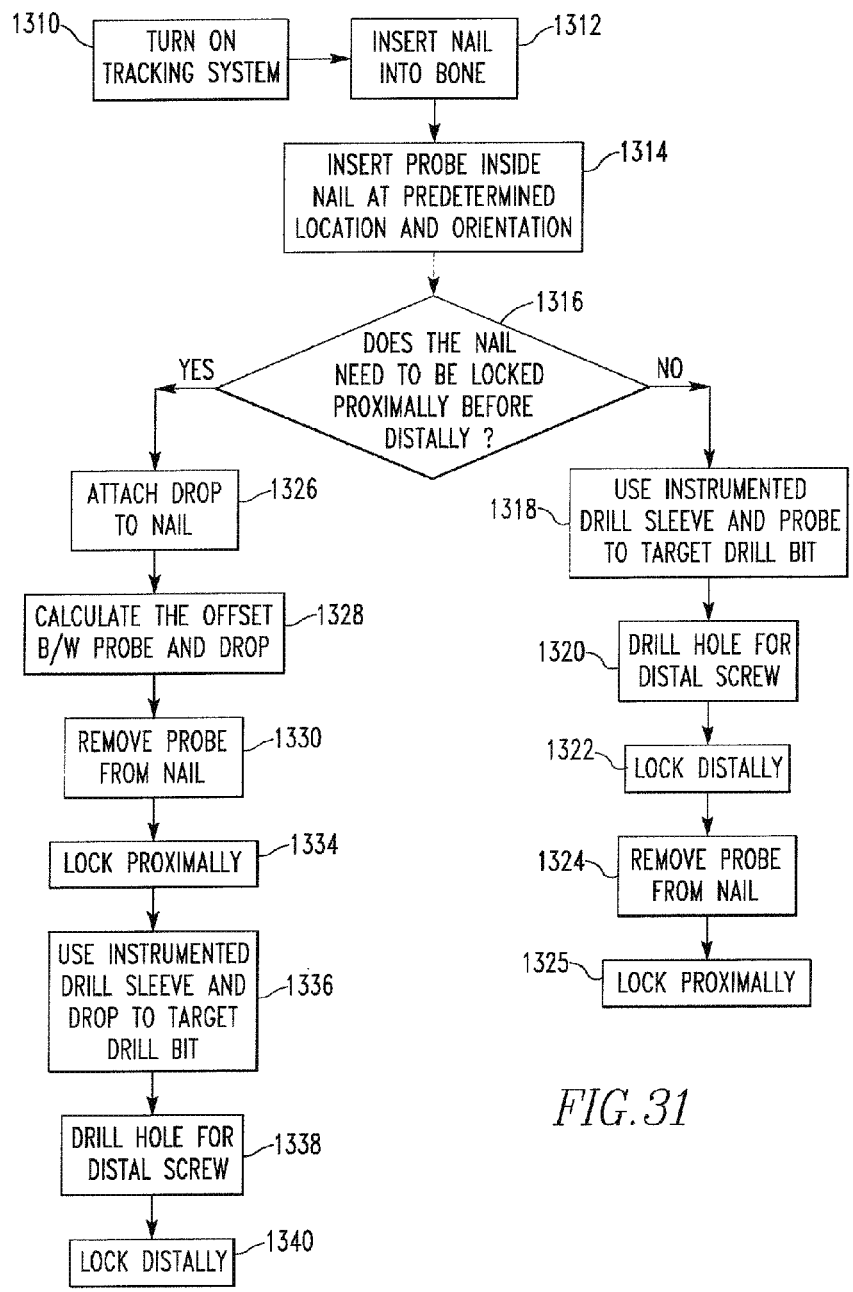
FIG. 31 is another flow chart for using a disclosed landmark identifying system.

FIG. 31 illustrates a second method for using the system to identify a landmark. In step 1310, the tracking system is turned on. In step 1312, the intramedullary nail is inserted into bone. In step 1314, the probe 1129 is inserted into the intramedullary nail canal at a predetermined location and orientation using the stop 1136 and detents spaced along a length of the probe 1129. In step 1316, there is a decision whether the intramedullary nail needs to be locked proximally before distally. If yes, then in step 1326 the drop is attached to the nail. In step 1328, an offset is calculated between the probe and the drop. In other words, a transformation matrix is created. Alternatively, the drop is not connected to the intramedullary but instead a sensor mounted in the insertion handle is used to calculate an offset. In step 1330, the probe is removed from the nail. In step 1334, the nail is locked proximally. This may be accomplished through the use of the landmark identifier, a mechanical jig, or by manual operation. In step 1336, the landmark identifier is used to target the drill. In step 1338, the hole is drilled for the distal screw. In step 1340, the intramedullary nail is locked distally. On the other hand, if the decision is to lock distally first, then in step 1318 the landmark identifier and probe are used to target the drill bit. In step 1320, the hole is drilled for the distal screw. In step 1322, the intramedullary nail is locked distally. In step 1324, the probe is removed from the intramedullary nail. In step 1324, the intramedullary nail is locked proximally. This may be accomplished through the use of the landmark identifier, a mechanical jig, or by manual operation.

Figure 32:
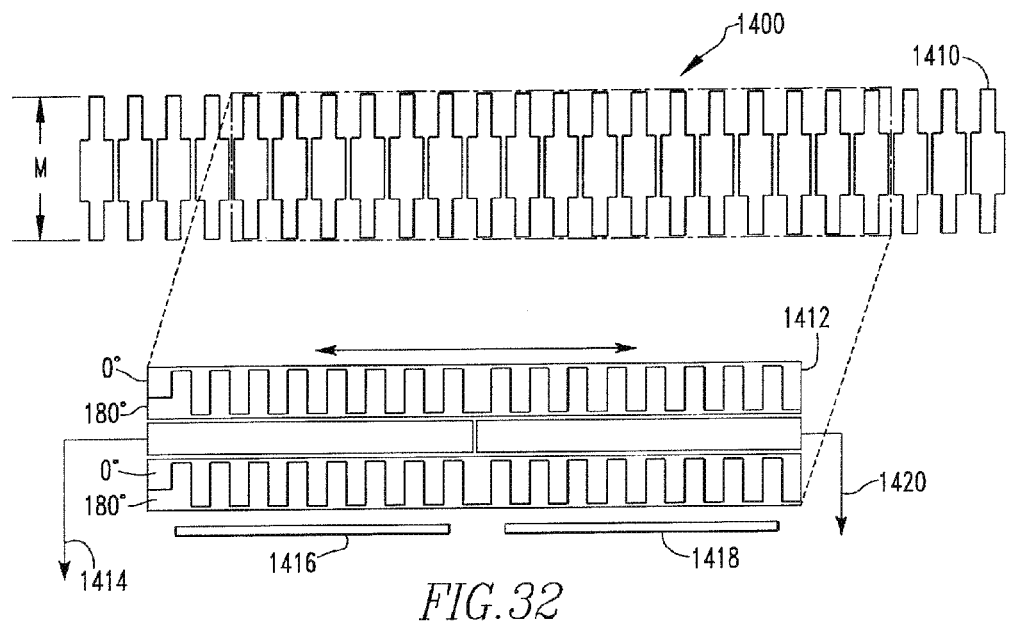
FIG. 32 is a schematic illustration of tracking drill depth.

FIG. 32 illustrates a system for measuring depth of drill bit placement. The system 1400 may include a stator 1410 and a slider 1412. The stator 1410 and the slider 1412 form a capacitive array that can sense relative motion. Moving the stator 1410 and the slider 1412 in a linear relation relative to one another causes a voltage fluctuation that can be interpreted and used to determine the distance traveled. In some implementations, an electronic measuring circuit (not shown) and the slider 1412 may be housed inside the landmark identifier, and the drill bit may be specially constructed to have the stator 1410 along outer surface so that the stator 1410 and the slider 1412 are in very close linear proximity to each other. The linear movement of the drill bit stator 1410 induces a voltage in the receiving slider 1412 which is interpreted by the electronic measuring circuit as a distance measurement. The distance measurement may be sent to the control unit and/or displayed on the monitor. Capacitive sensors are highly susceptible to moisture, and so some implementations may be made to prevent liquids, such as bodily fluids, from traveling between the stator 1410 and the slider 1412. O-rings or some other similar form of wipes can be incorporated within the landmark identifier in order to keep the drill bit substantially moisture free.

Figure 33A:
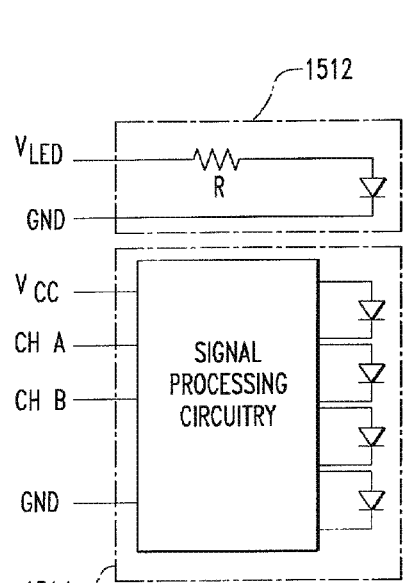
FIGS. 33A and 33B are also schematic illustrations of tracking drill depth.
Figure 33B:
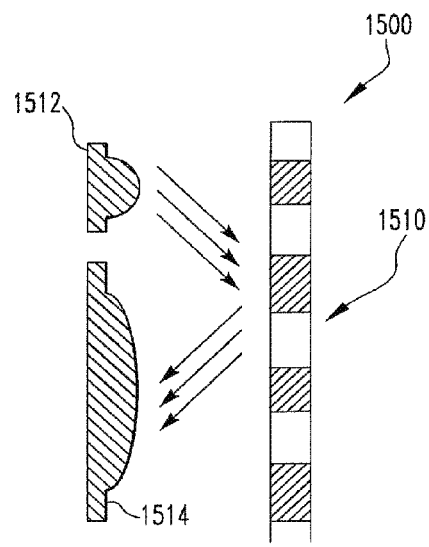

FIGS. 33A and 33B illustrate another system for measuring depth of drill bit placement. The system 1500 may include a reflective code wheel or strip 1510, a lens 1512, and an encoder 1514. The lens 1512 focuses light onto bar of the code strip 1510. As the code strip 1510 rotates, an alternating pattern of light and shadow cast by the window and bar, respectively, falls upon photodiodes of the encoder 1514. The encoder 1514 converts this pattern into digital outputs representing the code strip linear motion. The encoder is an Avago Technologies AEDR-8300 Reflective Optical Encoder available from Avago Technologies of 350 W Trimble Road, San Jose, Calif. Alternatively, the Avago Technologies ADNS-5000 One Chip USB LED-based Navigation System may be used. The encoder and its supporting electronics may be mounted inside the landmark identifier so that its input region is oriented toward a "window" in the landmark identifier cannulation. Markings, such as dark colored concentric rings or bright reflective rings, may be added to the drill bit in order to enhance the visibility of the bit to the encoder. These markings could also be used to denote the starting zero point for measurement. As the drill bit moves linearly within the landmark identifier, the encoder measures the movement of the drill bit. The distance measurement may be sent to the control unit and/or displayed on the monitor.

Figure 34:
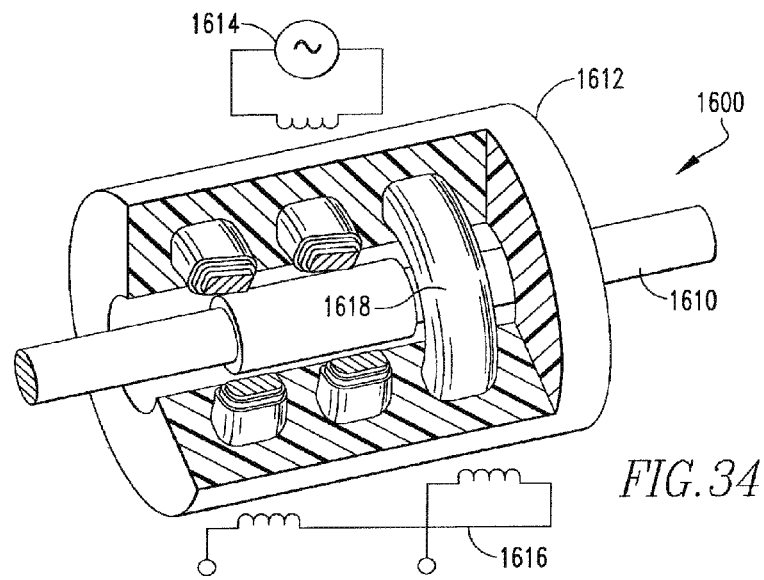
FIG. 34 is a partial illustration of a disclosed device for tracking drill depth.

FIG. 34 illustrates yet another system for drill depth measurement. The system 1600 utilizes a Linear Variable Differential Transformer (LVDT) 1612. An LVDT is a type of electrical transformer used to measure linear displacement. The LVDT 1612 may include a plurality of solenoid coils 1618 placed end-to-end around a tube 1610, which is the landmark identifier in the depicted implementation. In FIG. 34, the center coil is the primary coil and the outer two coils are the secondary coils. A cylindrical ferromagnetic core 1610, such as the drill bit, slides along the axis of the tube. An alternating current 1614 is driven through the primary coil, causing a voltage to be induced in each secondary proportional to its mutual inductance with the primary. A pickup sensor 1616 measures the magnitude of the output voltage, which is proportional to the distance moved by the core (up to its limit of travel). The phase of the voltage indicates the direction of the displacement. Because the sliding core does not touch the inside of the tube, it can move without friction, making the LVDT a highly reliable device. The absence of any sliding or rotating contacts allows the LVDT to be completely sealed against the environment. The distance measurement may be sent to the control unit and/or displayed on the monitor.

Figure 35:
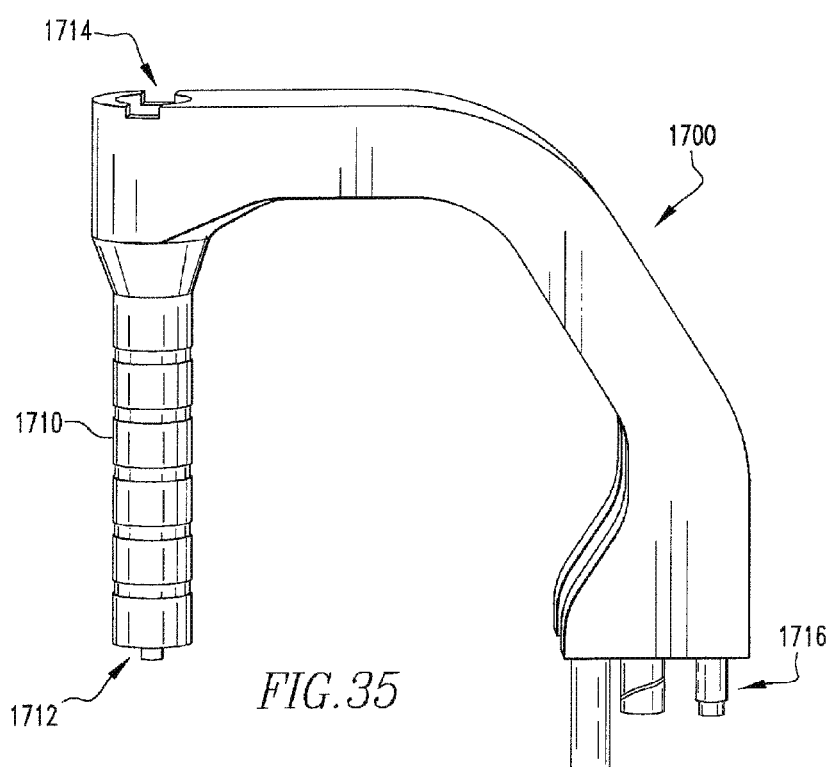
FIG. 35 is a perspective view of another insertion handle.
Figure 36:
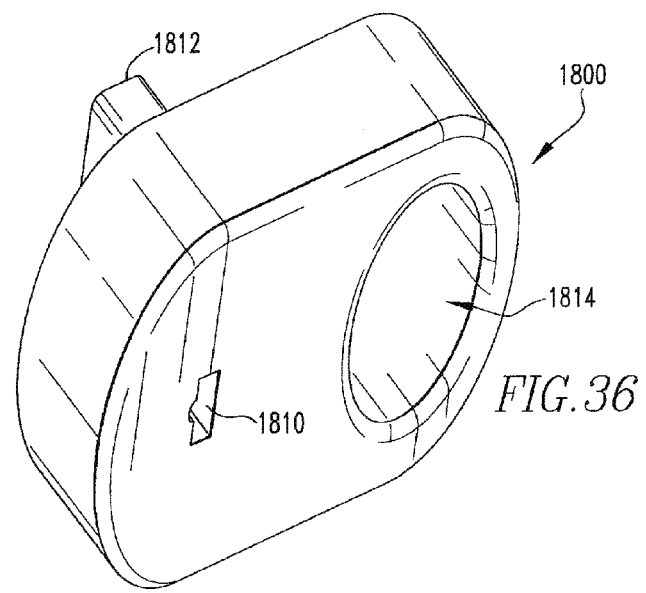
FIG. 36 is a top perspective view of an adjustable stop.
Figure 37:
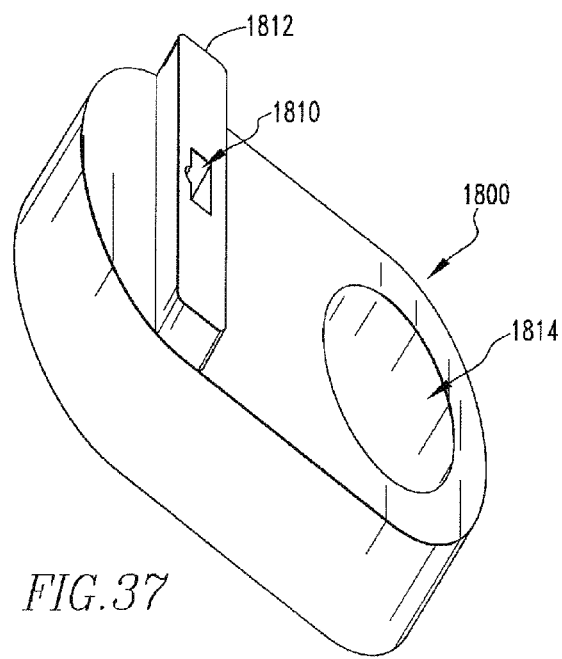
FIG. 37 is a bottom perspective view of the adjustable stop illustrated in FIG. 36.
Figure 38:
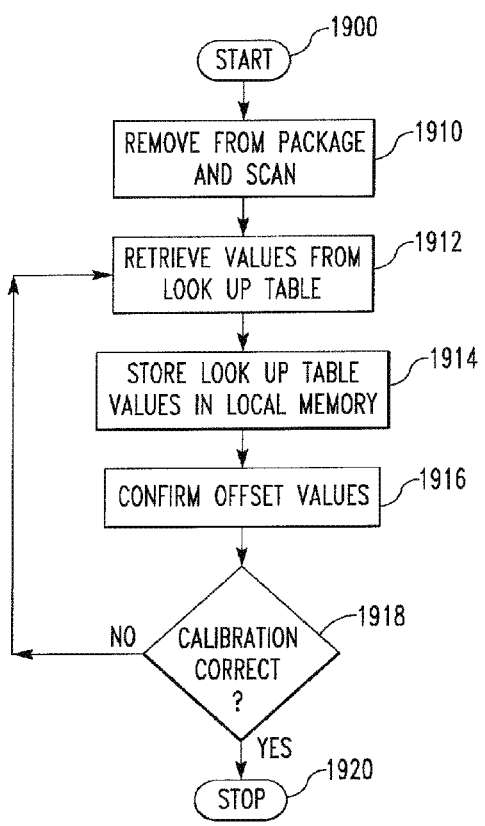
FIG. 38 is another illustrating system calibration.

FIGS. 35-37 illustrate an insertion handle 1700 (FIG. 35) and an adjustable stop 1800 (FIGS. 37-38). The insertion handle 1700 a stem 1710 that connects to an implant, such as an intramedullary nail (not shown), at an end portion 1712. The insertion handle 1700 may include a quick connect 1716 for attachment to a drop, proximal targeting device, or some other instrument or apparatus. The insertion handle may include a top portion 1714, which may include a hole and/or an alignment feature. The adjustable stop 1800 may include a slot 1810, an alignment member 1812, and a fastener hole 1814.

In FIGS. 35-37, the adjustable stop 1800 may be removably attached to the top portion 1714 of the handle 1700. The adjustable stop may be integrally formed with the insertion handle 1700. In yet other implementations, the adjustable stop may be permanently attached to the insertion handle 1700. The alignment member 1812 fits within an alignment feature of the top portion to prevent rotation of the adjustable stop. A fastener (not shown) may be placed through the fastener hole 1814 to attach the adjustable stop to the insertion handle 1700. The tape 1034, 1134 may be placed through the slot 1810, through the stem 1710, and into the intramedullary nail cannulation. The slot 1810 may have a shape to match the geometry of the tape and/or probe 1129 to aid in its insertion or to prevent rotation of the tape. The tape 1034, 1134 or probe 1129 may include markings, graduations, or detents to indicate an appropriate depth for the given nail length. The adjustable stop 1800 may include a locking mechanism (not shown) to temporarily lock the tape 1034, 1134 at a particular depth. In its simplest form, the locking mechanism may be a fastener that frictionally engages the tape 1034, 1134.

FIG. 38 illustrates a method for calibrating the system for identifying a landmark. Calibration is necessary for accuracy. The method begins at step 1900, which may include powering up the system. In step 1910, the probe and the landmark identifier are removed from packaging, if any, and scanned. The drop is also scanned. Scanning may include reading a bar code using a bar code reader. Scanning causes the system to retrieve offset sensor values that correspond to the bar code from a look up table in step 1912. The look up table may be local or accessed over a network, such as the Internet. Alternatively, the probe and the landmark identifier may include a serial number or other unique identifier, and the unique identifier is used in conjunction with the look up table to retrieve offset sensor values. The offset sensor values are stored in local memory of the system in step 1914. In step 1916, the user places the probe relative to the implant and attempts to track a landmark using the landmark identifier in step 1916. In step 1918, there is a decision whether the calibration is correct. If so, the method ends in step 1920. Otherwise, new offset values are retrieved in step 1912.

Figure 39:
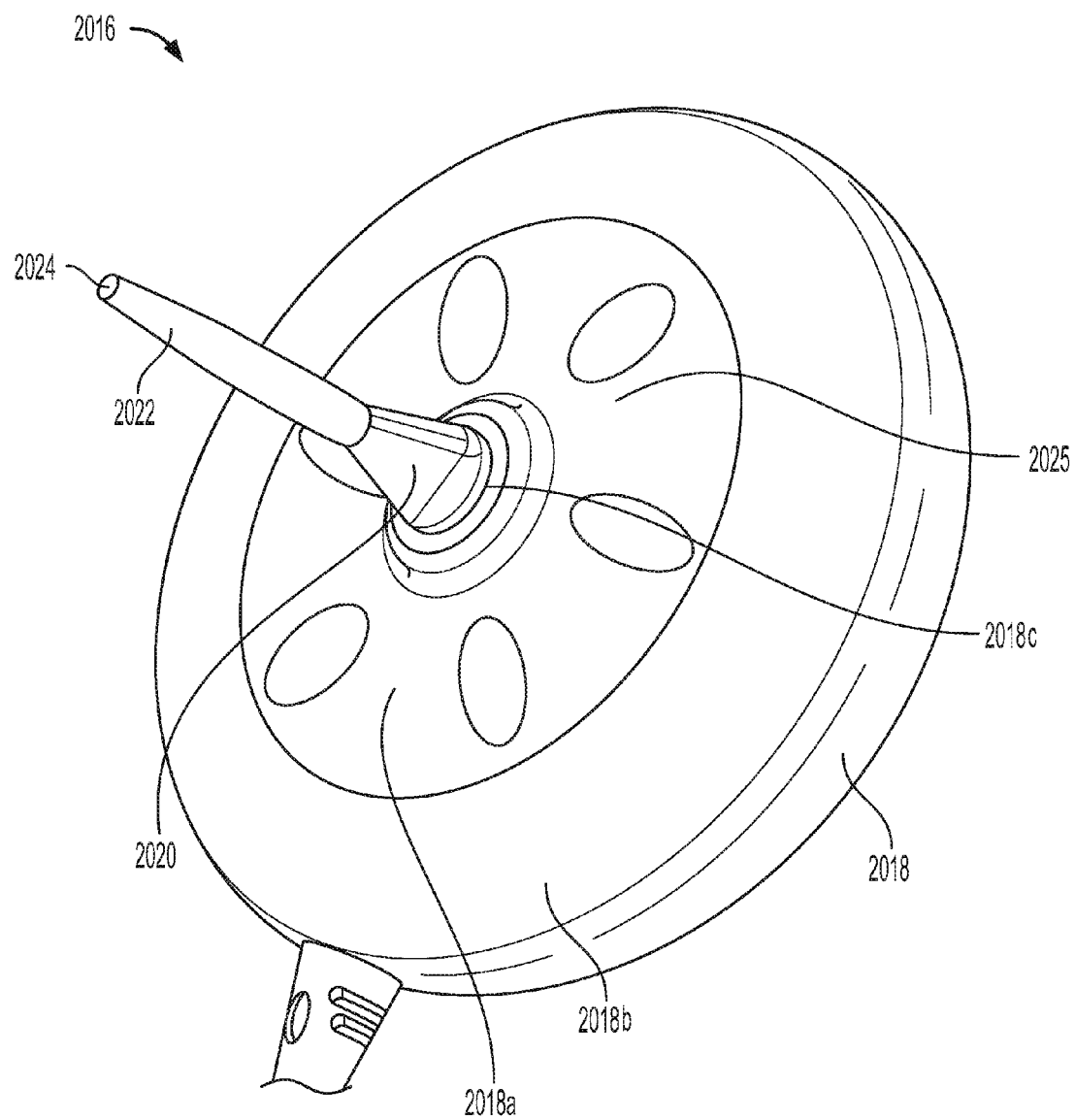
FIG. 39 is a perspective view of another landmark identifier housing a field generator and a drill sleeve and that may be sterilized or subject to an autoclave procedure.

FIG. 39 illustrates an implementation combining a landmark identifier, a field generator and a drill sleeve. The handheld landmark identifier 2016 houses an electromagnetic field generator (not shown) which may include one or more induction coils or other elements to create a suitable electromagnetic field or fields. The electromagnetic field generator is mounted in or on an autoclavable material and encapsulated in a silicone housing body 2018 that may be easily sterilized, and which is removably engageable with a tool. The relative orientation and position of the induction coils or elements in the landmark identifier 2016 may be selected to optimize the balance between the qualities and strength of the electromagnetic field or fields and their interaction with the sensor and the weight, size, form factor and ergonomics of the identifier 2016. At least three induction coils (not shown) may be mounted in or on the autoclavable material.

The autoclavable material allows the landmark identifier 2016 to be sterilized or autoclaved multiple times without degradation of the autoclavable material, internal components, or operational performance. For example, the housing 2018 includes an internal body or mounting structure (not shown) on which the coils and/or other electromagnetic field generating components are mounted. The internal body is formed of a material that does not adversely interfere with a generated electromagnetic field and which can be subjected to sterilization processes, including autoclaving. For example, the internal body can be formed from a glass-reinforced epoxy laminate, such as a NEMA grade G-11 glass reinforced epoxy laminate (VETRONITE G11) or equivalent. The internal body is surrounded by a first covering 2018a formed from a first material, such as an overmolding of VMQ silicone material #71385C available from Minnesota Rubber & Plastics, 1100 Xenium Lane N., Minneapolis, Minn. 55441. The housing 2018 also includes a second covering 2018b that may provide an additional layer of protection or insulation at an outer edge of the housing 2018. The second covering 2018b may be formed from a second material, such as an overmolding of VMQ silicone material #71325C available from Minnesota Rubber & Plastics, 1100 Xenium Lane N., Minneapolis, Minn. 55441. The housing 2018 also includes a coupling member 2018c that passes through the internal body and that engages one or more attachable components. The coupling member 2018c may be formed from polysulfone, such as a GEHR PPSU polyphenylsulfone RAL 9005 Black (Solvay Radel R-5500) or equivalent, and can be at least partially covered by the first covering 2018a.

The particular landmark identifier 2016 illustrated in FIG. 39 may also include a removable drill sleeve attachment 2020 and a drill sleeve 2022 with a serrated tip 2024, though different components and constructions can be included as mentioned elsewhere. The sleeve attachment 2020 and drill sleeve 2022 can be formed as a single unit or as separate units connected to each other by adhesives or other connection means known to one skilled in the art. For illustration purposes, the sleeve 2022 as illustrated in FIG. 39 is a drill sleeve, but it can also be a larger size sleeve such as a screw driver sleeve or other sleeves as selected by the surgeon, or other components as disclosed herein. To change sleeves or other components, the surgeon unscrews the sleeve attachment and replaces it with another sleeve attachment of choice and its corresponding sleeve.

Figure 40:
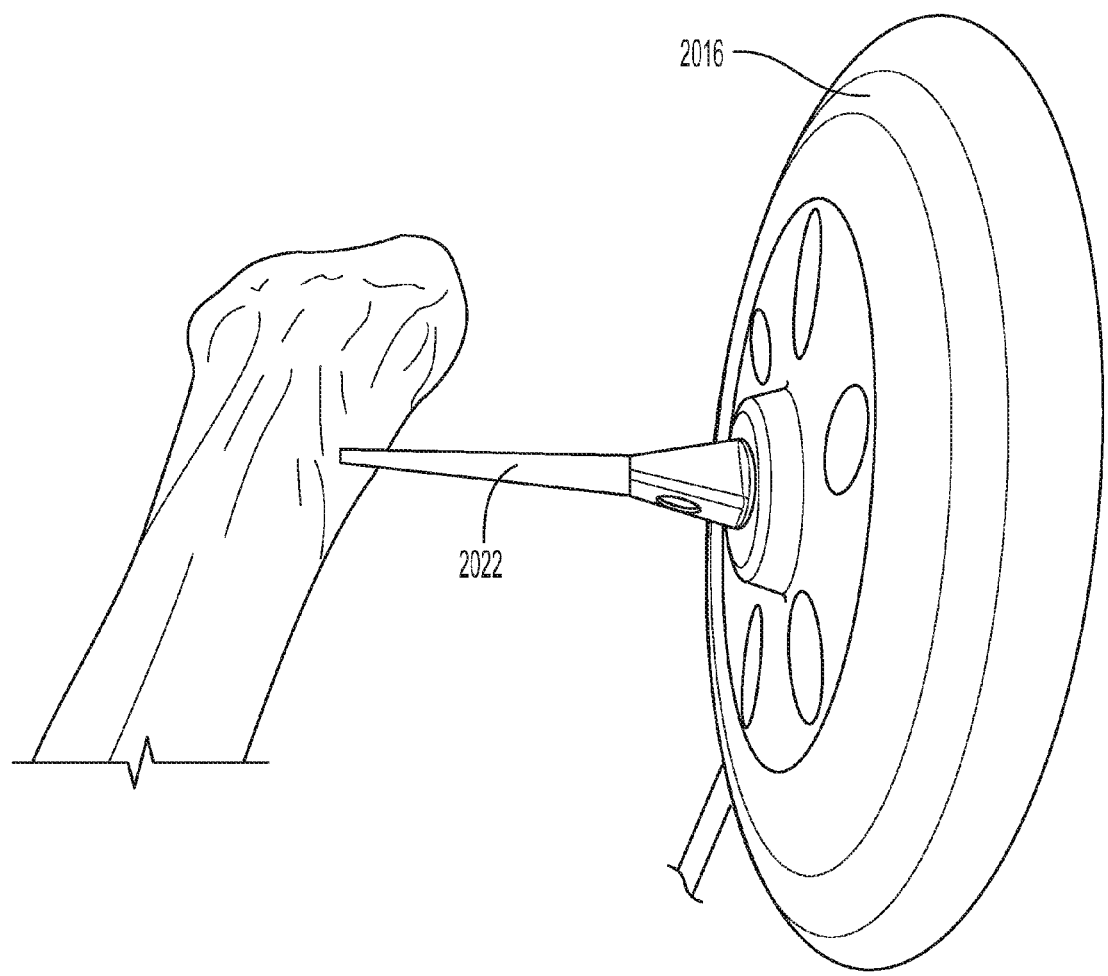
FIG. 40 is a side view of the landmark identifier/field generator/drill sleeve of FIG. 39 making contact with a bone.
Figure 41:
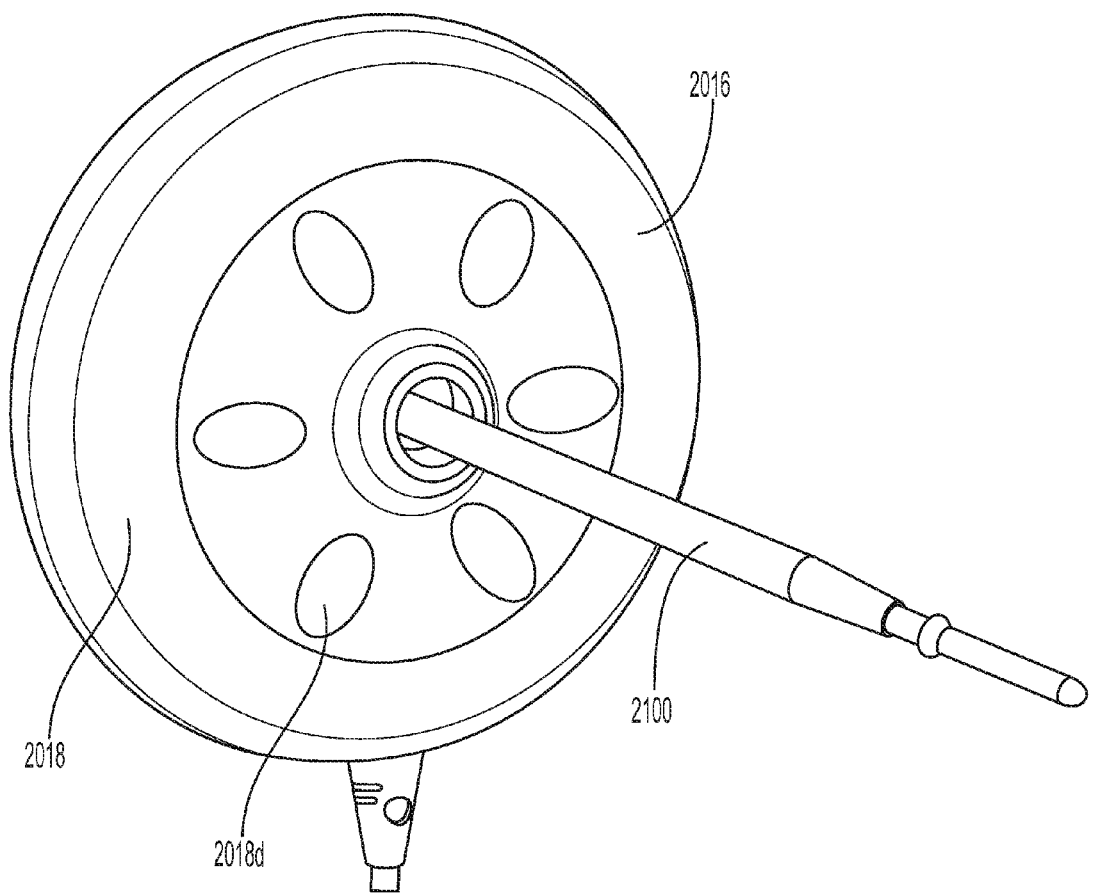
FIG. 41 is a perspective view of the landmark identifier/field generator/autoclavable housing of FIG. 39 coupled to a screw driver attachment.

Unlike the landmark identifier 18 illustrated in FIG. 9, the landmark identifier 2016 depicted in FIGS. 39-40 does not require the second sensor 20 illustrated in FIG. 9 because the origin of the global space (the area in which the electromagnetic field is generated) can be defined within the landmark identifier 2016. One axis of the global space co-ordinate system can be the longitudinal axis of the drill sleeve or other component 2022. In that situation, the other two axes of the global space co-ordinate system can be defined by planes orthogonal to that longitudinal axis and to each other. Advantages of incorporating the field generator into the landmark identifier 2016 include a smaller size field generator because it can be brought into the local working space (area which may include the landmarks such as implant holes that are to be targeted for screw placement) therefore requiring a smaller electromagnetic field. The global space and local working space become the same or at least correspond more closely spatially when the landmark identifier 2016 with its field generator brought into the vicinity of the landmark, implant or probe sensor (not shown). Because the electromagnetic field size requirement is smaller, the induction coils within the field generator can be smaller which therefore reduces the size and weight of the handheld field generator to make it more manageable for handheld usage. A light may be provided in an area of the landmark identifier/field generator/drill 2016, such as the area 2025 to indicate to the user that power is being supplied to the landmark identifier/field generator/drill 2016. In FIG. 41, the drill sleeve 2022 has been removed and the landmark identifier 2016 has been engaged with a screw driver 2100 for fixing the implant to the bone. As shown in FIG. 41, the housing 2018 of the landmark identifier 2016 may include one or more indentations 2018d for finger placement to allow the user to comfortably place his or her hand around the landmark identifier 2016. In the implementation depicted in FIG. 41, there are six indentations. Additionally, the texture and dimension of an exterior surface of the housing 2018 can be configured allow a user to comfortably and securely grip the housing 2018. Additionally, or alternatively, the landmark identifier 2016 can be attachable to a tool, such as a housing of the screw driver 2100.

The material selection for the landmark identifier 2016 of FIG. 39 which houses the field generator can be optimized for weight and stability after multiple autoclave cycles. Any autoclavable material can be used, and the materials are preferably non-magnetic or weak magnetic to avoid or minimize interference with the electromagnetic fields. Exemplary materials include ceramic, autoclavable polymers such as polypropylene (PP), polypropylene copolymer (PPCO), polycarbonate (PC), polymethylpentene (PMP), polytetrafluoroethylene (PTFE) resin, polymethyl methacrylate (PMMA or acrylic), ethylene tetrafluoroethylene (ETFE), ethylene chlorotrifluoroethlyene (ECTFE), fluoro ethylene propylene (FEP), polyether imide (PEI), perfluoroalkoxy (PFA), polyketone (PK), polyphenylene oxide (PPO), polysulfone (PSF), polyvinyl chloride (PVC), polyvinylidene fluoride (PVDF), silicone, or thermoplastic elastomers (TPE), and still other autoclavable materials which will be apparent to those skilled in the art, including combinations of the above.

Figure 42:
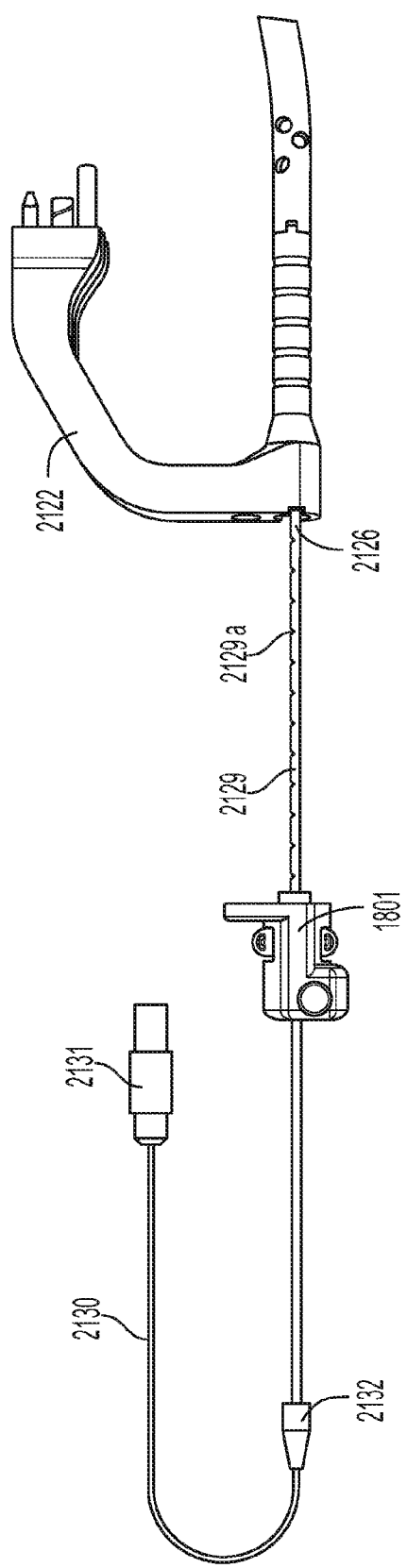
FIG. 42 is a plan view of an insertion handle, adjustable stop and probe.
Figure 43:
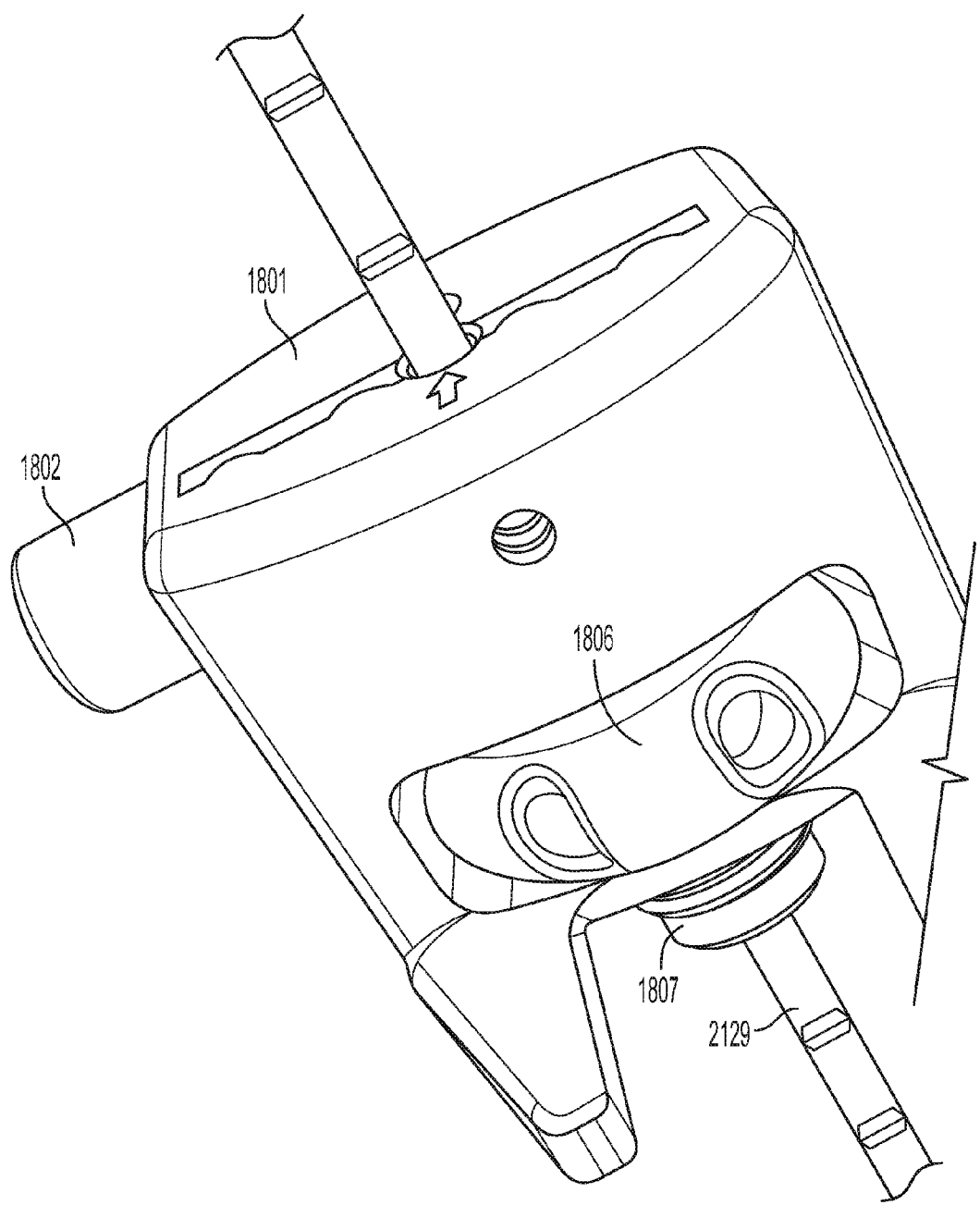
FIG. 43 is a perspective view of an exemplary adjustable stop to hold a probe in a desired position.
Figure 44:
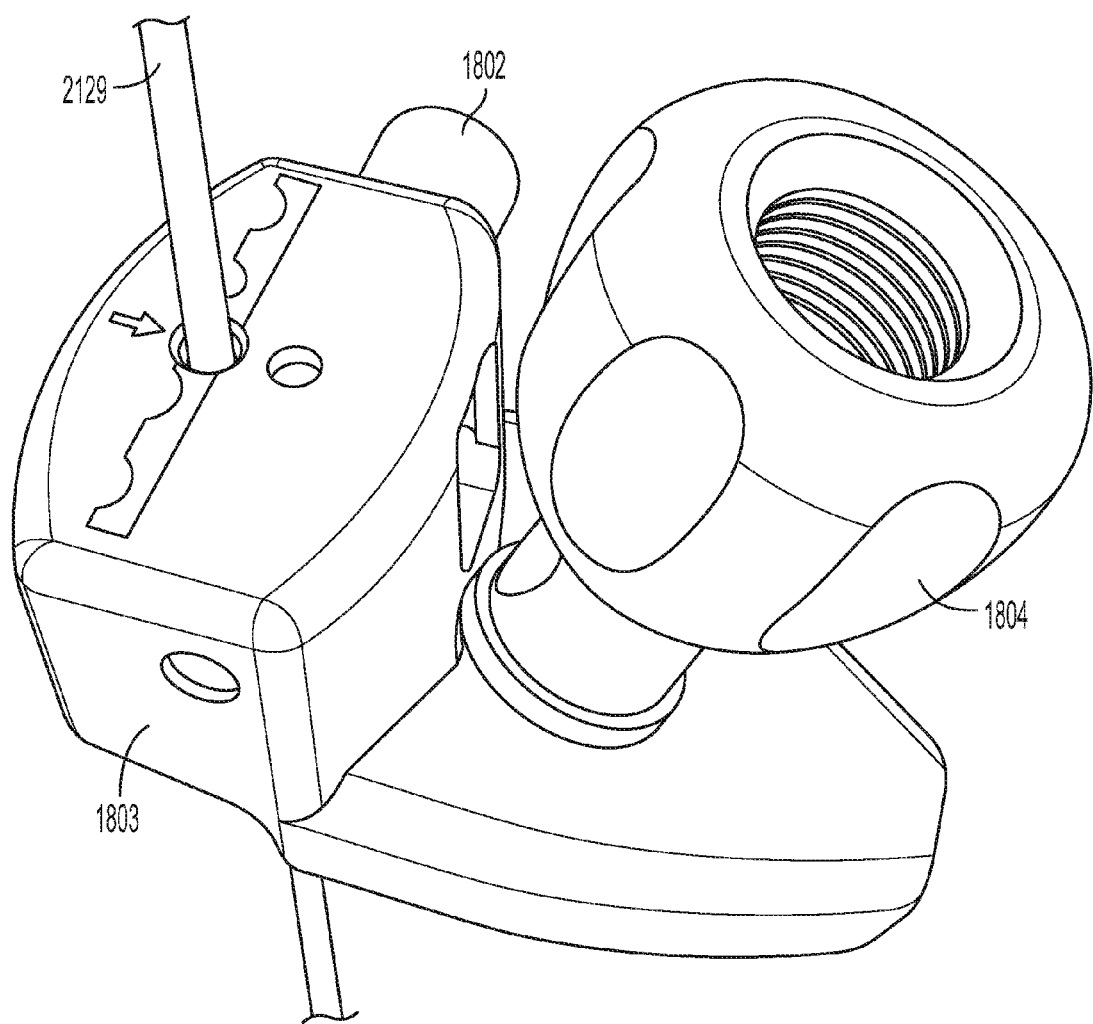
FIG. 44 is a perspective view of another exemplary adjustable stop.
Figure 58:
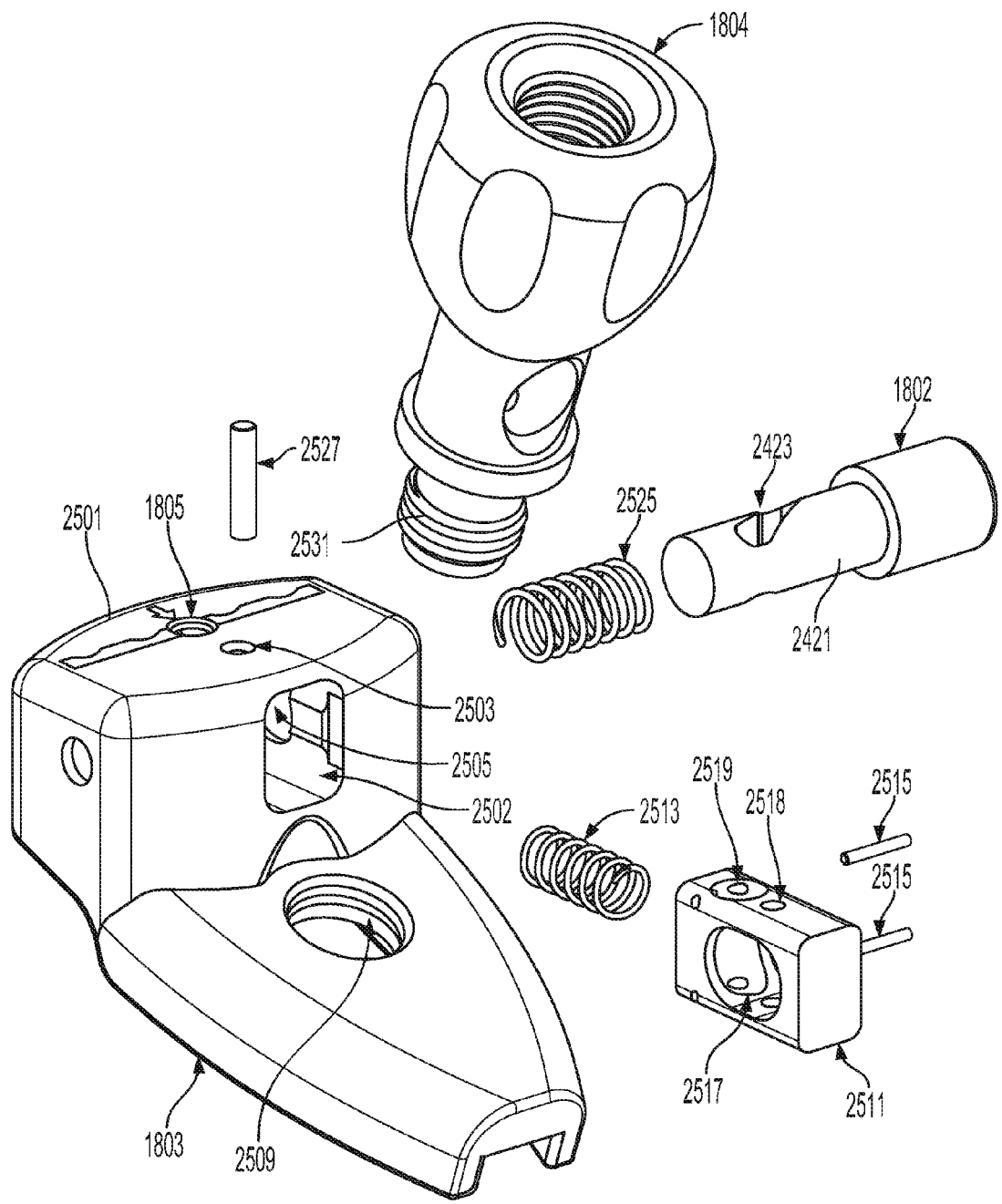
Figure 59:
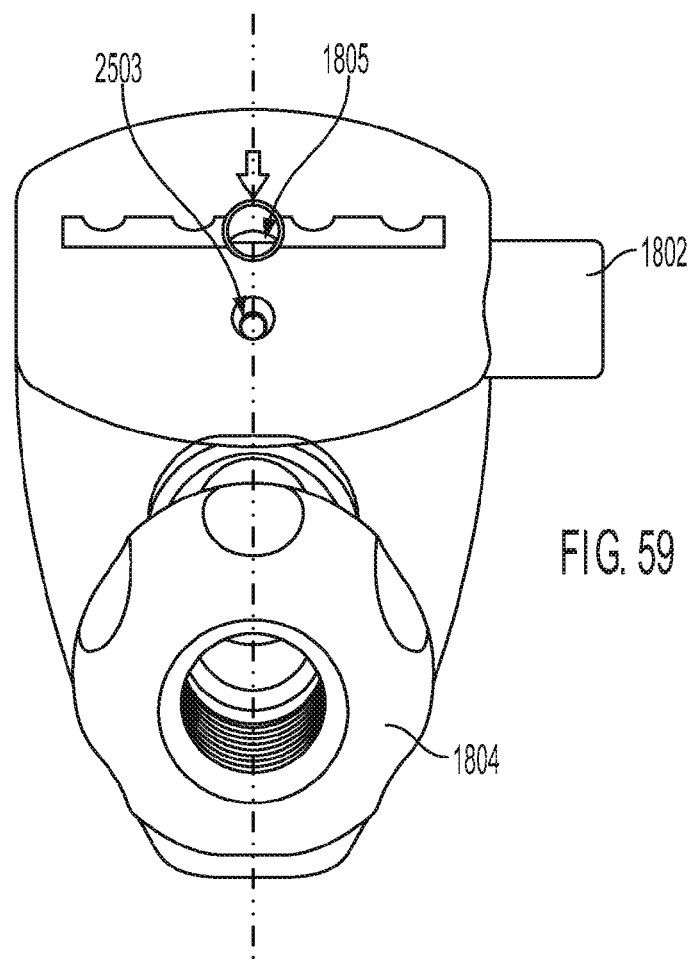
Figure 60:
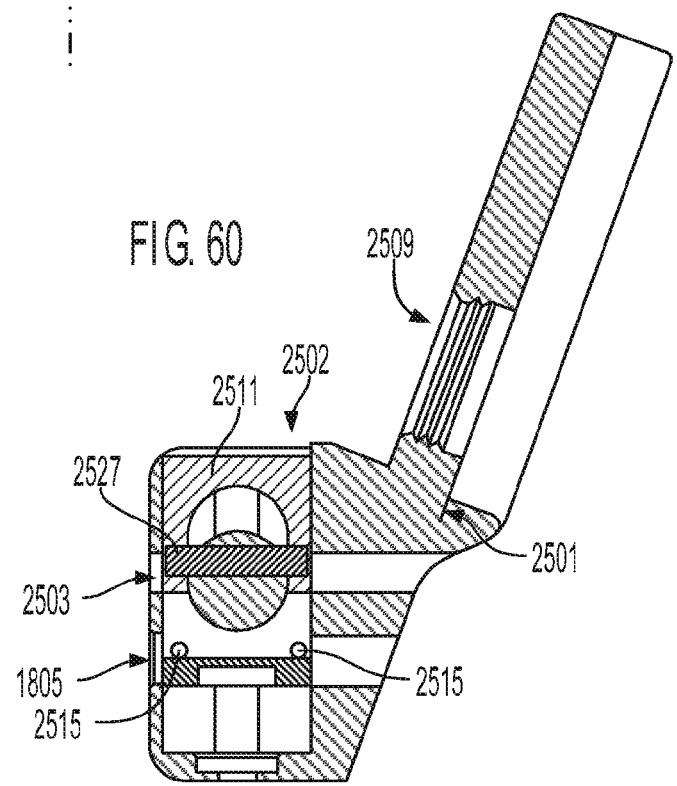
Figure 61:
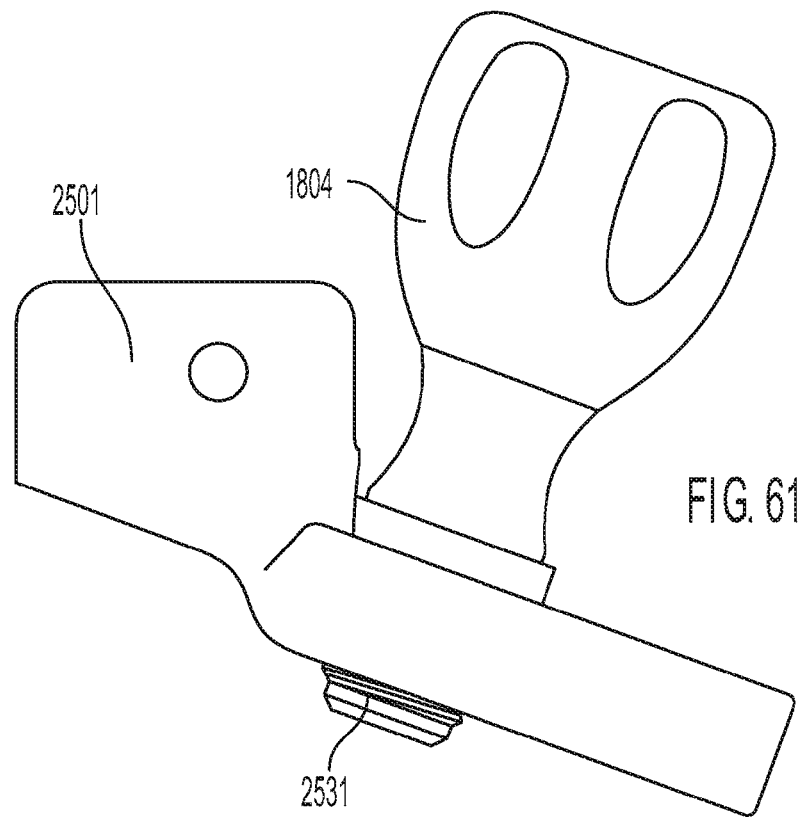
Figure 62:
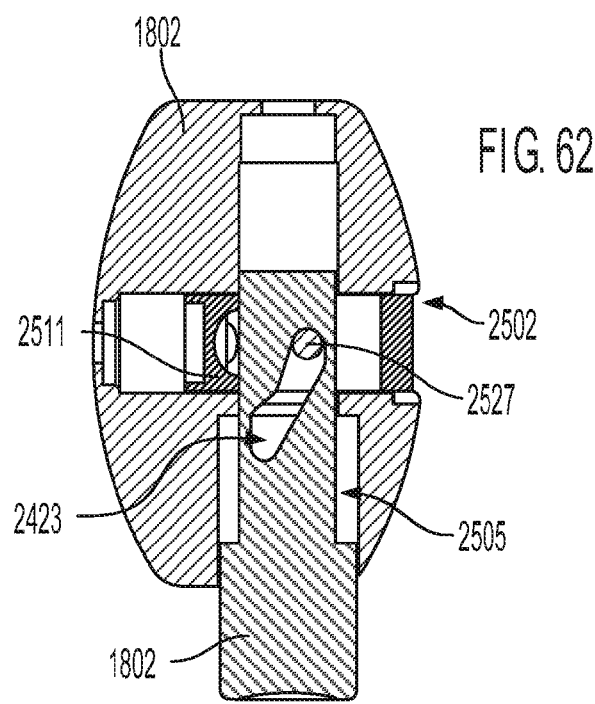

FIG. 42 illustrates another insertion handle 2122, an adjustable stop 1801, a probe 2129 and a sensor 2126 located within or on a body 2129a of the probe 2129. The insertion handle 2122 is removably attached to an orthopaedic implant, such as an intramedullary nail. The probe 2129 includes a cable 2130 and a connector 2131 for connection to a processor for use in targeting landmarks of the intramedullary nail, or other implant. The probe 2129 also includes a grip 2132 that secures the cable 2130 to the body 2129a to prevent tension forces applied to the cable 2130 from damaging the sensor 2126 and/or the electrical connection between the sensor 2126 and the cable 2130. The adjustable stop 1801 and an alternative stop 1803 are also illustrated in FIGS. 43 and 44. The stop 1801 and the stop 1803 each include a push button actuator 1802. The stop 1801 includes a thumb wheel 1806 that is used to turn a threaded bolt 1807 for attaching the stop 1801 to an insertion handle while the stop 1803 includes a knob clamp 1804 that is also connected to a threaded bolt 2531 (FIG. 58). The probe 2129 may be equipped with detents or markings to assist the user in placing the probe 2129 and sensor 2126 in the correct position.

The system may include different stops, such as stops 1801, 1803, depending upon the particular surgical approach contemplated. For example, the surgical approach in the case of retrograde placement of an intramedullary nail may utilize the stop 1801, whereas antegrade place placement of an intramedullary nail may favor use of the stop 1803. Other surgical approaches may yet require other variations.

Figure 45:
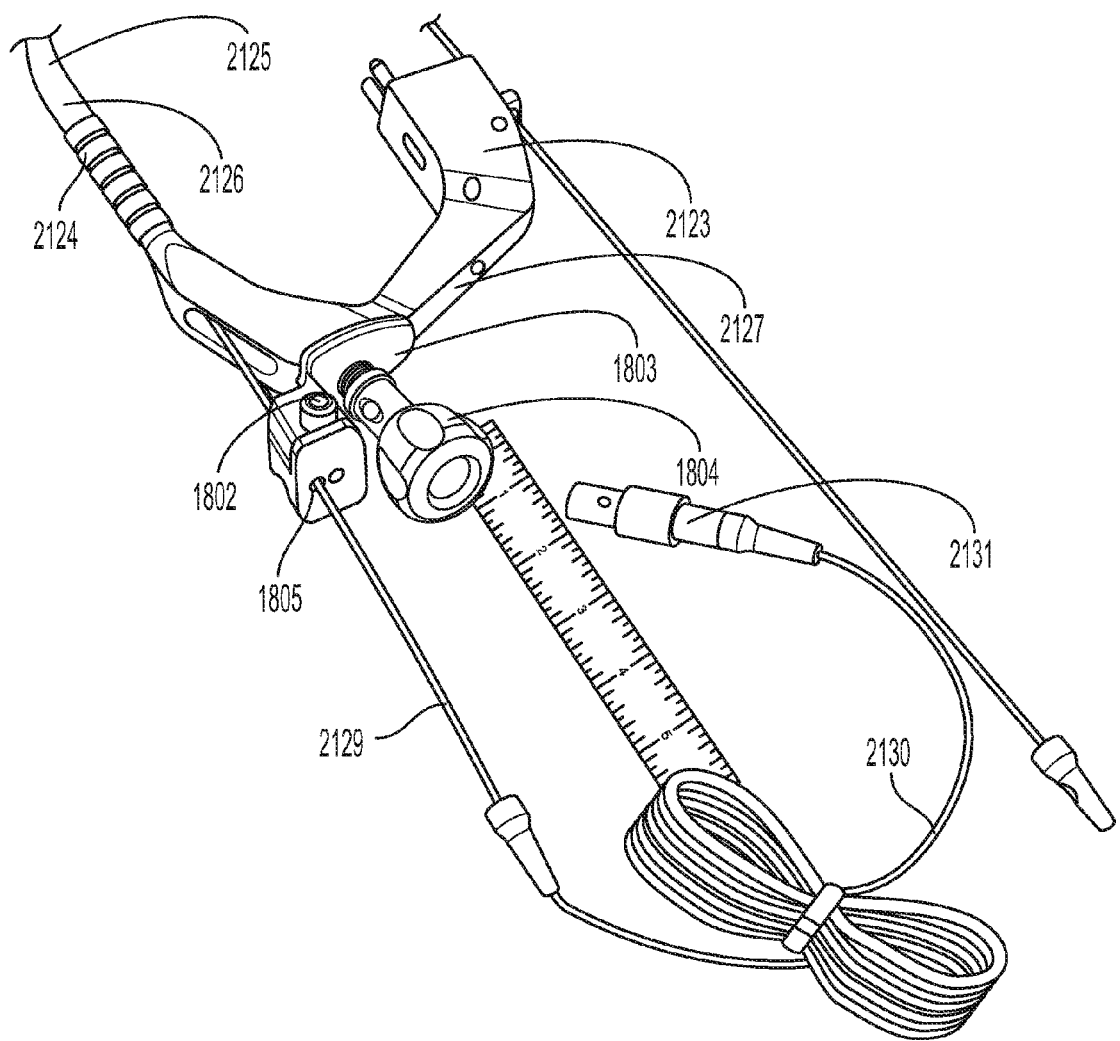
FIG. 45 is a perspective view of an intramedullary nail, an insertion handle, an adjustable stop, and a probe.

Now referring to FIG. 45, the adjustable stop 1803, an insertion handle 2123, and the probe 2129 are illustrated in an assembled configuration attached to an intramedullary nail 2125. A distal portion 2124 of the insertion handle 2123 is attached to a proximal head 2126 of the intramedullary nail 2125. The insertion handle 2123 is connected to the intramedullary nail 2125 through the use of a cannulated bolt (not shown). Alternatively, the insertion handle 2123 can be connected to the intramedullary nail 2125 using a quick-connect mechanism, or other attachment device.

The adjustable stop 1803 is attached to a proximal surface 2127 of the insertion handle 2123. The adjustable stop 1803 has a complimentary mating portion such that when the stop 1803 is connected to the insertion handle 2123, the stop 1803 is located or fixed relative to the insertion handle 2123 within three degrees of freedom. The probe 2129 is inserted through a hole 1805 of the adjustable stop 1803, through the distal portion 2124 of the insertion handle 2123, through the cannulated bolt, and into a cannulation (not shown) of the intramedullary nail 2125. The probe 2129 includes the sensor 2126 (FIG. 42) located proximate a distal end (not shown). The sensor 2126 (FIG. 42) is electrically connected to the cable 2130 that includes the connector 2131 for transmitting signals from the sensor 2126 (FIG. 42) to a control unit (not shown).

Figure 46:
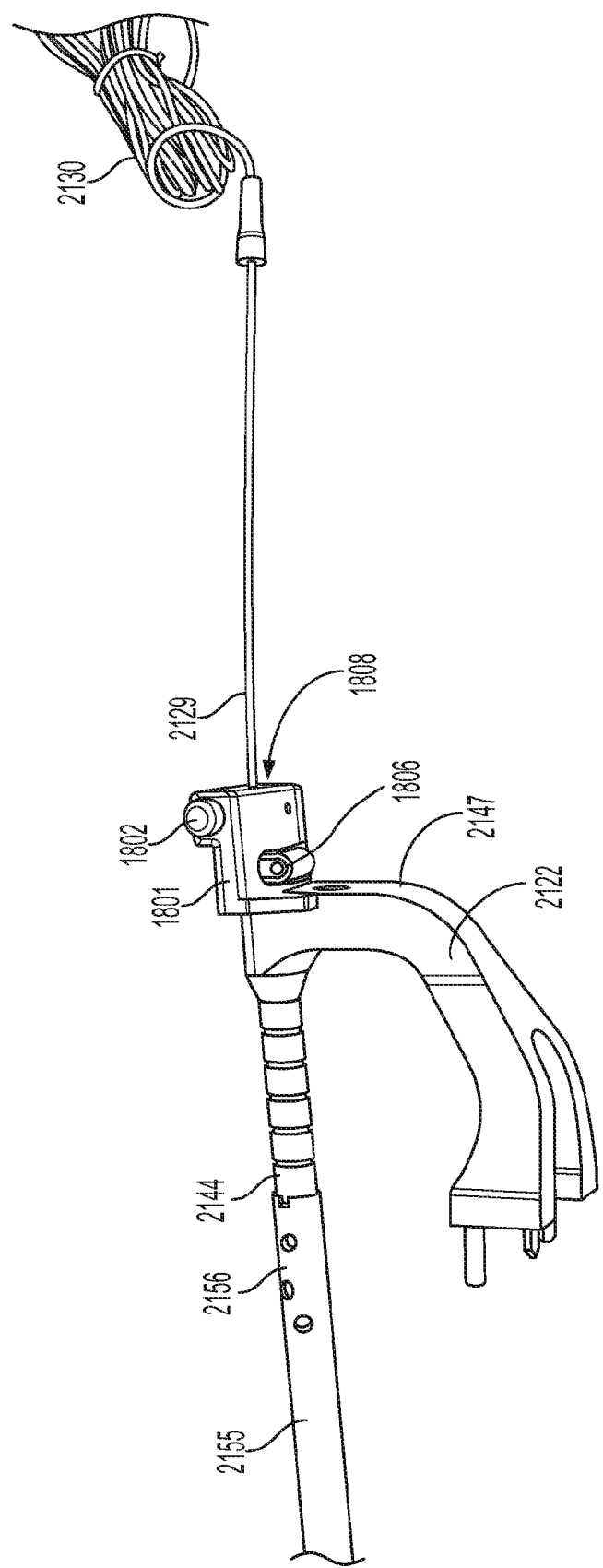
FIG. 46 is a perspective view of another intramedullary nail, an insertion handle, an adjustable stop, and a probe.

FIG. 46 shows the adjustable stop 1801, the insertion handle 2122, and the probe 2129 in an assembled configuration attached to an intramedullary nail 2155. The adjustable stop 1801 is mounted to a proximal surface 2147 of the insertion handle 2122 by rotating the thumb wheel 1806 to thread the bolt 1807 (FIG. 43) into a threaded connection (not shown) formed in the insertion handle 2122. The adjustable stop 1801 has a complimentary mating portion such that when the stop 1801 is connected to the insertion handle 2122, the stop 1801 is located or fixed relative to the insertion handle 2122 within three degrees of freedom. A distal portion 2144 of the insertion handle 2122 is attached to a head 2156 of the intramedullary nail 2155. For example, the insertion handle 2122 is connected to the intramedullary nail 2125 through the use of a cannulated bolt (not shown). The probe 2129 is inserted through a hole 1808 of the adjustable stop 1801, through the distal portion 2144 of the insertion handle 2122, through the cannulated bolt, and into the head 2156 of the intramedullary nail 2155.

Figure 47:
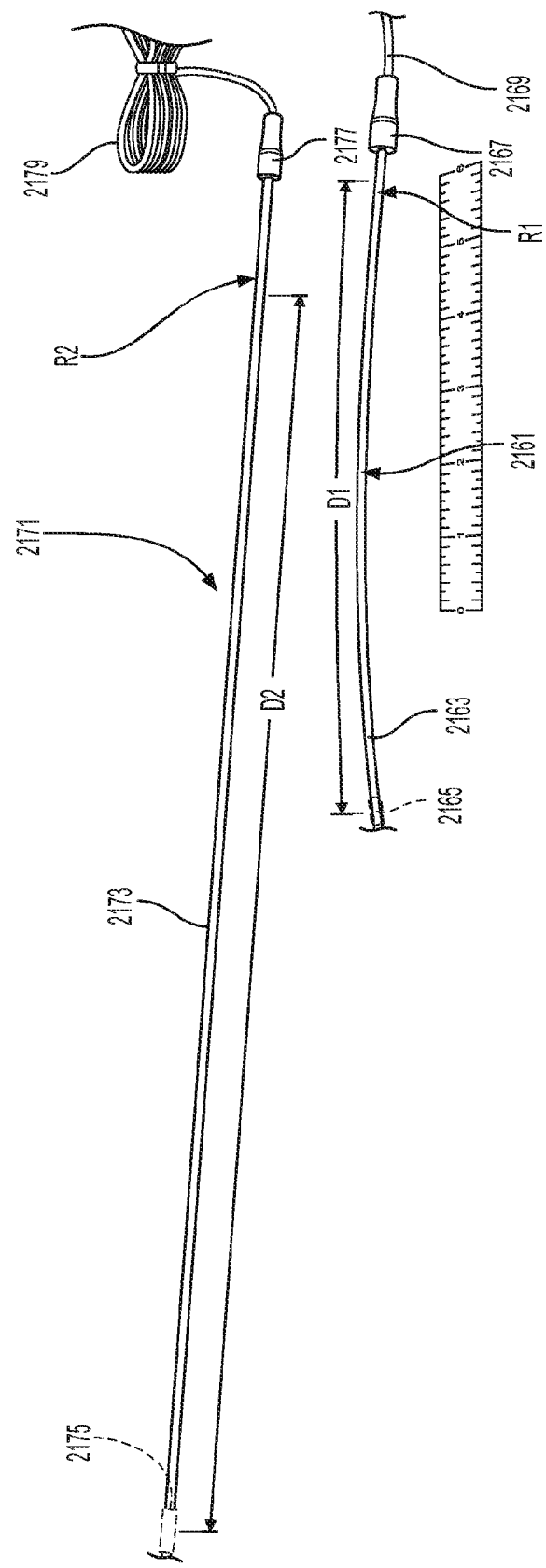
FIG. 47 is a perspective view of two probes for use in targeting landmarks of an implant.

Now referring to FIG. 47, a proximal targeting probe 2161 and a distal targeting probe 2171 are illustrated. The proximal targeting probe 2161 includes a tape body 2163 and a sensor 2165 disposed within or on the tape body 2163 at a predetermined distance D1 from a reference point R1 of the body 2163. The proximal targeting probe 2161 also includes a color-coded grip 2167 that indicates that the probe 2161 is to be used for targeting proximal landmarks of an orthopaedic implant, such as the intramedullary nail 2155 of FIG. 46 and a cable 2169 for carrying a signal from the sensor 2165 to a control unit (not shown). The distal targeting probe 2171 includes a tape body 2173 that is longer than the body 2163 of the proximal targeting probe 2161. A sensor 2175 is included within or on the tape body 2173 at a second predetermined distance D2 from a reference point R2 of the body 2173. The distal targeting probe 2171 also includes a color-coded grip 2177 that is a different color than the grip 2167 and that indicates that the probe 2171 is to be used for targeting distal landmarks of an orthopaedic implant, such as the intramedullary nail 2155 of FIG. 46. A cable 2179 is included to transmit a signal from the sensor 2175 to a control unit (not shown). The tape body 2163 of the proximal targeting probe 2161 and/or the tape body 2173 of the distal targeting probe 2171 may have, in some implementations, a rectangular geometry that assists in orienting the tape body as it is placed into a cannulation of the intramedullary nail. An oval, square, or circular geometry also may be used. In some implementations, the tape body 2163 and the tape body 2173 may be a hollow metal tube. Instead of color-coded grips, in some implementations, each of the sensors 2165 and 2175 is connected to a Programmable Read-Only Memory (PROM) microchip that stores the calibration offset values and also stores an identifier that identifies whether the probe is used for proximal or distal targeting. In that way, when the sensors 2165 and 2175 are both connected to a processor, such as the processor 2327 of FIG. 51, the processor automatically identifies the type of targeting contemplated and may display such information on a display device, such as the display 2326.

The tape body 2163 and the tape body 2173 may include one or more bends to bias at least a portion of the tape body 2163 and the tape body 2173 against the wall of the cannulation of the orthopaedic implant. Biasing a portion of the tape body against the wall of the cannulation increases the repeatability of locating the sensors 2165 and 2175 relative to landmarks. Alternatively, the probes 2161 and/or 2171 could be formed having dimensions approximately equal to dimensions of the cannulation of the intramedullary nail or other implant with which they are intended to be used so that the proper location of the sensor within the cannulation can be repeatably achieved.

Figure 48:
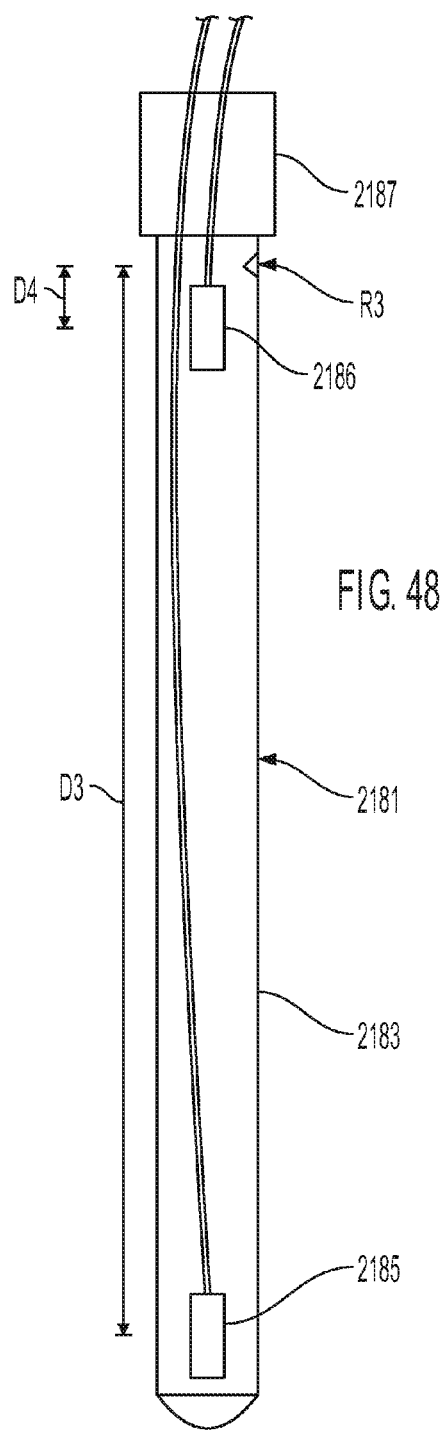
FIG. 48 is a perspective view of another probe for use in targeting landmarks of an implant.

With reference to FIG. 48 and as an alternative to the pair of probes illustrated in FIG. 47, a targeting probe 2181 can be used to target both distal and proximal landmarks of an orthopaedic implant. The probe 2181 is tubular and made from a non-magnetic metal, such as stainless steel. The probe 2181 includes a tape body 2183, a first sensor 2185 disposed within a distal portion of the tape body 2183 and a second sensor 2186 disposed within a proximal portion of the tape body 2183. The first sensor 2185 is located at a distance D3 from a reference point R3 of the body 2183, which may be formed as a notch or detent, and the second sensor is located at a second distance D4 from the reference point R3.

In use, the first sensor 2185 is used to target a distal landmark of an orthopaedic implant, such as a distal locking aperture of an intramedullary nail, and the second sensor 2186 is used to target a proximal landmark of the orthopaedic implant, such as a proximal locking aperture of the orthopaedic nail. In some implementations, the construction of the probe 2181 can be similar to the distal targeting probe 2171 (FIG. 47), with the addition of the second sensor 2186. The probe 2181 also includes a grip 2187, which can be color-coded to be distinguishable from the distal targeting probe 2171, and to indicate that the probe 2181 can be used to target both distal and proximal landmarks of an implant. As discussed above, each of the sensors 2185 and 2186 can be connected to a PROM or other storage device that stores reference values for use in determining a position of a landmark identifier, such as the landmark identifier 2016, relative to a landmark of an implant. The PROMs also store identifiers that allow a processor to determine whether a received signal was generated by the distal sensor 2185 or the proximal sensor 2186.

Figure 49:
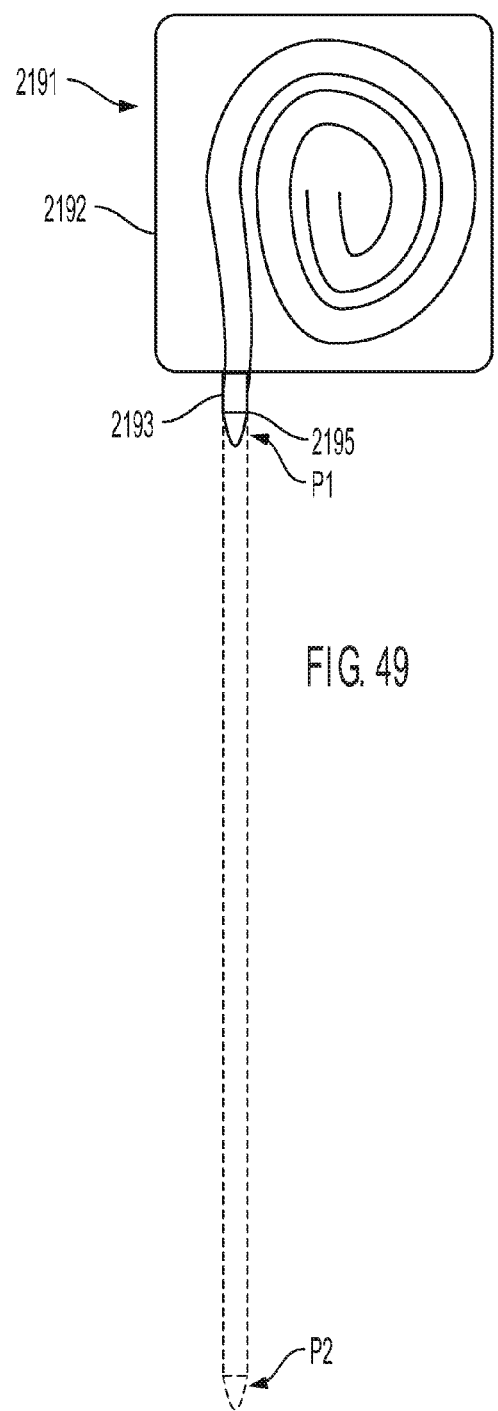
FIG. 49 is a sectional view of a retractable probe.

Another alternative probe 2191 is illustrated in FIG. 49. The probe 2191 includes a housing 2192 and a retractable/extensible body 2193 that can be coiled within the housing 2192. A sensor 2195 disposed within the body 2193 can be positioned at a first position P1 for targeting a proximal landmark of an implant, and can be positioned at a second position P2 for targeting a distal landmark of an implant. In some implementations, the body 2193 can be formed as a concave metal strip that tends to maintain a generally straight shape when extended from the housing, but can also be coiled within the housing 2192. For example, the body 2193 may consist of layered, flexible stainless steel bi-stable spring bands that, when straightened, create tension within the springy metal bands to maintain a generally straight orientation, but coil within the housing 2192 when the tension is relieved. However, other types of materials can be used to form the body, including resilient plastic or rubber tubing or sheeting. Another alternative is to form the body 2192 from nested segments of tubing that can extend and retract by sliding within adjacent tube segments. The probe 2191 can include a rotary encoder, an optical device, or other measuring device or method to determine a length of the body 2193 that is currently extending from the housing 2192. The determined length can be used to determine whether the sensor 2195 is positioned at a desired position, such as the first position P1 or the second position P2.

Figure 50:
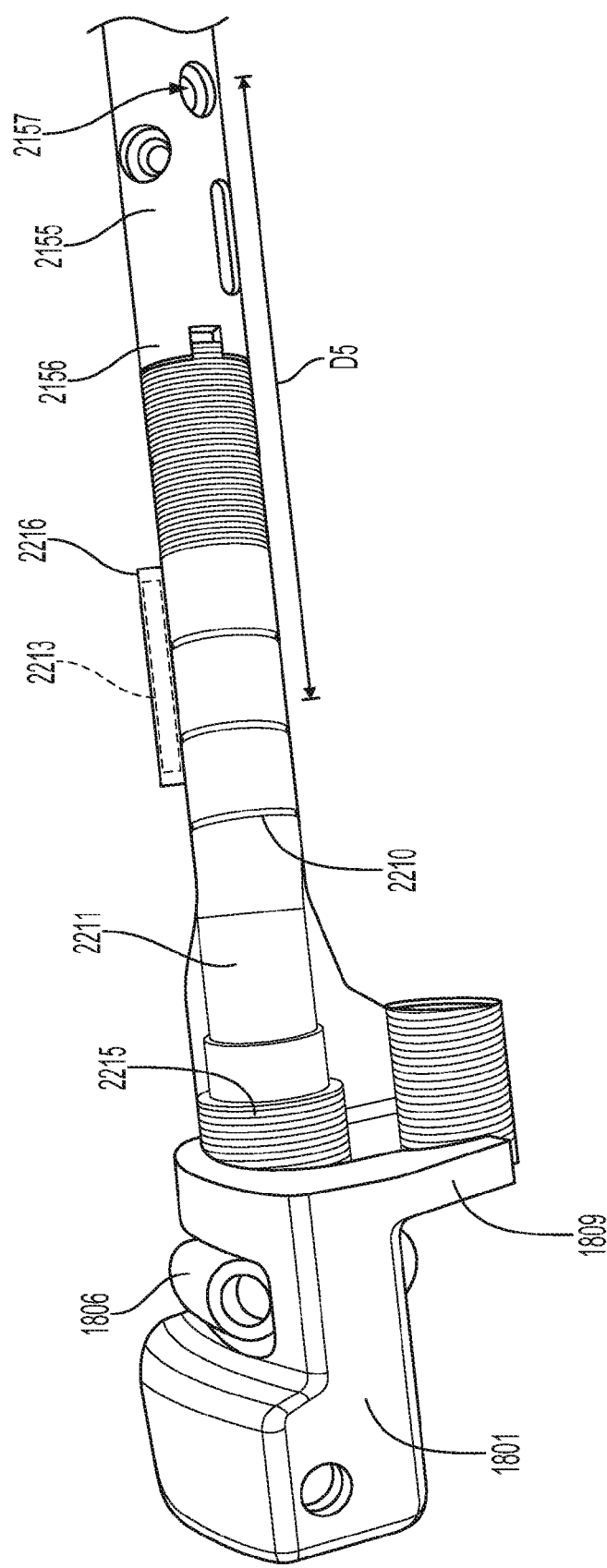
FIG. 50 is a perspective view of an intramedullary, an insertion handle, and an adjustable stop.

Now referring to FIG. 50, the adjustable stop 1801 is mounted to an alternative insertion handle 2210. The insertion handle 2210 includes a body 2211 that is engaged with the head 2156 of the intramedullary nail 2155 (also shown in FIG. 46). As an example, a cannulated bolt (not shown)

may be used to connect the insertion handle 2210 to the head 2156. The insertion handle 2210 includes a sensor 2213 for use in targeting a proximal landmark of the nail 2155, such as a proximal locking aperture 2157. The sensor 2213 is located within or on the body 2211 at a predetermined distance D5 from the proximal locking aperture 2157 when the insertion handle is attached to the nail 2155. The sensor can be passive, or electrically powered by an internal battery (not shown) or an external power supply (not shown). The sensor 2213 may be mounted in a compartment that is unitary or integral with the body 2211, such as the exterior compartment 2216. Alternatively, the sensor 2213 can be located in an internal compartment 2213*a*, shown in FIG. 51. The insertion handle 2210 is made of plastic, but other materials could alternatively be used.

Figure 51:
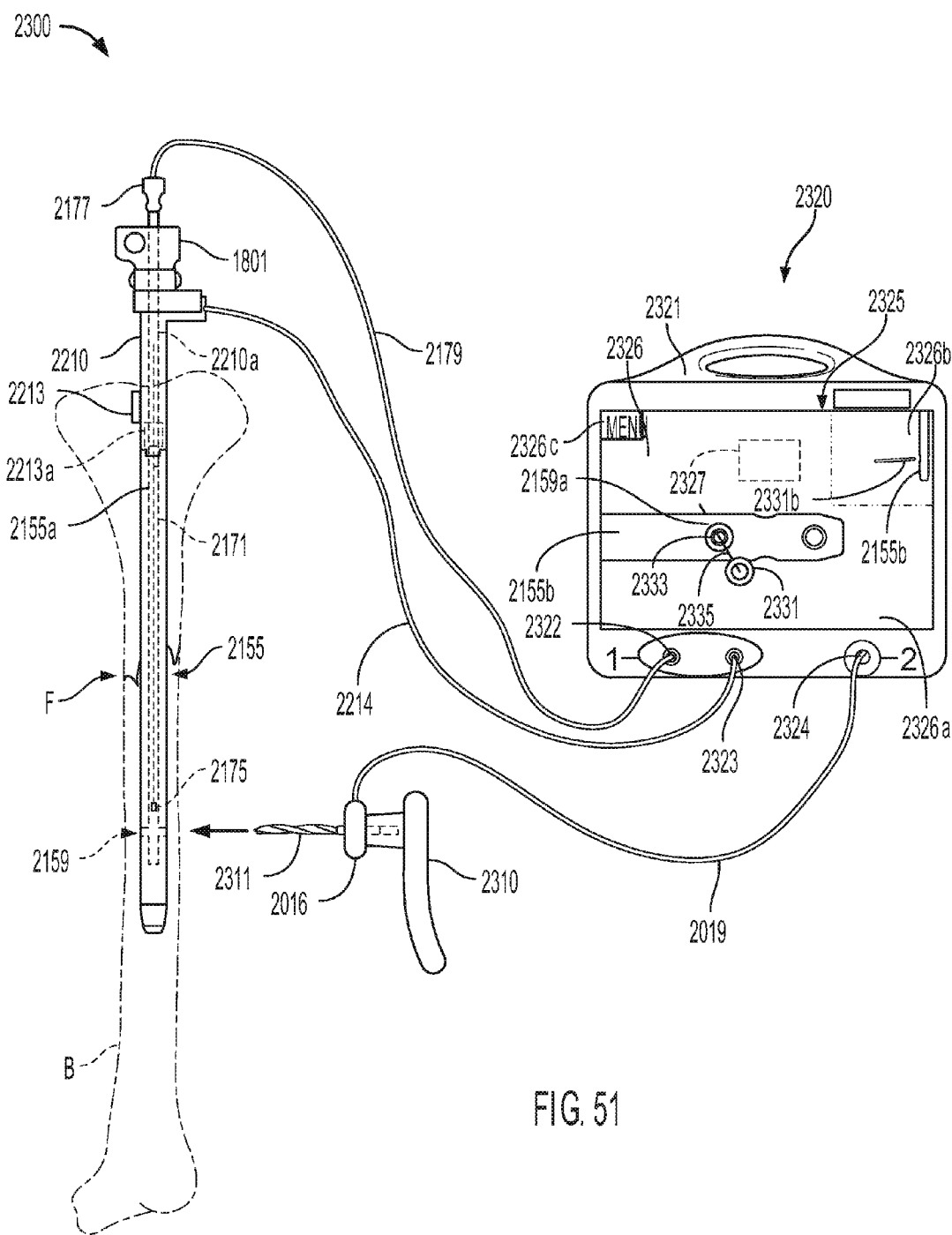
FIG. 51 is an illustration of a system for targeting a landmark of an implant.

The adjustable stop 1801 is used with a probe, such as the probe 2129 (FIG. 46), for targeting distal landmarks of the nail 2155, such as a distal aperture 2159 (FIG. 51). As described above, the adjustable stop 1801 can be attached to the insertion handle 2210 by a bolt 1807 (FIG. 43) that engages a threaded bore 2215 that is aligned with a longitudinal through hole of the insertion handle 2210 (not shown) that allows the probe to pass through the insertion handle 2210 and into the cannulation 2155*a* (FIG. 51) of the nail 2155. The adjustable stop 1801 also includes an arm 1809 that engages the body 2211 to prevent rotation between the adjustable stop 1801 and the insertion handle 2210.

Although not illustrated, the adjustable stop 1803 (shown in FIG. 45) can also be used with an insertion handle that includes an embedded sensor for targeting proximal landmarks of an implant.

In use, an orthopaedic implant, such as the intramedullary nail 2155, is implanted into bone. The insertion handle 2210 may be connected to the orthopaedic implant before or after implantation. Thereafter, a landmark identifier can be used for targeting of the proximal landmarks of the orthopaedic implant.

In some implementations, the distal landmarks are targeted prior to the proximal landmarks. As before, the insertion handle 2210 may be connected to the orthopaedic implant before or after implantation. The stop 1801 or the stop 1803 is connected to the insertion handle 2210. A probe is inserted into the stop, through the insertion handle 2210, and into the orthopaedic implant, such as the nail 2155. The distal landmarks are targeted, transfixion elements are placed in the distal landmarks to hold the orthopaedic implant, the probe is removed, and then the proximal landmarks are targeted.

Now referring to FIG. 51, a system 2300 for targeting a blind landmark of an orthopaedic implant is illustrated. The system 2300 includes the adjustable stop 1801, the probe 2171, and the insertion guide 2210 assembled and connected to the intramedullary nail 2155, which is implanted in a bone B that includes a fracture F. The intramedullary nail 2155 includes a distal aperture 2159 that extends through the intramedullary nail 2155 and is configured to receive a locking fastener (not shown). The probe 2171 is received through an aperture or the adjustable stop 1801, through a cannulation 2210*a* of the insertion handle 2210, and within a cannulation 2155*a* of the intramedullary nail 2155. The probe 2171 is received within the stop 1801 such that the sensor 2175 is positioned at a known distance from the distal aperture 2159. The known distance may range from zero to about 102 millimeters from the sensor 2175 to the distal aperture 2159 or other landmark. In other implementations, the known distance may range from about two millimeters to about twenty-five millimeters or from about three millimeters to about ten millimeters. In the depicted implementation, the known distance is about five millimeters.

The system 2300 also includes a tool, such as a drill 2310 that includes a drill bit 2311. The landmark identifier 2016 is engageable with the drill 2310 and/or the drill bit 2311 such that a position and orientation of the landmark identifier 2016 can be used to determine a position and orientation of the drill 2310 and/or the drill bit 2311. For example, the housing of the landmark identifier 2016 can include a friction fit engagement with the drill 2310, a strap, or other securing mechanism to at least temporarily secure the landmark identifier 2016 to the drill 2310. In other implementations, the landmark identifier 2016 can be integrated with the drill 2310, or other tool. In some implementations, the drill sleeve (not shown) may telescope to allow the user to place the tip of the drill sleeve against a patient and also allow the user to move the drill bit in a longitudinal direction for drilling.

A targeting system 2320 is operable to provide an indication to a user, such as a surgeon, of the relative position of a tool, such as a drill 2310 that includes a drill bit 2311, relative to the distal aperture 2159. The targeting system 2320 includes a housing 2321, a first sensor port 2322, a second sensor port 2323, a field generator port 2324, a display device 2325, and a processor 2327. The first sensor port 2322 is configured to receive a connector of the cable 2179 of the probe 2171 such that the targeting system 2320 receives signals generated by the sensor 2175. The second sensor port 2323 is configured to receive a connector of a cable 2214 that is connected to the sensor 2213 of the insertion handle 2210 such that the targeting system 2320 receives signals generated by the sensor 2213. The field generator port 2324 is configured to receive a connector of a cable 2019 of the landmark identifier 2016 such that the targeting system 2320 transmits signals via the cable 2019 to control the operation of the field generator of the landmark identifier 2016. The display device 2325 is operable to output a display of a graphical user interface 2326 that includes a representation of the position and orientation of the drill 2310 relative to a location and orientation of a landmark of the intramedullary nail 2155, such as the distal aperture 2159, the proximal aperture 2157 (FIG. 50), or another landmark.

The processor 2327 is operable to receive signals from the distal sensor 2175 and/or the proximal sensor 2213, and to determine, based on the received signal(s), a current position and orientation of the landmark identifier 2016 relative to a selected landmark of the intramedullary nail 2155. For example, a feature of a signal received from the distal sensor 2175, such as one or more induced electrical currents, can be used by the processor 2327 to determine a distance of the landmark identifier 2016 from the sensor 2175, as well as an orientation of a magnetic moment of a field generated by the landmark identifier 2016. For example, the sensor 2175 can transmit a signal indicative of a current value and an identifier that indicates which of a plurality of induction coils produced the associated current value. The processor 2327 can compare the received current values with reference values associated with each of the induction coils to determine differences between the received values and the reference values. The reference values can be values of induced current associated with a reference field generation signal, a reference position, and a reference orientation of the landmark identifier 2016. The processor 2327 uses these determined differences between the received and reference values to determine a difference in position and orientation of the landmark identifier 2016 from the reference position and orientation based on any determined difference in the magnetic field generated by the landmark identifier 2016 from the reference field. Based on the difference in position and orientation of the landmark identifier 2016 and the reference position and orientation, a current position and orientation of the landmark identifier 2016 relative to the sensor 2175 can be determined by the processor 2327.

The current distance and orientation of the landmark identifier 2016 relative to the sensor 2175 are used by the processor 2327 to determine the current distance of the landmark identifier 2016 from the distal aperture 2159 and the current relative orientation of the magnetic moment of the generated magnetic field relative to a central through-axis of the distal aperture 2159. For example, the processor 2327 determines the current distance and relative orientation of the landmark identifier 2016 relative to the distal aperture 2159 based on a known position and orientation of the distal aperture 2159 relative to the distal sensor 2175. The processor 2327 also determines a current position of the drill 2310, including the drill bit 2311, from the distal aperture 2159 as well as a current orientation of the drill 2310 and the drill bit 2311 relative to the central through-axis of the distal aperture 2159 based on a known position and orientation of the drill 3210 and the drill bit 2311 relative to the location of the landmark identifier 2016 and the magnetic moment of the field generated by the landmark identifier 2016. In the case of the landmark identifier 2016, a longitudinal axis of the drill bit 2311 is coaxial with the magnetic moment of the magnetic field generated by the landmark identifier 2016.

The graphical user interface 2326 is generated by the processor based on the determined current position and orientation of the drill 2310 and the drill bit 2311 relative to the distal aperture 2159, or based on a current position and orientation of another tool relative to another landmark. The graphical user interface 2326 includes a first portion 2326a that includes an intramedullary nail image 2155b that represents the intramedullary nail 2155 and includes a distal aperture image 2159a that represents the distal aperture 2159. The first portion 2326a of the graphical user interface 2326 also includes an orientation indicator 2330 that includes a first circle 2331, a second circle 2333, and a line 2335 that intersects the centers of each of the first circle 2331 and the second circle 2333. The line 2335 provides an illustration to the user of the current orientation of the drill bit 2311 relative to the central through axis of the distal aperture 2159. Particularly, when the first circle 2331 and the second circle 2333 are both disposed entirely within the distal aperture image 2159a, then the longitudinal axis of the drill bit 2311 is co-axial with the central through axis of the distal aperture 2159, as shown in FIG. 51. The graphical user interface 2326 also includes a second portion 2326b that includes intramedullary nail image 2155b and a drill bit image 2331b. The current position and orientation of the drill bit 2311 relative to the intramedullary nail 2155 is illustrated in the second portion 2326b of the graphical user interface 2326.

In use, the probe 2155, the insertion handle 2210, the adjustable stop 1801, the landmark identifier 2016, the drill 2310, and the drill bit 2311 can be sterilized, such as by autoclaving, if one or more of the components is not sterile. When sterile, the probe 2155 is connected with the first sensor port 2322 of the targeting system 2320 and the insertion handle 2210 is connected with the second sensor port 2323 of the targeting system 2320. The processor 2327 detects the connection of the distal sensor 2175 and the proximal sensor 2213 and can optionally cause a display of an indication of the proper (or improper) connection of the probe 2155 and the insertion handle 2210 and/or an indication of the proper (or improper) operation of the distal sensor 2175 and the proximal sensor 2213. Similarly, the landmark identifier 2016 is connected with the field generator port 2324, and the processor can detect the connection of the landmark identifier 2016 and cause a display of the proper (or improper) connection of the landmark identifier 2016 and/or the proper (or improper) operation of the field generator of the landmark identifier 2016. The sensor 2175 is connected to a Programmable Read-Only Memory (PROM) microchip that stores the calibration values and also stores an identifier that identifies the sensor 2175 as a distal targeting sensor. When the sensor is connected to the processor 2327, the processor 2327 automatically identifies the type of targeting contemplated and may display an indication on graphical user interface 2326 that a sensor of the identified type is connected.

The insertion handle 2210 is engaged with the intramedullary nail 2155 and the adjustable stop 1801 is engaged with the insertion handle 2210. The probe 2155 is then inserted in the adjustable stop 1801 and positioned at a desired location. The button 1802 is manipulated to allow the probe 2155 to be adjusted, and the button 1802 is released to clamp the probe 2155 in a desired position. For example, the probe 2155 can be inserted until a reference mark, such as a printed mark or a detent or other structure of the probe 2155 is correctly positioned relative to a reference portion of the adjustable stop 1801. The positioning of the probe 2155 locates the distal sensor 2175 in the correct position relative to the distal aperture 2159.

A drill sleeve 2022 is selected and engaged with the drill sleeve attachment 2020 of the landmark identifier 2016. For example, one of a short drill sleeve and a long drill sleeve is selected. An indication of the selection is input to the targeting system 2320, such as by interaction with a menu 2326c of the graphical user interface 2326. Additionally, an indication of the specific intramedullary nail 2155, insertion handle 2210, adjustable stop 1801, and/or probe 2171 is input to the targeting system 2320, if not automatically recognized by the targeting system 2320 and/or to confirm the specific intramedullary nail 2155, insertion handle 2210, adjustable stop 1801, and/or probe 2171.

The accuracy of the targeting system 2320 is checked before implantation of the intramedullary nail 2155 by placing the landmark identifier 2016 directly over the distal aperture 2159 of the intramedullary nail 2155, which can be done by inserting the tip 2024 of the drill sleeve 2022 within the distal aperture 2159. If the second circle 2333 is shown within the distal aperture image 2159a, and if the orientation of the line 2335 corresponds to the orientation of the drill sleeve 2022, then the targeting system 2320 is accurate. If the targeting system is not accurate, the input indications of selected components, and/or the position of the probe 2171 are checked. If no errors are found, then the targeting system 2320 is recalibrated, as described below with reference to FIG. 52.

When the components are assembled and checked as described above, the intramedullary nail 2155 is implanted in the bone B. When the intramedullary nail 2155 is located in the desired position, the tip 2024 of the drill sleeve 2022 is placed over the distal aperture 2159. When the landmark identifier 2016 is brought near the sensor 2175, a signal generated by the sensor 2175 is received by the processor 2327, and one or more signal feature, such as a current value, and an identifier are used by the processor to determine that distal targeting is being attempted, and the targeting system 2320 enters a distal targeting mode. Locating the tip 2024 relative to the distal aperture 2159, which is hidden within the bone B, is performed by a user by making reference to the graphical user interface 2326 in the distal targeting mode, and is confirmed when the first circle 2331 and the second circle 2333 are located within the distal aperture image 2159a.

An incision is made in the skin at the location of the distal aperture 2159. The drill sleeve 2022 is then inserted into the incision down to the bone B. The landmark identifier 2016 is then manipulated by a user to arrange both the first circle 2331 and the second circle 2333 completely within the distal aperture image 2159a and, while maintaining the position and orientation of the landmark identifier 2016, the drill bit 2311 is inserted through the drill sleeve 2022 and a user drills through the bone B, through the distal aperture 2159, to the cortex on the far side of the bone B. A desired drill depth can be achieved by the user by referring to the second portion 2326b, or by comparing one or more reference marks included on the drill bit 2311 to a reference portion of the landmark identifier 2016.

The drill bit 2311 is then removed and a locking fastener (not shown) is engaged with the bone B and the distal aperture 2159 through the drill sleeve 2022, again maintaining the first circle 2331 and the second circle 2333 within the distal aperture image 2159a. A desired depth of insertion of the locking fastener can be achieved by a user by referring to the second portion 2326b of the graphical user interface 2326, or by comparing a reference marking on a fastener driving tool (not shown) to a reference portion of the landmark identifier 2016.

In addition to engaging the locking fastener with the distal aperture 2159, the targeting system 2320 can be used to target a proximal landmark of the intramedullary nail 2155. For example, before or after engaging the locking fastener with the distal aperture 2159 and the bone B, a user can select the sensor 2213 from the menu 2326c or move the landmark identifier 2016 within a predetermined distance of the sensor 2213, which causes the targeting system 2320 to enter a proximal targeting mode and output a display of the relative position and orientation of the drill 2300 and/or the drill bit 2016 relative to a proximal landmark of the intramedullary nail 2155, such as the proximal aperture 2157 (FIG. 50). A user can then engage a fastener or other tool or implant with the proximal landmark in a manner similar to that described above with respect to drilling through the distal aperture 2159 and/or engaging the locking fastener with the distal aperture 2159.

As mentioned above, a proximal landmark can be targeted using the targeting system 2320 and the sensor 2213 before or after targeting a distal landmark, such as the distal aperture 2159. Particularly, a proximal landmark can be targeted before insertion of the probe 2171 within the adjustable stop 1801, the insertion handle 2210, and/or the intramedullary nail 2155. The proximal landmark can also be targeted after removal of the probe 2171, or while the probe 2171 is inserted within the adjustable stop 1801, the insertion handle 2210, and/or the intramedullary nail 2155. For example, as discussed above, the probe 2171 can be inserted through a portion of the intramedullary nail 2155 that does not interfere with engagement of the drill bit 2311 or the fastener with a proximal aperture or other proximal landmark. Additionally, if the probe 2171 is inserted into the cannulation 2155a and the proximal aperture also passes through the cannulation 2155a, the cannulation 2155a can be large enough to simultaneously accommodate both a fastener or the drill bit 2311 and the probe 2171. For example, the probe 2171 can be dimensioned to be disposed in a gap between the drill bit 2311 and an inner wall of the intramedullary nail 2155 that defines the cannulation 2155a. Similarly, the probe 2181 (FIG. 48), which has both the distal sensor 2185 and the proximal sensor 2186, can be inserted in the cannulation 2155a and both distal and proximal landmarks of the intramedullary nail 2155 can be targeted without removal or adjustment of the probe 2181.

Alternatively, a proximal landmark of the intramedullary nail 2155 can be targeted using the targeting system 2320 and either the sensor 2175 of the probe 2171 or the sensor 2165 of the probe 2161 (FIG. 47). For example, after engaging the locking faster with the distal aperture 2159, the probe 2171 can be adjusted using the adjustable stop 1801 to secure the sensor 2175 in a predetermined location relative to one or more proximal landmarks of the intramedullary nail 2155. The menu 2326c can then be used to select a proximal targeting mode such that the targeting system 2320 is operable to display a position and orientation of the drill 2310 and/or the drill bit 2311 (or other tool or implant) relative to the proximal landmark(s). Similarly, and particularly where it is undesirable to have a portion of the probe 2171 extending a distance from the adjustable stop 1801, the probe 2161 can be connected to the targeting system 2320 and inserted in the adjustable stop 1801 such that the sensor 2165 is located in a know location relative to one or more proximal landmarks of the intramedullary nail 2155. In either case, one or more proximal landmarks of the intramedullary nail can then be targeted using the targeting system 2320, as described above. In other implementations, the proximal landmark(s) can be targeted before the distal aperture 2159 using the prone 2171 or the probe 2161.

Figure 52:
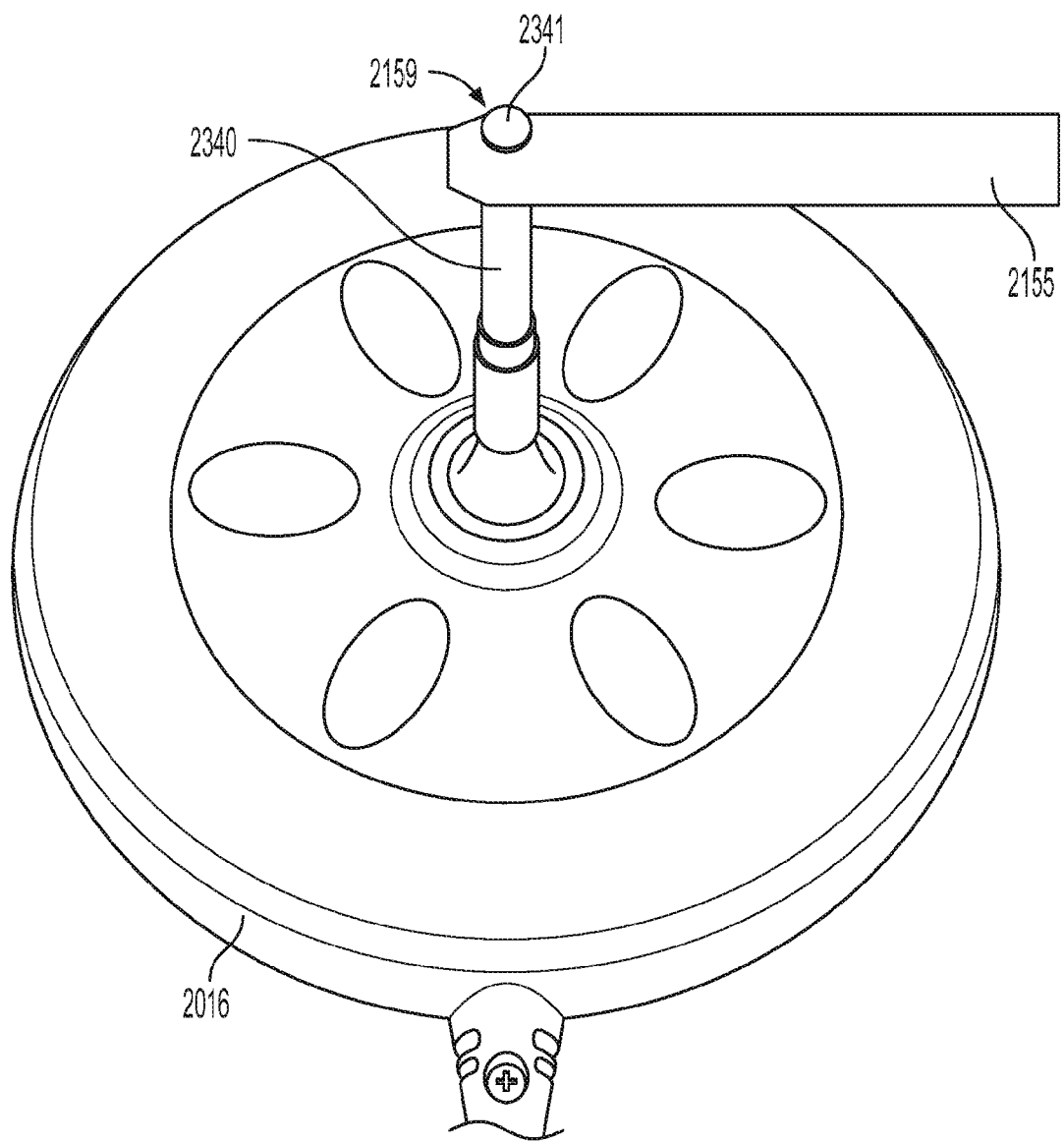
FIG. 52 is an illustration of a device for use in calibrating the system of FIG. 51.
Figure 53:
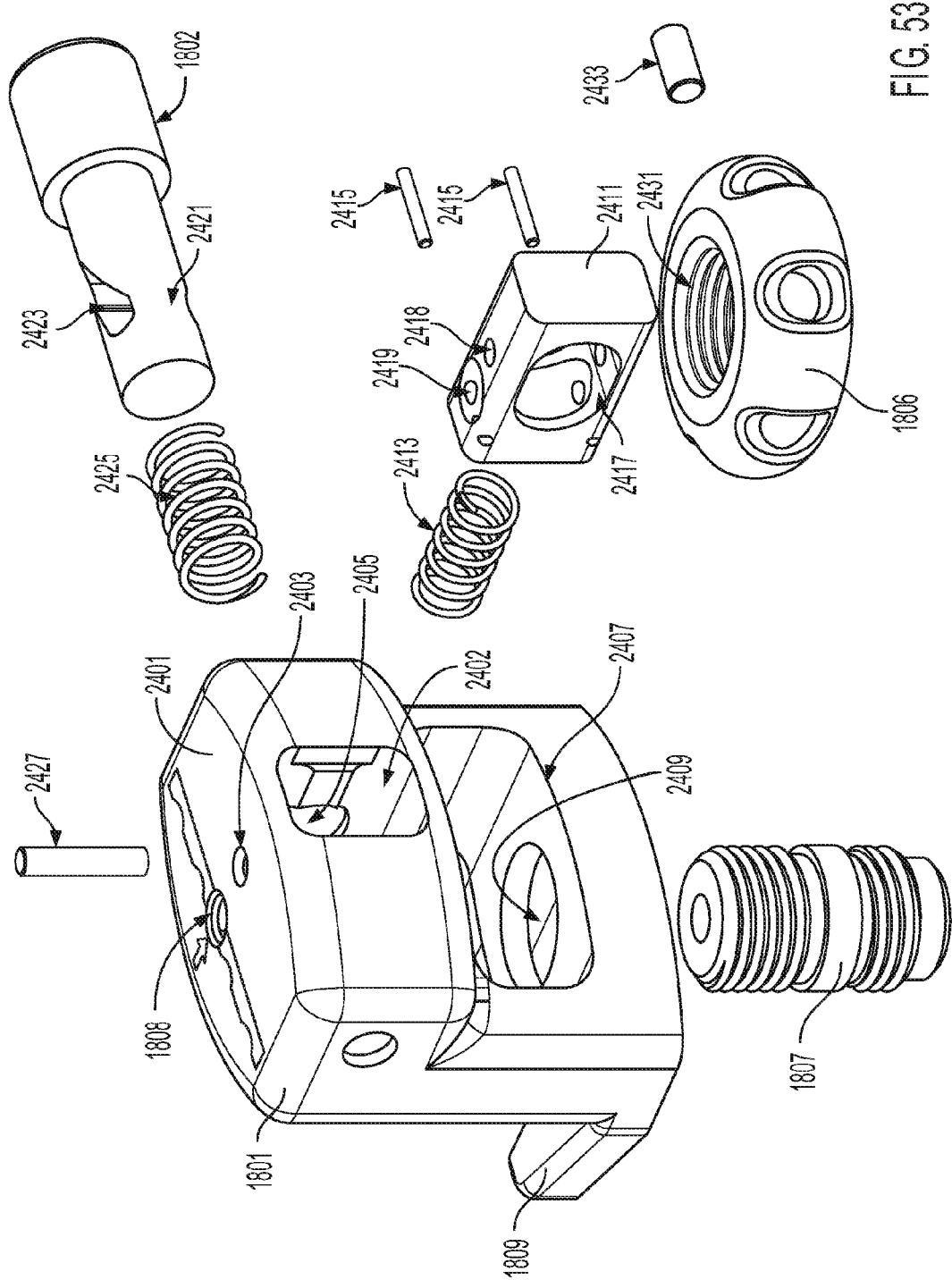
Figure 56:
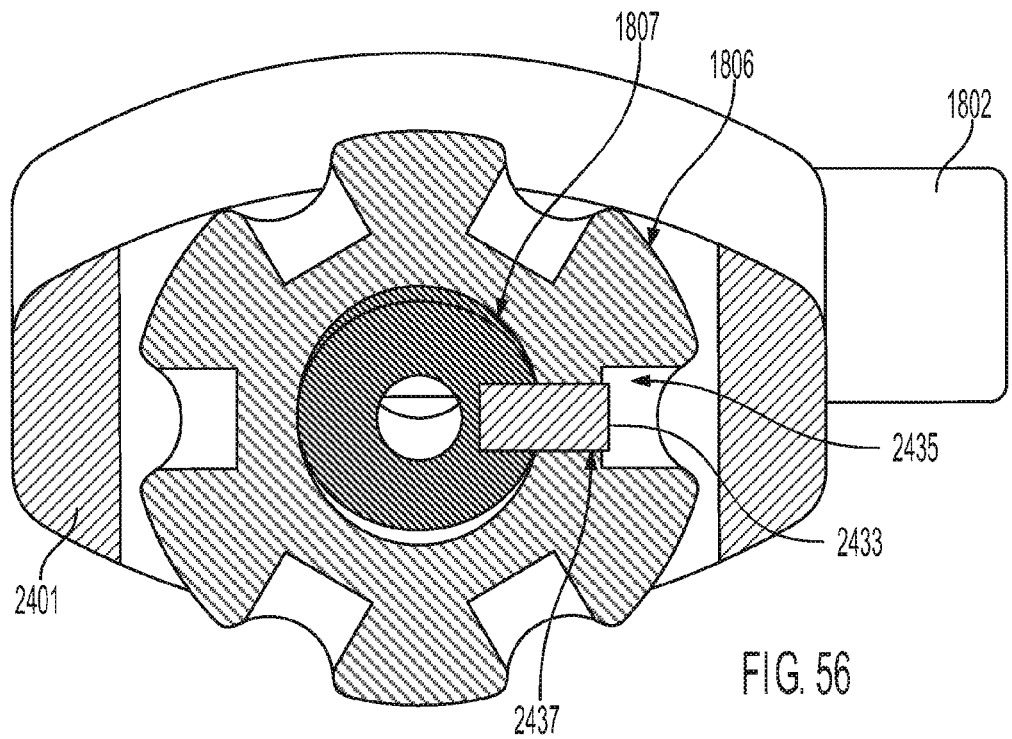
Figure 57:
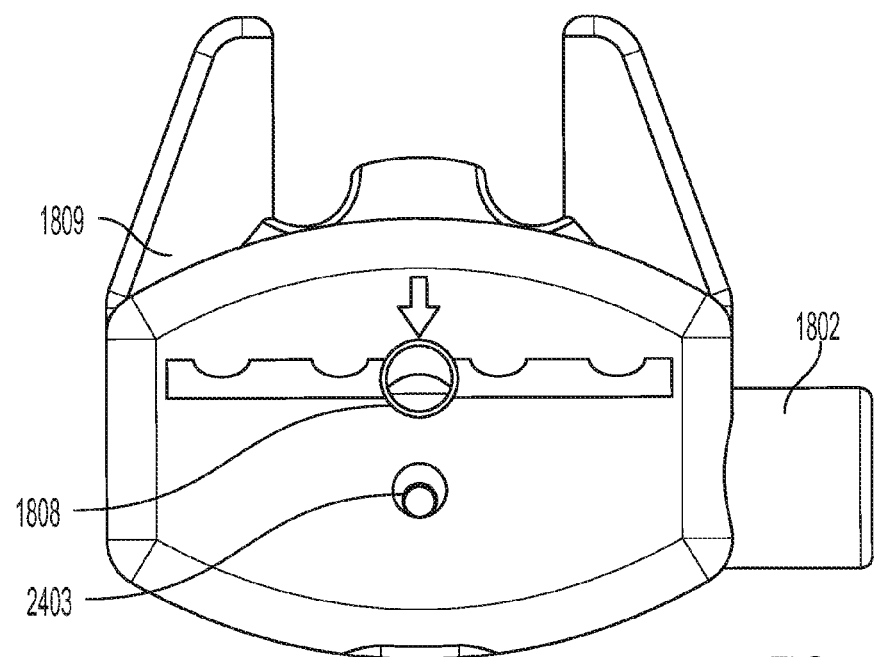

Now referring to FIG. 52, a calibration member 2340 is attached to the landmark identifier 2016 and the intramedullary nail 2155 for use in calibrating the targeting system 2320. For example, if the accuracy of the targeting system 2320 is checked before inserting the intramedullary nail 2155 and errors are found, the targeting system 2320 can be re-calibrated. In use, the calibration member 2340 is engaged with the landmark identifier 2016. Then a tip 2341 is inserted into the distal aperture 2159 until a reference portion (not shown) of the calibration member 2340 abuts the intramedullary nail 2155. Re-calibration of the targeting system 2320 can then be achieved by interaction with the menu 2326c of the graphical user interface 2326. For example, a "re-calibrate" option may be selected from the menu 2326c, which causes the targeting system 2320 to transmit a driving signal to the field generator of the landmark identifier 2016 and to store as reference values any current values received from the sensor 2175 of the probe 2171. The graphical user interface 2326 can display an indication of a successful re-calibration of the targeting system 2320.

Now referring to FIGS. 53-57, details of the adjustable stop 1801 are illustrated. The adjustable stop 1801 includes a housing 2401 that includes a clamp member slot 2402. A clamp member 2411 is received within the clamp member slot 2402 and is biased by a spring 2413. The clamp member 2411 is retained within the housing 2401 by pins 2415. The clamp member 2411 also includes an actuator slot 2417, a linkage aperture 2418, and a probe aperture 2419.

The button 1802 includes an actuating shaft 2421 and an actuating slot 2423. The actuating shaft 2421 is received within an aperture 2405 of the housing 2401 and is biased against insertion into the housing by a spring 2425. When assembled, the actuating shaft 2421 is received in the actuator slot 2417 of the clamp member 2411 and is retained in the housing 2401 by a linkage pin 2427 that is inserted into the actuating slot 2423 of the actuating shaft 2421 through an opening 2403 of the housing 2401 and through the linkage aperture 2418 of the clamp member 2411. In use, when the button 1802 is depressed against the biasing force of the spring 2425, the linkage pin 2427 is moved within the actuating slot 2423 which pushes the clamp member 2411 against the spring 2413 to allow a probe to be inserted into the hole 1808 and through the probe aperture 2419. When the probe is inserted and the button 1802 is released, the springs 2413 and 2425 cause the clamp member 2411 to bear against the probe to maintain the position of the probe within the hole 1808.

The thumb wheel 1806 is received within a thumb wheel slot 2407 of the housing 2401 and the bolt 1807 is threaded into a threaded aperture 2431 of the thumb wheel 1806 through a bolt aperture 2409 of the housing 2401. After the bolt 1807 is threaded into the bolt aperture 2431, a pin 2433 is inserted through an aperture 2435 (FIG. 56) of the thumb wheel 1806 and into a slot 2437 (FIG. 56) of the bolt 1807 to retain the bolt 1807 in engagement with the thumb wheel 1806.

Now referring to FIGS. 58-62, details of the adjustable stop 1803 are illustrated. The adjustable stop 1803 includes a housing 2501 that includes a clamp member slot 2502. A clamp member 2511 is received within the clamp member slot 2502 and is biased by a spring 2513. The clamp member 2511 is retained within the housing 2501 by pins 2515. The clamp member 2511 also includes an actuator slot 2517, a linkage aperture 2518, and a probe aperture 2519.

The button 1802 includes an actuating shaft 2421 and an actuating slot 2423. The actuating shaft 2421 is received within an aperture 2405 of the housing 2401 and is biased against insertion into the housing by a spring 2525. When assembled, the actuating shaft 2421 is received in the actuator slot 2517 of the clamp member 2511 and is retained in the housing 2501 by a linkage pin 2527 that is inserted into the actuating slot 2423 of the actuating shaft 2421 through an opening 2503 of the housing 2401 and through the linkage aperture 2418 of the clamp member 2511. In use, when the button 1802 is depressed against the biasing force of the spring 2525, the linkage pin 2527 is moved within the actuating slot 2423 which pushes the clamp member 2511 against the spring 2513 to allow a probe to be inserted into the hole 1805 and through the probe aperture 2519. When the probe is inserted and the button 1802 is released, the springs 2513 and 2525 cause the clamp member 2511 to bear against the probe to maintain the position of the probe within the hole 1805.

A threaded bolt 2531 of the clamp knob 1804 is threaded into a bolt aperture 2509 of the housing 2501 to secure the adjustable stop 1803 to an insertion handle.

System calibration may be accomplished during manufacturing, after distribution, or immediately preceding implant implantation. The calibration step is analogous to registration in computer assisted surgery. Calibration may be needed for different reasons. For example, sensor calibration may be needed to correct for manufacturing tolerances. The system may be designed based upon a computer-aided-design model, and calibration is used to accurately place the sensors relative to one another. The processor or the control unit may include software to generate X, Y, Z, pitch, yaw, and roll offset values to locate the sensors in a global coordinate system or simply placement relative to one another. The system may be manufactured and calibrated during manufacturing and assigned a unique identifier, such as a serial number, color code, bar code, or RFID tag. If the system needs to be re-calibrated, the unique identifier may be used to retrieve the offset values, either locally or over a network. Further, the unique identifier may be used to retrieve other data, such as the size of the intramedullary nail or the length of the intramedullary nail and/or the probe.

The systems for identifying a landmark may be used for other purposes beyond targeting blind screw holes of an implanted intramedullary nail. These include, but are not limited to, targeting blocking screws and aligning guide pins. In one procedure, blocking (poller) screws can be inserted into the bone directly outside and tangent to the nail or rod. Targets are shown as two lines on the screen on opposing sides of the nail, such as anterior-posterior or medial-lateral, and offset from the nail at a distance, for example, 2.5 mm. The surgeon aligns the landmark identifier to one of the lines as determined by anatomical side where he or she wishes to place the blocking screw. Other symbols or indicia such as dots, bull's-eyes or combinations thereof can be used as targets shown on the screen. For this application, devices that are insertable in the medullary canal and instrumented with a sensor or sensors can be used as a means to target blocking screws, including but not limited to, a probe, a reducer or an awl. The depicted systems for identifying a landmark can also be used to align or center a guide pin in both A-P and M-L planes for placement of a lag screw in the proximal portion of a femoral nail. An exemplary implementation of this system may include a sensor placed with known orientation and location relative to and in the insertion handle and/or drill guide and/or alignment jig which is removably attached to the proximal portion of the femoral nail.

While FIG. 1 illustrates a pocket for affixing the first sensor to the implant, other structure and/or methods may be used to affix these items together. For example, probes of varying length may be used to place the first sensors in the appropriate position as illustrated in FIG. 42. The adjustable stops 1801, 1803 of FIGS. 41-42 may be used to precisely position the sensor 2126 in the implant 30.

While only certain implementations have been set forth, alternatives and modifications will be apparent from the above description to those skilled in the art. These and other alternatives are considered equivalents and within the spirit and scope of this disclosure and the appended claims.

The invention claimed is:
1. A system for targeting a landmark on an orthopaedic implant comprising:
   an autoclavable device comprising:
      an autoclavable housing comprising an outer covering; and
      a field generator for generating an electromagnetic field, the field generator comprising a plurality of magnetic field generating elements disposed within the outer covering of the housing, wherein the autoclavable device is configured to be operable to generate the electromagnetic field for targeting the landmark after being subjected to autoclave sterilization;
   an electromagnetic sensor for disposition at a set distance from the landmark, the electromagnetic sensor being configured to generate sensor data in response to the generated electromagnetic field, the generated sensor data indicating a relative position of the electromagnetic sensor with respect to the autoclavable device; and
   a drill guide removably coupleable to the housing of the autoclavable device.

2. The system of claim 1, further comprising a removable probe that extends into the orthopaedic implant, the electromagnetic sensor being coupled to the removable probe.

3. The system of claim 2, further comprising an adjustable stop that is connectable to the orthopaedic implant, the adjustable stop comprising a slot through which removable probe extends, the adjustable stop comprising a clamping mechanism to hold the removable probe in a fixed position with respect to the adjustable stop.

4. The system of claim 3, wherein the removable probe comprises a plurality of spaced apart indicators, and the clamping mechanism is configured to be selectively set to hold the removable probe in a fixed position at an indicator or between two indicators.

5. The system of claim 1, wherein the autoclavable device comprises a removable second covering placed over the outer covering.

6. The system of claim 5, wherein the autoclavable device comprises an autoclavable internal mounting structure formed of a non-magnetic material, the autoclavable internal mounting structure being located within the outer covering, the plurality of magnetic field generating elements being mounted to the autoclavable internal mounting structure.

7. The system of claim 1, wherein the autoclavable device defines a central opening, and the drill guide is configured to couple to the autoclavable device around the central opening.

8. The system of claim 7, wherein the drill guide comprises a sleeve or tube having an opening aligned with the central opening of the autoclavable device when the drill guide is attached to the autoclavable device.

9. The system of claim 1, further comprising a processor configured to receive sensor data from the electromagnetic sensor and determine a position of the autoclavable device based on the sensor data.

10. The system of claim 9, further comprising a display, wherein the processor is configured to cause the display to indicate a position of an axis of the drill guide relative to the orthopaedic implant.

11. The system of claim 1, wherein the outer covering is formed of silicone.

12. The system of claim 1, wherein the plurality of magnetic field generating elements is encapsulated within the outer covering.

13. The system of claim 1, wherein the plurality of magnetic field generating elements comprises at least three induction coils.

14. The system of claim 1, wherein the drill guide has a serrated tip.

15. The system of claim 1, wherein the autoclavable device is configured to produce a sequence of multiple spatial magnetic field shapes.

16. The system of claim 1, wherein the electromagnetic sensor is an inductive sensor.

17. The system of claim 1, wherein the electromagnetic sensor is configured to provide data indicating a position of the electromagnetic sensor in six degrees of freedom.

18. The system of claim 1, wherein the autoclavable device defines a plurality of indentations spaced apart along an exterior of the autoclavable device.

19. The system of claim 1, wherein the autoclavable device is disk-shaped.

20. The system of claim 1, wherein the orthopaedic implant comprises one of an intramedullary nail, a bone plate, a hip prosthetic, a knee prosthetic, and a shoulder prosthetic.

* * * * *